United States Patent
Corti

(10) Patent No.: US 9,498,531 B2
(45) Date of Patent: Nov. 22, 2016

(54) ANTIBODIES THAT NEUTRALIZE RSV, MPV AND PVM AND USES THEREOF

(71) Applicant: Humabs BioMed SA, Bellinzona (CH)

(72) Inventor: Davide Corti, Bellinzona (CH)

(73) Assignee: Humabs BioMed SA, Bellinzona (CH)

( * ) Notice: Subject to any disclaimer, the term of this patent is extended or adjusted under 35 U.S.C. 154(b) by 176 days.

(21) Appl. No.: 13/827,845

(22) Filed: Mar. 14, 2013

(65) Prior Publication Data

US 2014/0037648 A1 Feb. 6, 2014

Related U.S. Application Data

(60) Provisional application No. 61/655,310, filed on Jun. 4, 2012, provisional application No. 61/613,197, filed on Mar. 20, 2012.

(51) Int. Cl.
*A61K 39/42* (2006.01)
*C07K 16/10* (2006.01)
*A61K 39/00* (2006.01)

(52) U.S. Cl.
CPC .......... *A61K 39/42* (2013.01); *C07K 16/1027* (2013.01); *A61K 2039/505* (2013.01); *C07K 2317/21* (2013.01); *C07K 2317/33* (2013.01); *C07K 2317/34* (2013.01); *C07K 2317/41* (2013.01); *C07K 2317/565* (2013.01); *C07K 2317/76* (2013.01); *C07K 2317/92* (2013.01); *C12N 2760/18522* (2013.01)

(58) Field of Classification Search
None
See application file for complete search history.

(56) References Cited

U.S. PATENT DOCUMENTS

2006/0228367 A1   10/2006   Ulbrandt et al.

FOREIGN PATENT DOCUMENTS

| WO | 2004092207 A2 | 5/2004 |
|---|---|---|
| WO | 2004076677 A2 | 9/2004 |
| WO | 2010046775 A2 | 4/2010 |
| WO | 2010149743 A2 | 6/2010 |
| WO | WO 2010/149743 | * 12/2010 |
| WO | 2013140247 A1 | 9/2013 |

OTHER PUBLICATIONS

Paul Fundamental Immunology 3rd 1993, pp. 242, 292-295.*
Rudikoff et al, Proc. Natl. Acad. Sci. (PNAS) vol. 79 pp. 1979-1983 1982.*
Coleman Reasearch Immunology 1994 vol. 145, pp. 33-36.*
Casset Biochem Biophys Research Com 2003, vol. 307, pp. 198-205.*
SEQ 10 from WO2010149743 published 2010.*
Corti et al., Nature. 2013, vol. 501, :pp. 439-443.*
Alto WA, 2004, Human Metapneumovirus: A Newly Described Respiratory Tract Pathogen, The Journal of the American Board of Family Practice / American Board of Family Practice 17:466-469.
Bonville et al., 2004, Functional Antagonism of Chemokine Receptor CCR1 Reduces Mortality in Acute Pneumovirus Infection In Vivo, Journal of Virology 78:7984 7989.
Collins et al., 1984, Nucleotide sequence of the gene encoding the fusion (F) glycoprotein of human respiratory syncytial virusPNAS 81:7683-7687.
de Swart et al., 2007, Immunization of macaques with formalin-inactivated human metapneumovirus induces hypersensitivity to hMPV infection, Vaccine 25:8518-8528.
Fulginiti et al., 1969, Respiratory virus immunization. I. A field trial of two inactivated respiratory virus vaccines; an aqueous trivalent parainfluenza virus vaccine and an alum-precipitated respiratory syncytial virus vaccine, American Journal of Epidemiology 89:435-448.
Glezen et al., 1981, Risk of respiratory syncytial virus infection for infants from low-income families in relationship to age, sex, ethnic group, and maternal antibody level, The Journal of Pediatrics 98:708-715.
Greensill et al, 2003, Human Metapneumovirus in Severe Respiratory Syncytial Virus Bronchiolitis, Emerging Infectious Diseases 9:372-375.
Holliger and Hudson, 2005, Engineered antibody fragments and the rise of single domains, Nature Biotechnology 9: 1126-1136.
JohnsonS et al., 1999, A Direct Comparison of the Activities of Two Humanized Respiratory Syncytial Virus Monoclonal Antibodies: MEDI-493 and RSHZ19, The Journal of Infectious Diseases 180:35-40.
Kapikian et al., 1969, An epidemiologic study of altered clinical reactivity to respiratory syncytial (RS) virus infection in children previously vaccinated with an inactivated RS virus vaccine, American Journal of Epidemiology 89:405-421.

(Continued)

*Primary Examiner* — Shanon A Foley
*Assistant Examiner* — Myron Hill
(74) *Attorney, Agent, or Firm* — Dennis A. Bennett

(57) ABSTRACT

The invention relates to antibodies, and antigen binding fragments thereof, that neutralize infection of both RSV, MPV and PVM. The invention also relates to nucleic acids that encode, immortalized B cells and cultured plasma cells that produce, and to polypeptides that bind to such antibodies and antibody fragments. In addition, the invention relates to the use of the antibodies, antibody fragments, and polypeptides recognized by the antibodies of the invention in screening methods as well as in the diagnosis, treatment and prevention of RSV or MPV infection and RSV and MPV co-infection.

26 Claims, 24 Drawing Sheets

(56) References Cited

OTHER PUBLICATIONS

Kim et al., 1969, Respiratory syncytial virus disease in infants despite prior administration of antigenic inactivated vaccine, American Journal of Epidemiology 89:422-434.
Martino et al., 2005, Prospective Study of the Incidence, Clinical Features, and Outcome of Symptomatic Upper and Lower Respiratory Tract Infections by Respiratory Viruses in Adult Recipients of Hematopoietic Stem Cell Transplants for Hematologic Malignancies, Biol Blood and Marrow Transplant, Journal of the American Society for Blood and Marrow Transplantation 11:781-796.
McIntosh et al., 1978, The immunologic response to infection with respiratory syncytial virus in infants The Journal of Infectious Diseases 138:24-32.
McLellan et al. 2011, Structure of Respiratory Syncytial Virus Fusion Glycoprotein in the Postfusion Conformation Reveals Preservation of Neutralizing Epitopes, J Virol, p. 7788-7796.
Meissner et al., 1999, Safety and Pharmacokinetics of an Intramuscular Monoclonal Antibody (SB 209763) against Respiratory Syncytial Virus (RSV) in Infants and Young Children, Antimicrobial Agents and Chemotherapy 43:1183-1188.
Ogra, 2003, Respiratory syncytial virus: The virus, the disease and the immune response, Paediatric Respiratory Reviews 5 Suppl A:S119-S126.
Rosenberg and Domachowske, 2008, Pneumonia Virus of Mice Severe Respiratory Virus Infection in a Natural Host, Immunology Letter 118:6-12.
Swanson et al., 2011, Structural basis for immunization with postfusion respiratory syncytial virus fusion F glycoprotei (RSVF) to elicit high neutralizing antibody titers, PNAS, vol. 108, No. 23, 9619-9624.
Thompson, W.W. et al., 2003, Mortality associated with influenza and respiratory syncytial virus, JAMA, 289:179-186.
Ulbrandt et al., 2008, Identification of antibody neutralization epitopes on the fusion protein of human metapneumovirus, J General Virol, 89, 3113-3118.
Williams et al., 2004, Human Metapneumovirus and Lower Respiratory Tract Disease in Otherwise Healthy Infants and Children, N Engl J Med 350:443-450.
Wyde et al., 2003, Comparison of the inhibition of human metapneumovirus and respiratory syncytial virus by ribavirin and immune serum globulin in vitro, Antiviral Research 60:51-59.
Yin, et al., 2006, Structure of the parainfluenza virus 5 F protein in its metastable, prefusion conformation, Nature 439:38-44.
Zhao and Sullender, 2005, In Vivo Selection of Respiratory Syncytial Viruses Resistant to Palivizumab, Journal of Virology 79:3962-3968.
Zhao et al., 2004, Respiratory syncytial virus escape mutant derived in vitro resists palivizumab prophylaxis in cotton rats, Virology 318, pp. 608-612.
Magro M. et al., Neutralizing antibodies against the preactive form of respiratory syncytial virus fusion protein offer anique possibilities for clinical intervention, 2012 PNAS, 109(8), 3089-3094.
Ling R et al., Polypeptides of pneumonia virus of mice. I. Immunological cross-reactions and post-translational modifications,1989, J Gen Virol., 1427-1440.
Corti, Davide et al., Antibodies That Neutralize RSV, MPV and PVM and Uses Thereof, Humabs Biomed SA, WO2013140247A1, International Preliminary Report on Patentability Chapter I, published Sep. 26, 2013 9 pages.

* cited by examiner (A)                                    (B)

| | |
|---|---|
| RSV | S A V S K G Y L S A L R T G W Y T S V I T I E L S N I |
| BRSV | . . . . R . . . . . . . . . . . . . . . V . . . . K . |
| PVM | . V E T A . . K . . . . . . . H M T . M S . K . . Q . |
| MPV | . T I T E . . . . V . . . . . . . N . F . L . V G D V |
| PIV5 | I P T N V R Q . M Y Y T E A S S A F I V V K L M P T . |

Sequences for HMB3210

FIGURE 24A

VH.1 nucleotides gaggaacagctgctagagtctgggggaggcctggtcaagcctggggggtccctgagactctcct
gtgcagcctctggattcaccttcagtagttatagcatgaactgggtccgccaggctccagggaa
ggggctggagtgggtctcatccattagtgcaagtagcagttacagcgattacgcagactcagcg
aagggccgattcaccatctccagagacaacgccaagacctcactgtttctgcaaatgaacagcc
tgagagccgaggacacggctatctatttctgt**gcgagagctcgggcaactggctacagttccat
tacccctactttgacatttggggccagggaaccctggtcaccgtctcctcag VH.1 aminoacids EEQLLESGGGLVKPGGSLRLSCAASGFTFSSYSMNWVRQAPGKGLEWVSSISASSSYS**DYADSA
KGRFTISRDNAKTSLFLQMNSLRAEDTAIYFCARARATGYSSITPYFDIWGQGTLVTVSS VH.2 nucleotides gaggtgcagctggtggagtctgggggaggcctggtcaagcctggggggtccctgagactctcct
gtgcagcctctggattcaccttcagtagttatagcatgaactgggtccgccaggctccagggaa
ggggctggagtgggtctcatccattagtgcaagtagcagttacagcgattacgcagactcagcg
aagggccgattcaccatctccagagacaacgccaagacctcactgtttctgcaaatgaacagcc
tgagagccgaggacacggctatctatttctgt**gcgagagctcgggcaactggctacagttccat
tacccctactttgacatttggggccagggaaccctggtcaccgtctcctcag VH.2 aminoacids EVQLVESGGGLVKPGGSLRLSCAASGFTFSSYSMNWVRQAPGKGLEWVSSISASSSYS**DYADSA
KGRFTISRDNAKTSLFLQMNSLRAEDTAIYFCARARATGYSSITPYFDIWGQGTLVTVSS

FIGURE 24B

VL nucleotides cagtctgtcgtgacgcagacgccctcagtgtctggggccccagggcagagggtcaccatctcct
gcactgggagcagctccaacatcggggcaggttatgatgtacactggtaccagcaacttcagg
aacagccccaaactcctcatctatgataacaacaatcgaccctcagggatcccggaccgattc
tctgcctccaagtctggcacctcagcctcctggccatcaccgggctccaggctgaggatgagg
ctgattattactgccagtcctatgacaggaacctgagtggtgtcttcggaactgggaccaaggt
caccgtcctag VL aminoacids QSVVTQTPSVSGAPGQRVTISCTGSSSNIGAGYDVHWYQQLPGTAPKLLIYDNNNRPSGVPDRF
SASKSGTSASLAITGLQAEDEADYYCQSYDRNLSGVFGTGTKVTVL VL.3 nucleotides cagtctgtcgtgacgcagccgccctcagtgtctggggccccagggcagagggtcaccatctcct
gcactgggagcagctccaacatcggggcaggttatgatgtacactggtaccagcaacttcagg
aacagccccaaactcctcatctatgataacaacaatcgaccctcagggatcccggaccgattc
tctgcctccaagtctggcacctcagcctcctggccatcaccgggctccaggctgaggatgagg
ctgattattactgccagtcctatgacaggagcctgagtggtgtcttcggaactgggaccaaggt
caccgtcctag VL.3 aminoacids QSVVTQPPSVSGAPGQRVTISCTGSSSNIGAGYDVHWYQQLPGTAPKLLIYDNNNRPSGVPDRF
SASKSGTSASLAITGLQAEDEADYYCQSYDRSLSGVFGTGTKVTVL

gaggtgcagctggtggagagcggaggcggactggtcaaacctggcgggtcactgagactgtcat
gcgcagcaag cggcttcacattcagctcctactctatgaactgggtgcgacaggctcctggcaa
gggactggagtgggtctctagtatctcaagctcctctagttacatctactatgcagactccgtg
aagggaaggttcaccatctcacgcgataacgccaaaaatagcctgtatctgcagatgaattccc
tgagagccgaagacaccgctgtctactattgc**gcccgggctagagcaacaggctataacagcat
tactccttactttgacatc**tggggacagggcacactggtgaccgtctcctca

VH.3 (VH-GL)

EVQLVESGGGLVKPGGSLRLSCAASGFTFSSYSMNWVRQAPGKGLEWVSSISSSSSYIYYADSV
KGRFTISRDNAKNSLYLQMNSLRAEDTAVYYCARARATGYNSITPYFDIWGQGTLVTVSS

VL.4 (VL-GL)

Cagtccgtcgtcactcagcctccaagcgtcagcggggcacctgggcagcgggtcacaatctcat
gcactgggtcctcatccaacatcggcgctgggtacgacgtgcactggtatcagcagctgcctgg
aacagcacctaagctgctgatctacgggaacagcaatcggccatctggagtccccgatagattc
agcggatccaaatctggcaccagtgcctcactggctattacagggctgcaggcagaggacgaag
ccgattactattgccagtcttatgattcttctctgtctggagtcttcggcaccggcacaaaagt
caccgtcctg

VL.4 (VL-GL)

QSVVTQPPSVSGAPGQRVTISCTGSSSNIGAGYDVHWYQQLPGTAPKLLIYGNSNRPSGVPDRF
SGSKSGTSASLAITGLQAEDEADYYCQSYDSSLSGVFGTGTKVTVL

Sequences for HMB2430

FIGURE 25A

VH.1 nucleotides gaggtgcacctggtggagtctgggggaggcctggtcaagcctggggggtccctgagactctcct
gtgcagcctctggattcgcattcactggttatggtctaaattgggtccgccaggttccagggaa
gggcctggagtgggtttcatccatcactgctggaagctcatacatcgactacgcagagtcagtg
aagggccgattcaccatctccagagacaacggcaagaatacactgttcctgcaaatgagcgacc
tgagagccgacgacacggctgtctattactgt**gcgagagttgcgtctcctctggttcggggact
ccacttagactactggggccagggagccctggtcaccgtctcctcag VH.1 aminoacids EVHLVESGGGLVKPGGSLRLSCAASGFAFTGYGLNWVRQVPGKGLEWVSSITAGSSYI**DYAESV
KGRFTISRDNGKNTLFLQMSDLRADDTAVYYCARVASPLVRGLHLDYWGQGALVTVSS VH.2 nucleotides gaggtgcagctggtggagtctgggggaggcctggtcaagcctggggggtccctgagactctcct
gtgcagcctctggattcgcattcactggttatggtctaaattgggtccgccaggttccagggaa
gggcctggagtgggtttcatccatcactgctggaagctcatacatcgactacgcagagtcagtg
aagggccgattcaccatctccagagacaacggcaagaatacactgttcctgcaaatgagcgacc
tgagagccgacgacacggctgtctattactgt**gcgagagttgcgtctcctctggttcggggact
ccacttagactactggggccagggagccctggtcaccgtctcctcag VH.2 aminoacids EVQLVESGGGLVKPGGSLRLSCAASGFAFTGYGLNWVRQVPGKGLEWVSSITAGSSYI**DYAESV
KGRFTISRDNGKNTLFLQMSDLRADDTAVYYCARVASPLVRGLHLDYWGQGALVTVSS

FIGURE 25B

VL nucleotides cagtctgtgctgacgcagccgccctcaatgtccggggcccagggcagagggtcaccatctcct
gcactgggggcagctccaacatcggggcaggttatgatgtgcagtggtaccagcaacttccagg
agcagcccccaaactcctcatctatgctaacgacaatcggccctcaggggtccctgaccgattc
tctggctccaagtctggcacctcaggctccctagtcatcgctggcctccgggctgaggatgagg
ctgattattactgccagtcctatgaccgcaccctgagtgtagtgttcggcggagggaccaagct
gaccgtcctgg VL aminoacids QSVLTQPPSMSGAPGQRVTISCTGGSSNIGAYDVQWYQQLPGAAPKLLIYANDNRPSGVPDRF
SGSKSGTSGSLVIAGLRAEDEADYYCQSYDRTLSVVFGGGTKLTVL VH.3 (VH-GL) nucleotides gaagtgcagctggtggaatctggggggcgggctggtcaaacctggcggaagtctgaggctgtcct
gtgctgctagtggctttacctttagctcctactctatgaactgggtgcgacaggcacctggcaa
gggactggagtgggtctctagtatctcaagctcctcagttacatctactatgctgactccgtg
aagggccggttcaccatctcaagagataacgcaaaaaatagcctgtatctgcagatgaattcc
tgagggcagaagacacagccgtgtactattgc**gcccgcgtcgctagccctatggtgcgggggct
gcattttgattatggggacagggaactctggtgaccgtctcatcc VH.3 (VH-GL) aminoacids EVQLVESGGGLVKPGGSLRLSCAASGFTFSSYSMNWVRQAPGKGLEWVSSISSSSSYI**YYADSV
KGRFTISRDNAKNSLYLQMNSLRAEDTAVYYCARVASPMVRGLHFDYWGQGTLVTVSS VL.2 (VL-GL) nucleotides CAGAGCGTCCTGACCCAGCCACCATCCGTGAGCGGCGCACCCGGCCAGCGAGTGACTATTTCCT
GTACCGGCAGTTCTTCAAACATCGGCGCTGGGTACGACGTGCACTGGTATCAGCAGCTGCCTGG
AACAGCACCTAAGCTGCTGATCTACGGGAACAGCAATCGGCCATCTGGAGTCCCCGATAGATTC
AGCGGATCCAAATCTGGCACCAGTGCCTCACTGGCTATTACAGGGCTGCAGGCAGAGGACGAAG
CCGATTACTATTGCCAGAGCTACGATTCATCCCTGAGCGTGGTCTTCGGAGGCGGCACAAAACT
GACTGTCCTG VL.2 (VL-GL) aminoacids QSVLTQPPSVSGAPGQRVTISCTGSSSNIGAYDVHWYQQLPGTAPKLLIYGNSNRPSGVPDRF
SGSKSGTSASLAITGLQAEDEADYYCQSYDSSLSVVFGGGTKLTVL

SEQUENCE LISTING

```
<160> NUMBER OF SEQ ID NOS: 69

<210> SEQ ID NO 1
<211> LENGTH: 8
<212> TYPE: PRT
<213> ORGANISM: Homo sapiens

<400> SEQUENCE: 1

Gly Phe Thr Phe Ser Ser Tyr Ser
1               5

<210> SEQ ID NO 2
<211> LENGTH: 8
<212> TYPE: PRT
<213> ORGANISM: Homo sapiens

<400> SEQUENCE: 2

Ile Ser Ala Ser Ser Ser Tyr Ser
1               5

<210> SEQ ID NO 3
<211> LENGTH: 17
<212> TYPE: PRT
<213> ORGANISM: Homo sapiens

<400> SEQUENCE: 3

Ala Arg Ala Arg Ala Thr Gly Tyr Ser Ser Ile Thr Pro Tyr Phe Asp
1               5                   10                  15

Ile

<210> SEQ ID NO 4
<211> LENGTH: 9
<212> TYPE: PRT
<213> ORGANISM: Homo sapiens
```

```
<400> SEQUENCE: 4

Ser Ser Asn Ile Gly Ala Gly Tyr Asp
1               5

<210> SEQ ID NO 5
<211> LENGTH: 3
<212> TYPE: PRT
<213> ORGANISM: Homo sapiens

<400> SEQUENCE: 5

Asp Asn Asn
1

<210> SEQ ID NO 6
<211> LENGTH: 10
<212> TYPE: PRT
<213> ORGANISM: Homo sapiens

<400> SEQUENCE: 6

Gln Ser Tyr Asp Arg Asn Leu Ser Gly Val
1               5                   10

<210> SEQ ID NO 7
<211> LENGTH: 24
<212> TYPE: DNA
<213> ORGANISM: Homo sapiens

<400> SEQUENCE: 7 ggattcaccct tcagtagtta tagc                                           24

<210> SEQ ID NO 8
<211> LENGTH: 24
<212> TYPE: DNA
<213> ORGANISM: Homo sapiens

<400> SEQUENCE: 8
attagtgcaa gtagcagtta cagc                                            24

<210> SEQ ID NO 9
<211> LENGTH: 51
<212> TYPE: DNA
<213> ORGANISM: Homo sapiens

<400> SEQUENCE: 9
gcgagagctc gggcaactgg ctacagttcc attccccct actttgacat t              51

<210> SEQ ID NO 10
<211> LENGTH: 27
<212> TYPE: DNA
<213> ORGANISM: Homo sapiens

<400> SEQUENCE: 10
agctccaaca tcggggcagg ttatgat                                         27

<210> SEQ ID NO 11
<211> LENGTH: 9
<212> TYPE: DNA
<213> ORGANISM: Homo sapiens

<400> SEQUENCE: 11 gataacaac                                                              9
```

<210> SEQ ID NO 12
<211> LENGTH: 30
<212> TYPE: DNA
<213> ORGANISM: Homo sapiens

<400> SEQUENCE: 12
cagtcctatg acaggaacct gagtggtgtc                                      30

<210> SEQ ID NO 13
<211> LENGTH: 124
<212> TYPE: PRT
<213> ORGANISM: Homo sapiens

<400> SEQUENCE: 13

Glu Glu Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ala Ser Ser Tyr Ser Asp Tyr Ala Asp Ser Ala
    50                  55                  60

Lys Gly Arg Phe Thr Ile Ser Arg Asp Asn Ala Lys Thr Ser Leu Phe
65                  70                  75                  80

Leu Gln Met Asn Ser Leu Arg Ala Glu Asp Thr Ala Ile Tyr Phe Cys
                85                  90                  95

Ala Arg Ala Arg Ala Thr Gly Tyr Ser Ser Ile Thr Pro Tyr Phe Asp
            100                 105                 110

Ile Trp Gly Gln Gly Thr Leu Val Thr Val Ser Ser
        115                 120

<210> SEQ ID NO 14
<211> LENGTH: 110
<212> TYPE: PRT
<213> ORGANISM: Homo sapiens

<400> SEQUENCE: 14

Gln Ser Val Val Thr Gln Thr Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Asn Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Arg Asn
                85                  90                  95

Leu Ser Gly Val Phe Gly Thr Gly Thr Lys Val Thr Val Leu
            100                 105                 110

<210> SEQ ID NO 15
<211> LENGTH: 373
<212> TYPE: DNA
<213> ORGANISM: Homo sapiens

<400> SEQUENCE: 15
gaggaacagc tgctagagtc tgggggaggc ctggtcaagc ctggggggtc cctgagactc     60

```
tcctgtgcag cctctggatt caccttcagt agttatagca tgaactgggt ccgccaggct    120
ccagggaagg ggctggagtg ggtctcatcc attagtgcaa gtagcagtta cagcgattac    180
gcagactcag cgaagggccg attcaccatc tccagagaca acgccaagac ctcactgttt    240
ctgcaaatga acagcctgag agccgaggac acggctatct atttctgtgc gagagctcgg    300
gcaactggct acagttccat taccccctac tttgacattt ggggccaggg aaccctggtc    360
accgtctcct cag                                                       373
```

<210> SEQ ID NO 16
<211> LENGTH: 331
<212> TYPE: DNA
<213> ORGANISM: Homo sapiens

<400> SEQUENCE: 16

```
cagtctgtcg tgacgcagac gccctcagtg tctggggccc cagggcagag ggtcaccatc     60
tcctgcactg ggagcagctc caacatcggg gcaggttatg atgtacactg gtaccagcaa    120
cttccaggaa cagcccccaa actcctcatc tatgataaca caatcgacc ctcagggtc      180 ccggaccgat tctctgcctc caagtctggc acctcagcct ccctggccat caccgggctc    240
caggctgagg atgaggctga ttattactgc cagtcctatg acaggaacct gagtggtgtc    300
ttcggaactg ggaccaaggt caccgtccta g                                   331
```

<210> SEQ ID NO 17
<211> LENGTH: 124
<212> TYPE: PRT
<213> ORGANISM: Homo sapiens

<400> SEQUENCE: 17

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ala Ser Ser Tyr Ser Asp Tyr Ala Asp Ser Ala
    50                  55                  60

Lys Gly Arg Phe Thr Ile Ser Arg Asp Asn Ala Lys Thr Ser Leu Phe
65                  70                  75                  80

Leu Gln Met Asn Ser Leu Arg Ala Glu Asp Thr Ala Ile Tyr Phe Cys
                85                  90                  95

Ala Arg Ala Arg Ala Thr Gly Tyr Ser Ser Ile Thr Pro Tyr Phe Asp
            100                 105                 110

Ile Trp Gly Gln Gly Thr Leu Val Thr Val Ser Ser
        115                 120
```

<210> SEQ ID NO 18
<211> LENGTH: 373
<212> TYPE: DNA
<213> ORGANISM: Homo sapiens

<400> SEQUENCE: 18

```
gaggtgcagc tggtggagtc tgggggaggc ctggtcaagc ctgggggtc cctgagactc      60 tcctgtgcag cctctggatt caccttcagt agttatagca tgaactgggt ccgccaggct    120
ccagggaagg ggctggagtg ggtctcatcc attagtgcaa gtagcagtta cagcgattac    180
```

```
gcagactcag cgaagggccg attcaccatc tccagagaca acgccaagac ctcactgttt    240
ctgcaaatga acagcctgag agccgaggac acggctatct atttctgtgc gagagctcgg    300
gcaactggct acagttccat taccccctac tttgacattt ggggccaggg aaccctggtc    360
accgtctcct cag                                                      373
```

<210> SEQ ID NO 19
<211> LENGTH: 8
<212> TYPE: PRT
<213> ORGANISM: Homo sapiens

<400> SEQUENCE: 19

```
Gly Phe Ala Phe Thr Gly Tyr Gly
1               5
```

<210> SEQ ID NO 20
<211> LENGTH: 8
<212> TYPE: PRT
<213> ORGANISM: Homo sapiens

<400> SEQUENCE: 20

```
Ile Thr Ala Gly Ser Ser Tyr Ile
1               5
```

<210> SEQ ID NO 21
<211> LENGTH: 15
<212> TYPE: PRT
<213> ORGANISM: Homo sapiens

<400> SEQUENCE: 21

```
Ala Arg Val Ala Ser Pro Leu Val Arg Gly Leu His Leu Asp Tyr
1               5                   10                  15
```

<210> SEQ ID NO 22
<211> LENGTH: 3
<212> TYPE: PRT
<213> ORGANISM: Homo sapiens

<400> SEQUENCE: 22

```
Ala Asn Asp
1
```

<210> SEQ ID NO 23
<211> LENGTH: 10
<212> TYPE: PRT
<213> ORGANISM: Homo sapiens

<400> SEQUENCE: 23

```
Gln Ser Tyr Asp Arg Thr Leu Ser Val Val
1               5                   10
```

<210> SEQ ID NO 24
<211> LENGTH: 24
<212> TYPE: DNA
<213> ORGANISM: Homo sapiens

<400> SEQUENCE: 24

```
ggattcgcat tcactggtta tggt                                           24
```

<210> SEQ ID NO 25
<211> LENGTH: 24
<212> TYPE: DNA
<213> ORGANISM: Homo sapiens

```
<400> SEQUENCE: 25
atcactgctg gaagctcata catc                                          24

<210> SEQ ID NO 26
<211> LENGTH: 45
<212> TYPE: DNA
<213> ORGANISM: Homo sapiens

<400> SEQUENCE: 26
gcgagagttg cgtctcctct ggttcgggga ctccacttag actac                   45

<210> SEQ ID NO 27
<211> LENGTH: 9
<212> TYPE: DNA
<213> ORGANISM: Homo sapiens

<400> SEQUENCE: 27 gctaacgac                                                            9

<210> SEQ ID NO 28
<211> LENGTH: 30
<212> TYPE: DNA
<213> ORGANISM: Homo sapiens

<400> SEQUENCE: 28
cagtcctatg accgcaccct gagtgtagtg                                    30

<210> SEQ ID NO 29
<211> LENGTH: 122
<212> TYPE: PRT
<213> ORGANISM: Homo sapiens

<400> SEQUENCE: 29
```

Glu Val His Leu Val Glu Ser Gly Gly Gly Leu Val Lys Pro Gly Gly
1               5                   10                  15

Ser Leu Arg Leu Ser Cys Ala Ala Ser Gly Phe Ala Phe Thr Gly Tyr
            20                  25                  30

Gly Leu Asn Trp Val Arg Gln Val Pro Gly Lys Gly Leu Glu Trp Val
        35                  40                  45

Ser Ser Ile Thr Ala Gly Ser Ser Tyr Ile Asp Tyr Ala Glu Ser Val
    50                  55                  60

Lys Gly Arg Phe Thr Ile Ser Arg Asp Asn Lys Asn Thr Leu Phe
65                  70                  75                  80

Leu Gln Met Ser Asp Leu Arg Ala Asp Asp Thr Ala Val Tyr Tyr Cys
                85                  90                  95

Ala Arg Val Ala Ser Pro Leu Val Arg Gly Leu His Leu Asp Tyr Trp
            100                 105                 110

Gly Gln Gly Ala Leu Val Thr Val Ser Ser
        115                 120

```
<210> SEQ ID NO 30
<211> LENGTH: 110
<212> TYPE: PRT
<213> ORGANISM: Homo sapiens

<400> SEQUENCE: 30
```

Gln Ser Val Leu Thr Gln Pro Pro Ser Met Ser Gly Ala Pro Gly Gln
1               5                   10                  15

Arg Val Thr Ile Ser Cys Thr Gly Gly Ser Ser Asn Ile Gly Ala Gly
            20                  25                  30

Tyr Asp Val Gln Trp Tyr Gln Gln Leu Pro Gly Ala Ala Pro Lys Leu
            35                  40                  45

Leu Ile Tyr Ala Asn Asp Asn Arg Pro Ser Gly Val Pro Asp Arg Phe
        50                  55                  60

Ser Gly Ser Lys Ser Gly Thr Ser Gly Ser Leu Val Ile Ala Gly Leu
65                  70                  75                  80

Arg Ala Glu Asp Glu Ala Asp Tyr Tyr Cys Gln Ser Tyr Asp Arg Thr
                85                  90                  95

Leu Ser Val Val Phe Gly Gly Gly Thr Lys Leu Thr Val Leu
            100                 105                 110

<210> SEQ ID NO 31
<211> LENGTH: 367
<212> TYPE: DNA
<213> ORGANISM: Homo sapiens

<400> SEQUENCE: 31
gaggtgcacc tggtggagtc tgggggaggc ctggtcaagc ctgggggggtc cctgagactc    60 tcctgtgcag cctctggatt cgcattcact ggttatggtc taaattgggt ccgccaggtt   120
ccagggaagg gcctggagtg ggtttcatcc atcactgctg gaagctcata catcgactac   180
gcagagtcag tgaagggccg attcaccatc tccagagaca acggcaagaa tacactgttc   240
ctgcaaatga gcgacctgag agccgacgac acggctgtct attactgtgc gagagttgcg   300
tctcctctgg ttcggggact ccacttagac tactggggcc agggagccct ggtcaccgtc   360
tcctcag                                                            367

<210> SEQ ID NO 32
<211> LENGTH: 331
<212> TYPE: DNA
<213> ORGANISM: Homo sapiens

<400> SEQUENCE: 32
cagtctgtgc tgacgcagcc gccctcaatg tccggggccc cagggcagag ggtcaccatc    60
tcctgcactg ggggcagctc caacatcggg gcaggttatg atgtgcagtg gtaccagcaa   120
cttccaggag cagccccaa actcctcatc tatgctaacg acaatcggcc ctcaggggtc   180
cctgaccgat tctctggctc caagtctggc acctcaggct ccctagtcat cgctggcctc   240
cgggctgagg atgaggctga ttattactgc cagtcctatg accgcaccct gagtgtagtg   300
ttcggcggag ggaccaagct gaccgtcctg g                                  331

<210> SEQ ID NO 33
<211> LENGTH: 122
<212> TYPE: PRT
<213> ORGANISM: Homo sapiens

<400> SEQUENCE: 33

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Thr Gly Tyr
            20                  25                  30

Gly Leu Asn Trp Val Arg Gln Val Pro Gly Lys Gly Leu Glu Trp Val
        35                  40                  45

Ser Ser Ile Thr Ala Gly Ser Ser Tyr Ile Asp Tyr Ala Glu Ser Val
    50                  55                  60

Lys Gly Arg Phe Thr Ile Ser Arg Asp Asn Gly Lys Asn Thr Leu Phe

```
                65                  70                  75                  80
Leu Gln Met Ser Asp Leu Arg Ala Asp Asp Thr Ala Val Tyr Tyr Cys
                    85                  90                  95

Ala Arg Val Ala Ser Pro Leu Val Arg Gly Leu His Leu Asp Tyr Trp
            100                 105                 110

Gly Gln Gly Ala Leu Val Thr Val Ser Ser
        115                 120
```

<210> SEQ ID NO 34
<211> LENGTH: 367
<212> TYPE: DNA
<213> ORGANISM: Homo sapiens

<400> SEQUENCE: 34

```
gaggtgcagc tggtggagtc tgggggaggc ctggtcaagc ctgggggtc cctgagactc      60
tcctgtgcag cctctggatt cgcattcact ggttatggtc taaattgggt ccgccaggtt    120
ccagggaagg gctggagtg gtttcatcc atcactgctg gaagctcata catcgactac      180
gcagagtcag tgaagggccg attcaccatc tccagagaca acggcaagaa tacactgttc    240
ctgcaaatga gcgacctgag agccgacgac acggctgtct attactgtgc gagagttgcg    300
tctcctctgg ttcggggact ccacttagac tactggggcc agggagccct ggtcaccgtc    360
tcctcag                                                              367
```

<210> SEQ ID NO 35
<211> LENGTH: 10
<212> TYPE: PRT
<213> ORGANISM: Homo sapiens

<400> SEQUENCE: 35

```
Gln Ser Tyr Asp Arg Ser Leu Ser Gly Val
1               5                   10
```

<210> SEQ ID NO 36
<211> LENGTH: 30
<212> TYPE: DNA
<213> ORGANISM: Homo sapiens

<400> SEQUENCE: 36

```
cagtcctatg acaggagcct gagtggtgtc                                      30
```

<210> SEQ ID NO 37
<211> LENGTH: 110
<212> TYPE: PRT
<213> ORGANISM: Homo sapiens

<400> SEQUENCE: 37

```
Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Asn Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Tyr Asp Arg Ser
                85                  90                  95
```

```
Leu Ser Gly Val Phe Gly Thr Gly Thr Lys Val Thr Val Leu
            100                 105                 110
```

<210> SEQ ID NO 38
<211> LENGTH: 331
<212> TYPE: DNA
<213> ORGANISM: Homo sapiens

<400> SEQUENCE: 38

```
cagtctgtcg tgacgcagcc gccctcagtg tctggggccc cagggcagag ggtcaccatc      60
tcctgcactg ggagcagctc caacatcggg gcaggttatg atgtacactg gtaccagcaa     120
cttccaggaa cagcccccaa actcctcatc tatgataaca acaatcgacc ctcagggggtc    180 ccggaccgat tctctgcctc caagtctggc acctcagcct ccctggccat caccgggctc     240
caggctgagg atgaggctga ttattactgc cagtcctatg acaggagcct gagtggtgtc     300
ttcggaactg ggaccaaggt caccgtccta g                                    331
```

<210> SEQ ID NO 39
<211> LENGTH: 8
<212> TYPE: PRT
<213> ORGANISM: Homo sapiens

<400> SEQUENCE: 39

```
Ile Ser Ser Ser Ser Ser Tyr Ile
1               5
```

<210> SEQ ID NO 40
<211> LENGTH: 17
<212> TYPE: PRT
<213> ORGANISM: Homo sapiens

<400> SEQUENCE: 40

```
Ala Arg Ala Arg Ala Thr Gly Tyr Asn Ser Ile Thr Pro Tyr Phe Asp
1               5                   10                  15

Ile
```

<210> SEQ ID NO 41
<211> LENGTH: 3
<212> TYPE: PRT
<213> ORGANISM: Homo sapiens

<400> SEQUENCE: 41

```
Gly Asn Ser
1
```

<210> SEQ ID NO 42
<211> LENGTH: 10
<212> TYPE: PRT
<213> ORGANISM: Homo sapiens

<400> SEQUENCE: 42

```
Gln Ser Tyr Asp Ser Ser Leu Ser Gly Val
1               5                   10
```

<210> SEQ ID NO 43
<211> LENGTH: 24
<212> TYPE: DNA
<213> ORGANISM: Homo sapiens

<400> SEQUENCE: 43

```
ggcttcacat tcagctccta ctct                                             24
```

<210> SEQ ID NO 44
<211> LENGTH: 24
<212> TYPE: DNA
<213> ORGANISM: Homo sapiens

<400> SEQUENCE: 44
atctcaagct cctctagtta catc                                    24

<210> SEQ ID NO 45
<211> LENGTH: 51
<212> TYPE: DNA
<213> ORGANISM: Homo sapiens

<400> SEQUENCE: 45
gcccgggcta gagcaacagg ctataacagc attactcctt actttgacat c       51

<210> SEQ ID NO 46
<211> LENGTH: 15
<212> TYPE: DNA
<213> ORGANISM: Homo sapiens

<400> SEQUENCE: 46
tcatccaaca tcggc                                              15

<210> SEQ ID NO 47
<211> LENGTH: 9
<212> TYPE: DNA
<213> ORGANISM: Homo sapiens

<400> SEQUENCE: 47 gggaacagc                                                      9

<210> SEQ ID NO 48
<211> LENGTH: 30
<212> TYPE: DNA
<213> ORGANISM: Homo sapiens

<400> SEQUENCE: 48
cagtcttatg attcttctct gtctggagtc                              30

<210> SEQ ID NO 49
<211> LENGTH: 124
<212> TYPE: PRT
<213> ORGANISM: Homo sapiens

<400> SEQUENCE: 49

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Arg Ala Thr Gly Tyr Asn Ser Ile Thr Pro Tyr Phe Asp
            100                 105                 110

Ile Trp Gly Gln Gly Thr Leu Val Thr Val Ser Ser
        115                 120

<210> SEQ ID NO 50
<211> LENGTH: 110
<212> TYPE: PRT
<213> ORGANISM: Homo sapiens

<400> SEQUENCE: 50

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Val Phe Gly Thr Gly Thr Lys Val Thr Val Leu
            100                 105                 110

<210> SEQ ID NO 51
<211> LENGTH: 372
<212> TYPE: DNA
<213> ORGANISM: Homo sapiens

<400> SEQUENCE: 51
gaggtgcagc tggtggagag cggaggcgga ctggtcaaac ctggcgggtc actgagactg      60
tcatgcgcag caagcggctt cacattcagc tcctactcta tgaactgggt gcgacaggct     120
cctggcaagg gactggagtg ggtctctagt atctcaagct cctctagtta catctactat     180
gcagactccg tgaagggaag gttcaccatc tcacgcgata cgccaaaaaa tagcctgtat     240
ctgcagatga attccctgag agccgaagac accgctgtct actattgcgc ccgggctaga     300
gcaacaggct ataacagcat tactccttac tttgacatct ggggacaggg cacactggtg     360
accgtctcct ca                                                         372

<210> SEQ ID NO 52
<211> LENGTH: 330
<212> TYPE: DNA
<213> ORGANISM: Homo sapiens

<400> SEQUENCE: 52
cagtccgtcg tcactcagcc tccaagcgtc agcggggcac ctgggcagcg ggtcacaatc      60
tcatgcactg gtcctcatc caacatcggc gctgggtacg acgtgcactg gtatcagcag     120
ctgcctggaa cagcacctaa gctgctgatc tacgggaaca gcaatcggcc atctggagtc     180
cccgatagat tcagcggatc caaatctggc accagtgcct cactggctat tacagggctg     240
caggcagagg acgaagccga ttactattgc agtctttatg attcttctct gtctggagtc     300
ttcggcaccg gcacaaaagt caccgtcctg                                      330

<210> SEQ ID NO 53
<211> LENGTH: 15
<212> TYPE: PRT

<213> ORGANISM: Homo sapiens

<400> SEQUENCE: 53

Ala Arg Val Ala Ser Pro Met Val Arg Gly Leu His Phe Asp Tyr
1               5                   10                  15

<210> SEQ ID NO 54
<211> LENGTH: 10
<212> TYPE: PRT
<213> ORGANISM: Homo sapiens

<400> SEQUENCE: 54

Gln Ser Tyr Asp Ser Ser Leu Ser Val Val
1               5                   10

<210> SEQ ID NO 55
<211> LENGTH: 24
<212> TYPE: DNA
<213> ORGANISM: Homo sapiens

<400> SEQUENCE: 55
ggctttacct ttagctccta ctct                                    24

<210> SEQ ID NO 56
<211> LENGTH: 45
<212> TYPE: DNA
<213> ORGANISM: Homo sapiens

<400> SEQUENCE: 56
gcccgcgtcg ctagccctat ggtgcggggg ctgcattttg attat             45

<210> SEQ ID NO 57
<211> LENGTH: 27
<212> TYPE: DNA
<213> ORGANISM: Homo sapiens

<400> SEQUENCE: 57
tcttcaaaca tcggcgctgg gtacgac                                 27

<210> SEQ ID NO 58
<211> LENGTH: 30
<212> TYPE: DNA
<213> ORGANISM: Homo sapiens

<400> SEQUENCE: 58
cagagctacg attcatccct gagcgtggtc                              30

<210> SEQ ID NO 59
<211> LENGTH: 122
<212> TYPE: PRT
<213> ORGANISM: Homo sapiens

<400> SEQUENCE: 59

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr

```
                 65                  70                  75                  80
Leu Gln Met Asn Ser Leu Arg Ala Glu Asp Thr Ala Val Tyr Tyr Cys
                         85                  90                  95

Ala Arg Val Ala Ser Pro Met Val Arg Gly Leu His Phe Asp Tyr Trp
            100                 105                 110

Gly Gln Gly Thr Leu Val Thr Val Ser Ser
            115                 120
```

<210> SEQ ID NO 60
<211> LENGTH: 110
<212> TYPE: PRT
<213> ORGANISM: Homo sapiens

<400> SEQUENCE: 60

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Val Val Phe Gly Gly Gly Thr Lys Leu Thr Val Leu
            100                 105                 110
```

<210> SEQ ID NO 61
<211> LENGTH: 366
<212> TYPE: DNA
<213> ORGANISM: Homo sapiens

<400> SEQUENCE: 61

```
gaagtgcagc tggtggaatc tgggggcggg ctggtcaaac ctggcggaag tctgaggctg      60
tcctgtgctg ctagtggctt tacctttagc tcctactcta tgaactgggt gcgacaggca     120
cctggcaagg gactggagtg ggtctctagt atctcaagct cctctagtta catctactat     180
gctgactccg tgaagggccg gttcaccatc tcaagagata cgcaaaaaa tagcctgtat     240 ctgcagatga attccctgag gcagaagac acagccgtgt actattgcgc ccgcgtcgct    300
agccctatgg tgcggggct gcattttgat tattgggac agggaactct ggtgaccgtc     360
tcatcc                                                               366
```

<210> SEQ ID NO 62
<211> LENGTH: 330
<212> TYPE: DNA
<213> ORGANISM: Homo sapiens

<400> SEQUENCE: 62

```
cagagcgtcc tgacccagcc accatccgtg agcggcgcac ccggccagcg agtgactatt      60
tcctgtaccg gcagttcttc aaacatcggc gctgggtacg acgtgcactg gtatcagcag    120
ctgcctggaa cagcacctaa gctgctgatc tacgggaaca gcaatcggcc atctggagtc    180
cccgatagat tcagcggatc caaatctggc accagtgcct cactggctat tacagggctg    240
caggcagagg acgaagccga ttactattgc cagagctacg attcatccct gagcgtggtc    300
```
ttcggaggcg gcacaaaact gactgtcctg 330

<210> SEQ ID NO 63
<211> LENGTH: 21
<212> TYPE: PRT
<213> ORGANISM: Homo sapiens

<400> SEQUENCE: 63

Ser Ala Val Ser Lys Gly Tyr Leu Ser Ala Leu Arg Thr Gly Trp Tyr
1               5                   10                  15

Thr Ser Val Ile Thr
            20

<210> SEQ ID NO 64
<211> LENGTH: 9
<212> TYPE: PRT
<213> ORGANISM: Homo sapiens

<400> SEQUENCE: 64

Tyr Leu Ser Ala Leu Arg Thr Gly Trp
1               5

<210> SEQ ID NO 65
<211> LENGTH: 9
<212> TYPE: PRT
<213> ORGANISM: Homo sapiens

<400> SEQUENCE: 65

Tyr Leu Ser Val Leu Arg Thr Gly Trp
1               5

<210> SEQ ID NO 66
<211> LENGTH: 9
<212> TYPE: PRT
<213> ORGANISM: Homo sapiens

<400> SEQUENCE: 66

Tyr Phe Ser Ala Leu Arg Thr Gly Trp
1               5

<210> SEQ ID NO 67
<211> LENGTH: 9
<212> TYPE: PRT
<213> ORGANISM: Homo sapiens

<400> SEQUENCE: 67

Tyr Phe Ser Val Leu Arg Thr Gly Trp
1               5

<210> SEQ ID NO 68
<211> LENGTH: 9
<212> TYPE: PRT
<213> ORGANISM: Homo sapiens

<400> SEQUENCE: 68

Tyr Lys Ser Ala Leu Arg Thr Gly Trp
1               5

<210> SEQ ID NO 69
<211> LENGTH: 9
<212> TYPE: PRT
<213> ORGANISM: Homo sapiens

<400> SEQUENCE: 69

Tyr Lys Ser Val Leu Arg Thr Gly Trp
1               5

ANTIBODIES THAT NEUTRALIZE RSV, MPV AND PVM AND USES THEREOF

This application claims the benefit of priority of U.S. provisional Application No. 61/613,197, filed Mar. 20, 2012, and U.S. provisional Application No. 61/655,310, filed Jun. 4, 2012, the disclosures of which are hereby incorporated by reference, as if written herein, in their entireties.

BACKGROUND

Respiratory Syncytial Virus (RSV) and Metapneumovirus (MPV) and Pneumonia Virus of mice are common cold viruses belonging to the family of paramyxovirus that share target population and represent a major health problem in newborns and immunocompromised patients.

RSV is the major cause of acute respiratory tract disease in infants and adults across the globe. Between 0.5% and 3.2% of children with RSV infection require hospitalization (Thompson, W. W. et al., 2003, JAMA: *The Journal of the American Medical Association* 289:179-186), and 5% to 10% of children have prolonged severe infection, a factor believed to be predisposing to wheezing and asthma-like symptoms later in childhood. Immunity to RSV appears to be short-lived, thus re-infections are frequent (Ogra, 2003, *Paediatric Respiratory Reviews* 5 Suppl A:S119-126).

The human MPV was isolated for the first time in 2001 and is now recognized to be the second major cause of acute respiratory tract disease in infants and adults; it is estimated that it infects over 50% of infants by two years of age and almost all children by five years. MPV accounts for roughly 5 to 15% of respiratory disease in hospitalized young children (Alto, 2004, *The Journal of the American Board of Family Practice/American Board of Family Practice* 17:466-469; Williams et al., 2004, *N Engl J Med* 350:443-450). Infection with MPV is a significant burden of disease in at-risk premature infants, chronic lung disease of prematurity, congestive heart disease, and immunodeficiency (Martino et al., 2005, *Biology of Blood and Marrow Transplantation: Journal of the American Society for Blood and Marrow Transplantation* 11:781-796).

Co-infections with MPV and RSV may be common given their prevalence and overlapping winter epidemics. Although it is unclear whether synergistic pathology can occur between these two viruses, exacerbations leading to particularly severe respiratory tract disease were observed in some children co-infected with MPV and RSV (Greensill, 2003, *Emerging Infectious Diseases* 9:372).

RSV, which belongs to the Pneumovirus genus of the subfamily Pneumoviriniae, and MPV, which belongs to the Metapneumovirus genus of the subfamily Pneumoviriniae, have some similarities in their genetic structure, though MPV lacks the non-structural genes NS1 and NS2 found in RSV. The RSV and MPV envelopes contain three virally encoded transmembrane surface glycoproteins: the major attachment protein G, the fusion protein F, and the small hydrophobic SH protein. Although the RSV and MPV envelopes contain proteins that are functionally similar, it is important to note, however, that the F proteins of RSV and MPV share only 33% amino acid sequence identity. Further, antisera generated against either RSV or MPV do not cross-neutralize both viruses (Wyde et al., 2003, *Antiviral Research* 60:51-59) and so far no monoclonal antibodies have been isolated that are able to cross-neutralize both RSV and MPV.

The RSV and MPV F glycoproteins direct viral penetration by fusion between the virion envelope and the host cell plasma membrane. Later in infection, F protein expressed on the cell surface can mediate fusion with neighboring cells to form syncytia (Collins et al., 1984 *PNAS* 81:7683-7687). In both cases, the N-terminus of the F subunit that is created by proteolytic cleavage and contains hydrophobic stretch of amino acids, called the fusion peptide, inserts directly into the target membrane to initiate fusion. After binding to the target cell and subsequent activation, the metastable prefusion F protein undergoes a series of structural rearrangements that result in the insertion of the fusion peptide into the target cell membrane, followed by the formation of a stable helical bundle that forms as the viral and cell membranes are apposed. These structural changes lead to the formation of a stable post-fusion F protein.

Vaccines for RSV or MPV infection are currently not available. A formalin-inactivated and alum-adjuvanted RSV vaccine (FI-RSV) tested in the 1960s was found to predispose infants for enhanced disease following natural RSV infection leading to high fever and severe pneumonia, resulting in high hospitalization rates and even some fatalities (Fulginiti et al., 1969, *American Journal of Epidemiology* 89:435-448; Kapikian et al., 1969, *American Journal of Epidemiology* 89:405-421; Kim et al., 1969, *American Journal of Epidemiology* 89:422-434). Similarly, formalin-inactivated MPV vaccines showed immune-mediated enhanced disease in young cynomolgus macaques (de Swart et al., 2007, *Vaccine* 25:8518-8528). Further, antiviral therapies such as Ribavirin have not been proven to be effective in RSV or MPV infection.

Evidence for the role of serum antibodies in protection against RSV virus has emerged from epidemiological as well as animal studies. In infants, titers of maternally transmitted antibodies correlate with resistance to serious disease (Glezen et al., 1981, *The Journal of Pediatrics* 98:708-715) and in adults incidence and severity of lower respiratory tract involvement is diminished in the presence of high levels of serum RSV neutralizing antibodies (McIntosh et al., 1978, *The Journal of Infectious Diseases* 138:24-32). A monoclonal antibody, Palivizumab (Synagis), is registered for the prevention of RSV infection in premature newborns. Palivizumab, however, is not always effective in preventing RSV infection and is not effective therapeutically. Further, prolonged pulmonary replication of RSV in the presence of Palivizumab is followed in animals by the appearance of resistant virus strains (Zhao and Sullender, 2005, *Journal of Virology* 79:3962-3968). Currently there are no monoclonal antibodies for the treatment or prevention of MPV infection.

The lack of a good working animal model for the most severe forms of RSV infection is related to the fact that RSV and MPV are host-restricted Pneumovirus pathogens. The development of new drugs for the therapy of RSV and MPV infections has been hampered by the lack of an animal model able to recapitulate all the symptoms and severity of the human disease. Indeed, RSV and MPV are not a natural mouse pathogen and induce only a limited, minimally symptomatic, and rapidly aborted primary infection in response to a massive, non-physiologic inoculum of the virus. Pneumonia virus of mice (PVM) is a natural rodent Pneumovirus pathogen which belongs to the same family, subfamily and genus (Pneumovirus) of human and bovine RSV. The PVM F protein shares only 40% amino acid identity with human RSV F protein, but has the same genetic organization with the exception of the M2-L overlap which is present in RSV but absent in PVM. The infection by the natural mouse pathogen PVM replicates many of the signs and symptoms of the most severe forms of RSV as it occurs in human infants. PVM infection is characterized by rapid virus replication accompanied by a massive inflammatory response that leads to respiratory failure and death (Rosemberg and Domachowske, 2008, *Immunology Letter* 118:6-12). PVM infection in mice is therefore considered to be the most relevant animal model of RSV and MPV severe infections of humans.

The lack of preventive treatment for MPV infection and of vaccines against RSV and MPV infections as well as the therapeutic inefficacy of Palivizumab, highlight the need for new preventive and therapeutic agents against these prominent human pathogens. Given the large prevalence and the possibility of co-infection, it would be highly desirable to have a single agent that is capable of preventing as well as treating or attenuating both RSV and MPV infection and to have an animal model in which to test the agent. Therefore, there is a need for broadly cross-reactive neutralising antibodies that protect against a wide range of paramyxoviruses, for example, at least RSV and MPV, and preferably RSV, MPV and PVM.

SUMMARY

The invention is based, in part, on the discovery of broadly neutralizing antibodies that neutralize infection of RSV, MPV, and PVM, as well as polypeptides to which the antibodies of the invention bind. Accordingly, in one aspect of the invention, the invention comprises an isolated antibody, for example a monoclonal antibody, a human antibody, a human monoclonal antibody, an antibody variant, or an antigen binding fragment, that cross-neutralizes infection of RSV, MPV, and PVM.

In one embodiment of the invention, the invention comprises an isolated antibody, or an antigen binding fragment thereof, that neutralizes infection of both RSV and MPV. In another embodiment of the invention, the invention comprises an antibody, or an antigen binding fragment thereof, that neutralizes infection of RSV, MPV, and PVM.

In another embodiment of the invention, the invention comprises an isolated antibody, or an antigen binding fragment thereof, that specifically binds RSV pre-fusion F protein and not RSV post-fusion F protein. In yet another embodiment, the invention comprises an isolated antibody, or an antigen binding fragment thereof, that specifically binds the pre-fusion F protein and not the post-fusion F protein of RSV and MPV. In yet another embodiment, the invention comprises an isolated antibody, or an antigen binding fragment thereof, that specifically binds the pre-fusion F protein and not the post-fusion F protein of RSV, MPV and PVM.

In another embodiment of the invention, the invention comprises an antibody, or an antigen binding fragment thereof, comprising at least one complementarity determining region (CDR) sequence having at least 95% sequence identity to any one of SEQ ID NOs: 1-6, 19-23, 35, 39-42, or 53-54 wherein the antibody neutralizes infection of RSV, MPV, and PVM.

In another embodiment of the invention, the invention comprises an antibody or antigen binding fragment thereof, comprising a heavy chain CDR1 with the amino acid sequence of SEQ ID NO: 1 or SEQ ID NO: 19; a heavy chain CDR2 with the amino acid sequence of SEQ ID NO: 2, SEQ ID NO: 20 or SEQ ID NO: 39; and a heavy chain CDR3 with the amino acid sequence of SEQ ID NO: 3, SEQ ID NO: 21, SEQ ID NO: 40 or SEQ ID NO: 53, wherein the antibody neutralizes infection of RSV, MPV, and PVM. In another embodiment of the invention, the invention comprises an antibody, or an antigen binding fragment thereof, comprising a light chain CDR1 with the amino acid sequence of SEQ ID NO: 4; a light chain CDR2 with the amino acid sequence of SEQ ID NO: 5, SEQ ID NO: 22 or SEQ ID NO: 41; and a light chain CDR3 with the amino acid sequence of SEQ ID NO: 6, SEQ ID NO: 23, SEQ ID NO: 35, SEQ ID NO: 42 or SEQ ID NO: 54, wherein the antibody neutralizes infection of RSV, MPV, and PVM.

In yet another embodiment of the invention, the invention comprises an antibody, or an antigen binding fragment thereof, wherein the antibody comprises: (i) the heavy chain CDR1, CDR2, and CDR3 sequences as set forth in SEQ ID NO: 1, SEQ ID NO: 2, and SEQ ID NO: 3, respectively, and the light chain CDR1, CDR2, and CDR3 sequences as set forth in SEQ ID NO: 4, SEQ ID NO: 5, and SEQ ID NO: 35, respectively; (ii) the heavy chain CDR1, CDR2, and CDR3 sequences as set forth in SEQ ID NO: 1, SEQ ID NO: 2, and SEQ ID NO: 3, respectively, and the light chain CDR1, CDR2, and CDR3 sequences as set forth in SEQ ID NO: 4, SEQ ID NO: 5, and SEQ ID NO: 6, respectively; (iii) the heavy chain CDR1, CDR2, and CDR3 sequences as set forth in SEQ ID NO: 1, SEQ ID NO: 39, and SEQ ID NO: 40, respectively, and the light chain CDR1, CDR2, and CDR3 sequences as set forth in SEQ ID NO: 4, SEQ ID NO: 41, and SEQ ID NO: 42, respectively (iv) the heavy chain CDR1, CDR2, and CDR3 sequences as set forth in SEQ ID NO: 1, SEQ ID NO: 39, and SEQ ID NO: 40, respectively, and the light chain CDR1, CDR2, and CDR3 sequences as set forth in SEQ ID NO: 4, SEQ ID NO: 5, and SEQ ID NO: 6, respectively; (v) the heavy chain CDR1, CDR2, and CDR3 sequences as set forth in SEQ ID NO: 1, SEQ ID NO: 2, and SEQ ID NO: 3, respectively, and the light chain CDR1, CDR2, and CDR3 sequences as set forth in SEQ ID NO: 4, SEQ ID NO: 41, and SEQ ID NO: 42, respectively, and wherein the antibody neutralizes infection of RSV, MPV, and PVM.

In yet another embodiment of the invention, the invention comprises an antibody, or an antigen binding fragment thereof, wherein the antibody comprises: (i) the heavy chain CDR1, CDR2, and CDR3 sequences as set forth in SEQ ID NO: 19, SEQ ID NO: 20, and SEQ ID NO: 21, respectively, and the light chain CDR1, CDR2, and CDR3 sequences as set forth in SEQ ID NO: 4, SEQ ID NO: 22, and SEQ ID NO: 23, respectively; (ii) the heavy chain CDR1, CDR2, and CDR3 sequences as set forth in SEQ ID NO: 1, SEQ ID NO: 39, and SEQ ID NO: 53, respectively, and the light chain CDR1, CDR2, and CDR3 sequences as set forth in SEQ ID NO: 4, SEQ ID NO: 41, and SEQ ID NO: 54, respectively; (iii) the heavy chain CDR1, CDR2, and CDR3 sequences as set forth in SEQ ID NO: 1, SEQ ID NO: 39, and SEQ ID NO: 53, respectively, and the light chain CDR1, CDR2, and CDR3 sequences as set forth in SEQ ID NO: 4, SEQ ID NO: 22, and SEQ ID NO: 23, respectively; or (iv) the heavy chain CDR1, CDR2, and CDR3 sequences as set forth in SEQ ID NO: 19, SEQ ID NO: 20, and SEQ ID NO: 21, respectively, and the light chain CDR1, CDR2, and CDR3 sequences as set forth in SEQ ID NO: 4, SEQ ID NO: 41, and SEQ ID NO: 54, respectively, and wherein the antibody neutralizes infection of RSV, MPV, and PVM.

In yet another embodiment of the invention, the invention comprises an antibody, or an antigen binding fragment thereof, wherein the antibody comprises a heavy chain variable region comprising the amino acid sequence of SEQ ID NO: 17 and a light chain variable region comprising the amino acid sequence of SEQ ID NO: 37; or a heavy chain variable region comprising the amino acid sequence of SEQ ID NO: 13 and a light chain variable region comprising the amino acid sequence of SEQ ID NO: 14; or a heavy chain variable region comprising the amino acid sequence of SEQ ID NO: 17 and a light chain variable region comprising the amino acid sequence of SEQ ID NO: 14; or a heavy chain variable region comprising the amino acid sequence of SEQ ID NO: 49 and a light chain variable region comprising the amino acid sequence of SEQ ID NO: 50; or a heavy chain variable region comprising the amino acid sequence of SEQ ID NO: 49 and a light chain variable region comprising the amino acid sequence of SEQ ID NO: 14; or a heavy chain variable region comprising the amino acid sequence of SEQ ID NO: 17 and a light chain variable region comprising the amino acid sequence of SEQ ID NO: 50, and wherein the antibody neutralizes infection of RSV, MPV, and PVM.

In yet another embodiment of the invention, the invention comprises an antibody, or an antigen binding fragment thereof, wherein the antibody comprises a heavy chain variable region comprising the amino acid sequence of SEQ ID NO: 29 and a light chain variable region comprising the amino acid sequence of SEQ ID NO: 30; or a heavy chain variable region comprising the amino acid sequence of SEQ ID NO: 33 and a light chain variable region comprising the amino acid sequence of SEQ ID NO: 30 or a heavy chain variable region comprising the amino acid sequence of SEQ ID NO: 59 and a light chain variable region comprising the amino acid sequence of SEQ ID NO: 60; or a heavy chain variable region comprising the amino acid sequence of SEQ ID NO: 59 and a light chain variable region comprising the amino acid sequence of SEQ ID NO: 30; or a heavy chain variable region comprising the amino acid sequence of SEQ ID NO: 33 and a light chain variable region comprising the amino acid sequence of SEQ ID NO: 60, and wherein the antibody neutralizes infection of RSV, MPV, and PVM.

The invention further comprises an antibody, or an antigen binding fragment thereof, described herein as HMB3210 (or 3210); or HMB2430 (or 2430). In another embodiment, the invention comprises an antibody, or antigen binding fragment thereof, that neutralizes infection of RSV, MPV, and PVM, wherein the antibody or fragment thereof is expressed by an immortalized B cell clone that produces HMB3210 or HMB2430.

In another aspect, the invention comprises a nucleic acid molecule comprising a polynucleotide encoding an antibody or antibody fragment of the invention. In yet another aspect, the invention comprises a vector comprising a nucleic acid molecule of the invention. The invention also comprises a cell that expresses an antibody of the invention or an antigen binding fragment thereof. In still another aspect, the invention comprises an isolated or purified immunogenic polypeptide comprising an epitope that binds to an antibody or antigen binding fragment of the invention.

The invention further comprises a pharmaceutical composition comprising an antibody of the invention or an antigen binding fragment thereof, a nucleic acid molecule of the invention, a vector comprising a nucleic acid molecule of the invention, a cell expressing an antibody or an antibody fragment of the invention, or an immunogenic polypeptide of the invention, and a pharmaceutically acceptable diluent or carrier. The invention also comprises a pharmaceutical composition comprising a first antibody or an antigen binding fragment thereof, and a second antibody, or an antigen binding fragment thereof, wherein the first antibody is an antibody of the invention, and the second antibody is an antibody, or an antigen binding fragment thereof, that neutralizes infection of RSV or MPV or both RSV and MPV, or all three of RSV, MPV, and PVM.

Use of an antibody of the invention, or an antigen binding fragment thereof, a nucleic acid of the invention, a vector comprising a nucleic acid of the invention, a cell expressing a vector of the invention, an isolated or purified immunogenic polypeptide comprising an epitope that binds to an antibody or antibody fragment of the invention, or a pharmaceutical composition of the invention (i) in the manufacture of a medicament for the treatment or attenuation of RSV or MPV or both RSV and MPV co-infection, (ii) in a vaccine, or (iii) in diagnosis of RSV and/or MPV virus infection is also contemplated to be within the scope of the invention. Further, use of an antibody of the invention, or an antigen binding fragment thereof, for monitoring the quality of a vaccine against RSV or MPV or both RSV and MPV by checking that the antigen of said vaccine contains the specific epitope in the correct conformation is also contemplated to be within the scope of the invention.

In another aspect, the invention comprises a method of treating or attenuating RSV and MPV infection or lowering the risk of RSV and MPV infection comprising administering to a subject in need thereof, a therapeutically effective amount of an antibody or an antigen binding antibody fragment of the invention.

In a further aspect, the invention comprises a polypeptide which specifically binds to an antibody of the invention, or an antigen binding fragment thereof, for use (i) in therapy, (ii) in the manufacture of a medicament for the treatment or attenuation of RSV or MPV or both RSV and MPV infection, (iii) as a vaccine, or (iv) in screening for ligands able to neutralise infection of RSV or MPV or both RSV and MPV.

DESCRIPTION OF FIGURES

FIG. 21 shows an alignment highlighting the high conservation of the YLSALR peptide recognized by HMB3210 in RSV, BRSV, PVM and MPV sequences as compared to parainfluenza virus 5 (PIV5).

FIG. 22 shows a model of the pre-fusion RSV F protein showing the location of the YLSALR peptide and of the neighboring Palivizumab (PVZ) site and ribbon diagrams highlighting the rearrangement of the PVZ and HMB3210v3 sites in the pre- and post-fusion conformation of the RSV F protein.

FIGS. 24A, 24B and 24C show the sequences for the various heavy and light chain variants for HMB3210.

FIGS. 25A and 25B show the sequences for the various heavy and light chain variants for HMB2430.

DETAILED DESCRIPTION

Figure 1:
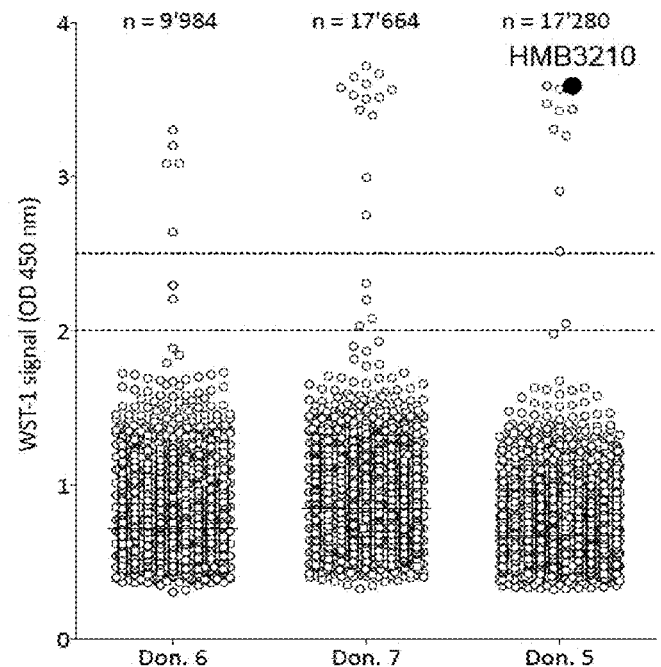
FIG. 1 shows the results of the screening of monoclonal antibodies produced by EBV-immortalized memory B cells from 7 donors (Don. 1 to 7) for their ability to neutralize RSV or MPV virus infection in vitro.
Figure 1:
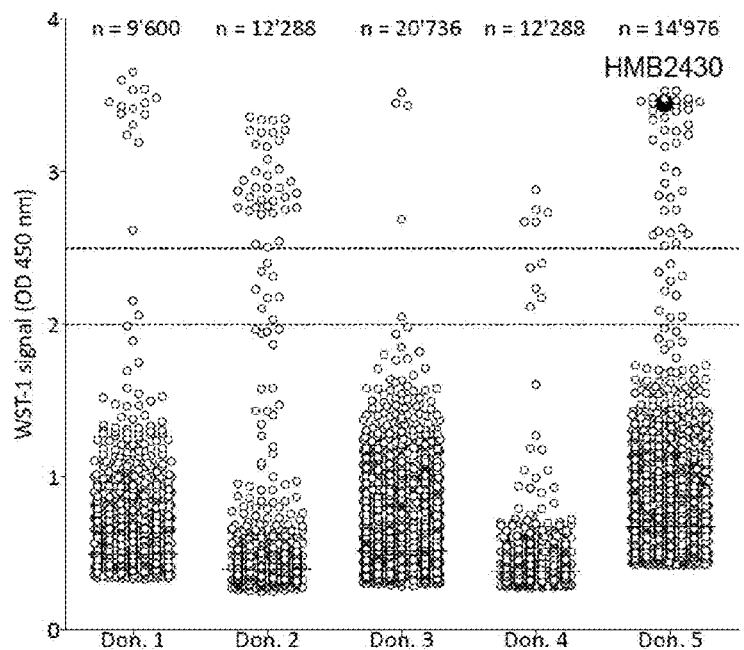

The invention is based, in part, on the discovery and isolation of antibodies that cross-neutralize both RSV and MPV or RSV, MPV, and PVM, as well as epitopes to which the antibodies of the invention bind. Such antibodies are desirable, as only one or few antibodies are required in order to neutralize both RSV and MPV or RSV, MPV, and PVM. Further, the cross-neutralizing antibodies are produced at high titers to reduce costs of production of medicaments comprising the antibodies for the treatment of RSV and/or MPV infection. In addition, the epitopes recognized by such antibodies may be part of a vaccine capable of inducing broad protection against both RSV and MPV.

Although the antibodies of the invention neutralize RSV, MPV, and PVM, in some embodiments of the invention, for example those related to the treatment of disease, development of vaccines, etc., the current disclosure refers only to RSV and MPV, as these viruses are human pathogens, while PVM is a mouse pathogen. As used herein, the terms "both RSV and MPV," and "RSV, MPV and PVM" are used interchangeably based on the context.

Accordingly, in one aspect, the invention provides an isolated antibody, antibody variants and antigen binding fragments thereof, that neutralize both RSV and MPV or RSV, MPV, and PVM. In one embodiment, the RSV is a human RSV. In another embodiment, the RSV is a bovine RSV. The antibodies of the invention neutralize both human RSV (hRSV) and bovine RSV (bRSV). In another embodiment, the MPV is a human MPV.

In one embodiment, the invention also provides an isolated antibody, or an antigen binding fragment thereof, that neutralizes infection of both group A and group B RSV. In another embodiment, the invention provides an isolated antibody, or an antigen binding fragment thereof, that neutralizes infection of both group A and group B MPV. In yet another embodiment, the invention provides an isolated antibody, or an antigen binding fragment thereof, that neutralizes infection of both group A and group B RSV as well as both group A and group B MPV.

As discussed earlier, RSV, MPV, and PVM have some similarities in their genetic structure. The amino acid sequences of the G and F proteins are classified into A and B groups in both RSV and MPV; MPV is further divided in 4 subgroups: A1, A2, B1 and B2. PVM is not subdivided into groups or sub-groups. The RSV, MPV or PVM F protein is a type I transmembrane surface protein that has an N-terminal cleaved signal peptide and a membrane anchor near the C-terminus. RSV and MPV F proteins are synthesized as inactive FO precursors that assemble into homotrimers and are activated by cleavage. The F protein is formed by three domains (DI to DIII), a fusion peptide (FP) and three heptad-repeats regions (HR-A, -B and -C). The RSV and MPV F glycoproteins direct viral penetration by fusion between the virion envelope and the host cell plasma membrane. In both cases, the N-terminus of the F subunit, that is created by proteolytic cleavage and contains the fusion peptide, inserts directly into the target membrane to initiate fusion. After binding to the target cell and subsequent activation, the metastable pre-fusion F protein undergoes a series of structural rearrangements that result in the insertion of the fusion peptide into the target cell membrane, followed by the formation of a stable helical bundle that forms as the viral and cell membranes are apposed. These structural changes lead to the formation of a stable post-fusion F protein. Later in infection, the F protein expressed on the cell surface of infected cells can mediate fusion with adjacent non-infected cells forming large syncytia.

The epitopes for Palivizumab and Motavizumab have been mapped on the post-fusion RSV F protein antigenic site II (also called site A) formed by residues 255-275. MAB19 and 101F target the post-fusion RSV F protein antigenic site IV (also called site C) of RSV formed by residues 422-438. MAB19 was tested in clinical trials but failed to show significant efficacy (Johnson et al., 1999, *The Journal of Infectious Diseases* 180:35-40; Meissner et al., 1999, *Antimicrobial Agents and Chemotherapy* 43:1183-1188).

To be effective, antibodies should recognize the pre-fusion F protein, which is the relevant conformation to block virus entry, and preferably avoids recognition of the abundant post-fusion F protein that can act as a decoy, thus consuming the antibody and reducing its efficacy. So far no antibodies recognizing the RSV pre-fusion but not the RSV post-fusion F protein have been isolated.

In one embodiment of the invention, the invention comprises an isolated antibody, or an antigen binding fragment thereof, that specifically binds RSV pre-fusion F protein and not RSV post-fusion F protein. In another embodiment, the invention comprises an isolated antibody, or an antigen binding fragment thereof, that specifically binds the pre-fusion F protein and not the post-fusion F protein of RSV and MPV. In another embodiment, the invention provides antibodies that specifically bind to the pre-fusion F protein but not to the post-fusion F protein of RSV, MPV and PVM.

The invention provides antibodies that bind to the F protein of RSV, MPV and PVM. Despite the fact that there is only approximately 33% and 40% amino acid sequence identity between RSV and MPV or RSV and PVM F proteins, respectively, the antibodies of the invention recognize a shared epitope present on RSV, MPV and PVM F proteins. This epitope is different from all those recognized by the hitherto know antibodies such as Palivizumab, Motavizumab, mAb 101F etc. The antibodies of the invention do not, for example, bind the antigenic site II (recognized by Motavizumab and Palivizumab), nor the antigenic site IV (recognized by mAb 101F), nor the antigenic site I (bound by mAb 131-2A). The epitopes recognized by the antibodies of the invention on the RSV F protein are also distinct from that recognized by the mAb D25, an antibody specific only to RSV. In addition, the epitopes recognized by the antibodies of the invention on the MPV F protein are distinct from that recognized by the mAb 234 (that recognizes an epitope on the MPV F protein which correspond to the antigenic site II on RSV F protein). In general, the antibodies of the invention recognize a conformational epitope. In one embodiment, the conformational epitope is present only under non-reducing conditions. In another embodiment, the conformational epitope relies on the presence of disulphide bonds between amino acid residues on the F protein.

As shown herein, the antibodies or antigen binding fragments of the invention bind specifically to several different strains of both RSV and MPV and neutralize both RSV and MPV. Further, the antibodies or antigen binding fragments of the invention bind specifically to, and cross-neutralize both group A and group B RSV as well as both group A and group B MPV, including all corresponding MPV subgroups (i.e. A1, A2, B1, and B2).

The antibody and antigen binding fragment of the invention have high neutralizing potency. The concentration of the antibody of the invention required for 50% neutralization of RSV, MPV and PVM, is, for example, about 500 ng/ml or less. In one embodiment, the concentration of the antibody of the invention required for 50% neutralization of RSV, MPV and PVM is about 500, 450, 400, 350, 300, 250, 200, 175, 150, 125, 100, 90, 80, 70, 60 or about 50 ng/ml or less. This means that only low concentrations of antibody are required for 50% neutralization of RSV, MPV and PVM. Specificity and potency can be measured using standard assays as known to one of skill in the art.

The antibodies of the invention may be human antibodies, monoclonal antibodies, human monoclonal antibodies, recombinant antibodies or purified antibodies. The invention also provides fragments of the antibodies of the invention, particularly fragments that retain the antigen-binding activity of the antibodies. Such fragments include, but are not limited to, single chain antibodies, Fab, Fab', F(ab')2, Fv or scFv. Although the specification, including the claims, may, in some places, refer explicitly to antigen binding fragment(s), antibody fragment(s), variant(s) and/or derivative(s) of antibodies, it is understood that the term "antibody" or "antibody of the invention" includes all categories of antibodies, namely, antigen binding fragment(s), antibody fragment(s), variant(s) and derivative(s) of antibodies.

The sequences of the heavy chains and light chains of several antibodies of the invention, each comprising three CDRs on the heavy chain and three CDRs on the light chain have been determined. The position of the CDR amino acids are defined according to the IMGT numbering system. The sequences of the CDRs, heavy chains, light chains as well as the sequences of the nucleic acid molecules encoding the CDRs, heavy chains, light chains of the antibodies of the invention are disclosed in the sequence listing. The CDRs of the antibody heavy chains are referred to as CDRH1 (or HCDR1), CDRH2 (or HCDR2) and CDRH3 (or HCDR3), respectively. Similarly, the CDRs of the antibody light chains are referred to as CDRL1 (or LCDR1), CDRL2 (or LCDR2) and CDRL3 (or LCDR3), respectively. Table 1 provides the SEQ ID numbers for the amino acid sequences of the six CDRs of the heavy and light chains, respectively, of the exemplary antibodies of the invention.

TABLE 1

SEQ ID Numbers for CDR Polypeptides of Antibodies that Neutralize RSV, MPV and PVM.

| | SEQ ID NOs. for CDR Polypeptides | | | | | |
|---|---|---|---|---|---|---|
| | CDRH1 | CDRH2 | CDRH3 | CDRL1 | CDRL2 | CDRL3 |
| 3210 variant 1 | 1 | 2 | 3 | 4 | 5 | 6 |
| 3210 variant 2 | 1 | 2 | 3 | 4 | 5 | 6 |
| 3210 variant 3 | 1 | 2 | 3 | 4 | 5 | 35 |
| 3210 variant 4 | 1 | 39 | 40 | 4 | 41 | 42 |
| 3210 variant 5 | 1 | 39 | 40 | 4 | 5 | 6 |
| 3210 variant 6 | 1 | 2 | 3 | 4 | 41 | 42 |
| 2430 variant 1 | 19 | 20 | 21 | 4 | 22 | 23 |
| 2430 variant 2 | 19 | 20 | 21 | 4 | 22 | 23 |
| 2430 variant 3 | 1 | 39 | 53 | 4 | 41 | 54 |
| 2430 variant 4 | 1 | 39 | 53 | 4 | 22 | 23 |
| 2430 variant 5 | 19 | 20 | 21 | 4 | 41 | 54 |

In one embodiment, an antibody or antibody fragment of the invention comprises at least one CDR with a sequence that has at least 95% sequence identity to any one of SEQ ID NOs: 1-6, 19-23, 35, 39-42, or 53-54. The CDRs of the variants of the antibody 3210 and antibody 2430 are provided in FIGS. 24 and 25 respectively (CDRs are highlighted in bold).

In another embodiment, the invention provides an antibody or antigen binding fragment comprising a heavy chain comprising one or more (i.e. one, two or all three) heavy chain CDRs from 3210 variant 1, 3210 variant 2, 3210 variant 3, 3210 variant 4, 3210 variant 5, 3210 variant 6, 2430 variant 1, 2430 variant 2, 2430 variant 3, 2430 variant 4 or 2430 variant 5.

In yet another embodiment, the antibody or antigen binding fragment of the invention comprises a heavy chain CDR1 with the amino acid sequence of SEQ ID NO: 1 or SEQ ID NO: 19; a heavy chain CDR2 with the amino acid sequence of SEQ ID NO: 2, SEQ ID NO: 20 or SEQ ID NO: 39; and a heavy chain CDR3 with the amino acid sequence of SEQ ID NO: 3, SEQ ID NO: 21, SEQ ID NO: 40 or SEQ ID NO: 53. In certain embodiments, an antibody or antibody fragment as provided herein comprises a heavy chain comprising the amino acid sequence of (i) SEQ ID NO: 1 for CDRH1, SEQ ID NO: 2 for CDRH2 and SEQ ID NO: 3 for CDRH3, (ii) SEQ ID NO: 1 for CDRH1, SEQ ID NO: 39 for CDRH2, and SEQ ID NO: 40 for CDRH3, (iii) SEQ ID NO: 19 for CDRH1, SEQ ID NO; 20 for CDRH2, and SEQ ID NO: 21 for CDRH3, or (iv) or SEQ ID NO: 1 for CDRH1, SEQ ID NO: 39 for CDRH2, and SEQ ID NO: 53 for CDRH3.

Also provided is an antibody or antigen binding fragment comprising a light chain comprising one or more (i.e. one, two or all three) light chain CDRs from 3210 variant 1, 3210 variant 2, 3210 variant 3, 3210 variant 4, 3210 variant 5, 3210 variant 6, 2430 variant 1, 2430 variant 2, 2430 variant 3, 2430 variant 4 or 2430 variant 5. In one embodiment, the antibody or antigen binding fragment of the invention comprises a light chain CDR1 with the amino acid sequence of SEQ ID NO: 4; a light chain CDR2 with the amino acid sequence of SEQ ID NO: 5, SEQ ID NO: 22 or SEQ ID NO: 41; and a light chain CDR3 with the amino acid sequence of SEQ ID NO: 6, SEQ ID NO: 23, SEQ ID NO: 35, SEQ ID NO: 42 or SEQ ID NO: 54. In certain embodiments, an antibody or antibody fragment as provided herein comprises a light chain comprising the amino acid sequence of (i) SEQ ID NO: 4 for CDRL1, SEQ ID NO: 5 for CDRL2, and SEQ ID NO: 6 for CDRL3; (ii) SEQ ID NO: 4 for CDRL1, SEQ ID NO: 5 for CDRL2, and SEQ ID NO: 35 for CDRL3; (iii) SEQ ID NO: 4 for CDRL1, SEQ ID NO: 41 for CDRL2, and SEQ ID NO: 42 for CDRL3; (iv) SEQ ID NO: 4 for CDRL1, SEQ ID NO; 22 for CDRL2, and SEQ ID NO: 23 for CDRL3; or (v) SEQ ID NO: 4 for CDRL1, SEQ ID NO: 41 for CDRL2, and SEQ ID NO: 54 for CDRL3.

In one embodiment, an antibody of the invention, or antigen binding fragment thereof, comprises all of the CDRs of antibody 3210 variant 1 as listed in Table 1, and neutralizes infection of RSV, MPV and PVM. In another embodiment, an antibody of the invention, or antigen binding fragment thereof, comprises all of the CDRs of antibody 3210 variant 2 as listed in Table 1, and neutralizes infection of RSV, MPV and PVM. In another embodiment, an antibody of the invention, or antigen binding fragment thereof, comprises all of the CDRs of antibody 3210 variant 3 as listed in Table 1, and neutralizes infection of RSV, MPV and PVM. In another embodiment, an antibody of the invention, or antigen binding fragment thereof, comprises all of the CDRs of antibody 3210 variant 4 as listed in Table 1, and neutralizes infection of both RSV, MPV and PVM. In another embodiment, an antibody of the invention, or antigen binding fragment thereof, comprises all of the CDRs of antibody 3210 variant 5 as listed in Table 1, and neutralizes infection of both RSV, MPV and PVM. In another embodiment, an antibody of the invention, or antigen binding fragment thereof, comprises all of the CDRs of antibody 3210 variant 6 as listed in Table 1, and neutralizes infection of both RSV, MPV and PVM.

In yet another embodiment, an antibody of the invention, or antigen binding fragment thereof, comprises all of the CDRs of antibody 2430 variant 1 as listed in Table 1, and neutralizes infection of both RSV, MPV and PVM. In another embodiment, an antibody of the invention, or antigen binding fragment thereof, comprises all of the CDRs of antibody 2430 variant 2 as listed in Table 1, and neutralizes infection of both RSV, MPV and PVM. In another embodiment, an antibody of the invention, or antigen binding fragment thereof, comprises all of the CDRs of antibody 2430 variant 3 as listed in Table 1, and neutralizes infection of both RSV, MPV and PVM. In another embodiment, an antibody of the invention, or antigen binding fragment thereof, comprises all of the CDRs of antibody 2430 variant 4 as listed in Table 1, and neutralizes infection of both RSV, MPV and PVM. In another embodiment, an antibody of the invention, or antigen binding fragment thereof, comprises all of the CDRs of antibody 2430 variant 5 as listed in Table 1, and neutralizes infection of both RSV, MPV and PVM.

The SEQ ID numbers for the amino acid sequence for the heavy chain variable region (VH) and the light chain variable region (VL) of exemplary antibodies of the invention as well as the SEQ ID numbers for the nucleic acid sequences encoding them are listed in Table 2.

TABLE 2

SEQ ID Numbers for $V_H$ and $V_L$ amino acid and nucleic acid residues for Antibodies that Neutralize RSV, MPV and PVM.

| | $V_H$ chain | $V_L$ chain | SEQ ID NOs. for $V_H$ and $V_L$ amino acid and nucleic acid residues | | | |
|---|---|---|---|---|---|---|
| | | | $V_H$ amino acid | $V_L$ amino acid | $V_H$ nucleic acid | $V_L$ nucleic acid |
| 3210 variant 1 | VH.1 | VL | 13 | 14 | 15 | 16 |
| 3210 variant 2 | VH.2 | VL | 17 | 14 | 18 | 16 |
| 3210 variant 3 | VH.2 | VL.3 | 17 | 37 | 18 | 38 |
| 3210 variant 4 | VH.3 | VL.4 | 49 | 50 | 51 | 52 |
| 3210 variant 5 | VH.3 | VL | 49 | 14 | 51 | 16 |
| 3210 variant 6 | VH.2 | VL.4 | 17 | 50 | 18 | 52 |
| 2430 variant 1 | VH.1 | VL | 29 | 30 | 31 | 32 |
| 2430 variant 2 | VH.2 | VL | 33 | 30 | 34 | 32 |
| 2430 variant 3 | VH.3 | VL.2 | 59 | 60 | 61 | 62 |
| 2430 variant 4 | VH.3 | VL | 59 | 30 | 61 | 32 |
| 2430 variant 5 | VH.2 | VL.2 | 33 | 60 | 34 | 62 |

In one embodiment, an antibody or antibody fragment of the invention comprises a heavy chain variable region having an amino acid sequence that is about 70%, 75%, 80%, 85%, 90%, 95%, 97%, 98%, 99% or 100% identical to the sequence recited in any one of SEQ ID NOs: 13, 17, 29, 33, 49 or 59. In another embodiment, an antibody or antibody fragment of the invention comprises a light chain variable region having an amino acid sequence that is about 70%, 75%, 80%, 85%, 90%, 95%, 97%, 98%, 99% or 100% identical to the sequence recited in SEQ ID NOs: 14, 30, 37, 50 or 60. In yet another embodiment, an antibody or antibody fragment of the invention comprises a heavy chain or a light chain variable region having an amino acid sequence that is about 70%, 75%, 80%, 85%, 90%, 95%, 97%, 98%, 99% or 100% identical to the sequences provided in FIGS. 24 and 25.

In another embodiment of the invention, the invention comprises an antibody, or an antigen binding fragment thereof, that neutralizes infection of RSV, MPV and PVM and comprises a heavy chain variable region comprising the amino acid sequence of SEQ ID NO: 13 and a light chain variable region comprising the amino acid sequence of SEQ ID NO: 14; or a heavy chain variable region comprising the amino acid sequence of SEQ ID NO: 13 and a light chain variable region comprising the amino acid sequence of SEQ ID NO: 37; or a heavy chain variable region comprising the amino acid sequence of SEQ ID NO: 13 and a light chain variable region comprising the amino acid sequence of SEQ ID NO: 50; or a heavy chain variable region comprising the amino acid sequence of SEQ ID NO: 17 and a light chain variable region comprising the amino acid sequence of SEQ ID NO: 14; or a heavy chain variable region comprising the amino acid sequence of SEQ ID NO: 17 and a light chain variable region comprising the amino acid sequence of SEQ ID NO: 37; or a heavy chain variable region comprising the amino acid sequence of SEQ ID NO: 49 and a light chain variable region comprising the amino acid sequence of SEQ ID NO: 50; or a heavy chain variable region comprising the amino acid sequence of SEQ ID NO: 49 and a light chain variable region comprising the amino acid sequence of SEQ ID NO: 14; or a heavy chain variable region comprising the amino acid sequence of SEQ ID NO: 49 and a light chain variable region comprising the amino acid sequence of SEQ ID NO: 37; or a heavy chain variable region comprising the amino acid sequence of SEQ ID NO: 17 and a light chain variable region comprising the amino acid sequence of SEQ ID NO: 50.

In yet another embodiment of the invention, the invention comprises an antibody, or an antigen binding fragment thereof, that neutralizes infection of RSV, MPV and PVM and comprises a heavy chain variable region comprising the amino acid sequence of SEQ ID NO: 29 and a light chain variable region comprising the amino acid sequence of SEQ ID NO: 30; or a heavy chain variable region comprising the amino acid sequence of SEQ ID NO: 29 and a light chain variable region comprising the amino acid sequence of SEQ ID NO: 60; or a heavy chain variable region comprising the amino acid sequence of SEQ ID NO: 33 and a light chain variable region comprising the amino acid sequence of SEQ ID NO: 30; or a heavy chain variable region comprising the amino acid sequence of SEQ ID NO: 59 and a light chain variable region comprising the amino acid sequence of SEQ ID NO: 60; or a heavy chain variable region comprising the amino acid sequence of SEQ ID NO: 59 and a light chain variable region comprising the amino acid sequence of SEQ ID NO: 30; or a heavy chain variable region comprising the amino acid sequence of SEQ ID NO: 33 and a light chain variable region comprising the amino acid sequence of SEQ ID NO: 60.

Examples of antibodies of the invention include, but are not limited to, HMB3210 variant 1, HMB3210 variant 2, HMB3210 variant 3, HMB3210 variant 4, HMB3210 variant 5, HMB3210 variant 6, HMB2430 variant 1, HMB2430 variant 2, HMB2430 variant 3, HMB2430 variant 4 or HMB2430 variant 5.

The invention further comprises an antibody, or fragment thereof, that binds to the same epitope as an antibody or antigen binding fragment of the invention, or an antibody that competes with an antibody or antigen binding fragment of the invention.

As can be seen from Tables 1 and 2, the CDRs, heavy chains and light chains of the disclosed antibodies can be interchanged to provide new antibodies that retain their binding and neutralizing capabilities. Antibodies of the invention thus include antibodies and antigen binding fragments comprising any combination of the CDRs provided in Table 1 or heavy and light chains provided in Table 2.

Antibodies of the invention also include hybrid antibody molecules that comprise one or more CDRs from an antibody of the invention and one or more CDRs from another antibody to the same epitope. In one embodiment, such hybrid antibodies comprise three CDRs from an antibody of the invention and three CDRs from another antibody to the same epitope. Exemplary hybrid antibodies comprise (i) the three light chain CDRs from an antibody of the invention and the three heavy chain CDRs from another antibody to the same epitope, or (ii) the three heavy chain CDRs from an antibody of the invention and the three light chain CDRs from another antibody to the same epitope.

Variant antibodies are also included within the scope of the invention. Thus, variants of the sequences recited in the application are also included within the scope of the invention. Such variants include natural variants generated by somatic mutation in vivo during the immune response or in vitro upon culture of immortalized B cell clones. Alternatively, variants may arise due to the degeneracy of the genetic code or may be produced due to errors in transcription or translation.

Further variants of the antibody sequences having improved affinity and/or potency may be obtained using methods known in the art and are included within the scope of the invention. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences of the invention are also within the scope of the invention.

In one embodiment variant antibody sequences may share 70% or more (i.e. 75%, 80%, 85%, 90%, 95%, 97%, 98%, 99% or more) amino acid sequence identity with the sequences recited in the application. In some embodiments such sequence identity is calculated with regard to the full length of the reference sequence (i.e. the sequence recited in the application). In some further embodiments, percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

In another aspect, the invention also includes nucleic acid sequences encoding part or all of the light and heavy chains and CDRs of the antibodies of the present invention. Provided herein are nucleic acid sequences encoding part or all of the light and heavy chains and CDRs of exemplary antibodies of the invention. Table 2 provides the SEQ ID numbers for the nucleic acid sequences encoding the heavy chain and light chain variable regions of some examples of antibodies of the invention. Table 3 provides the SEQ ID numbers for the nucleic acid sequences encoding the CDRs of the exemplary antibodies of the invention. Due to the redundancy of the genetic code, variants of these nucleic acid sequences will exist that encode the same amino acid sequences.

TABLE 3

SEQ ID Numbers for CDR Polynucleotides of Antibodies that Neutralize RSV, MPV and PVM.

| | SEQ ID NOs. for CDR Polynucleotides | | | | | |
|---|---|---|---|---|---|---|
| | CDRH1 | CDRH2 | CDRH3 | CDRL1 | CDRL2 | CDRL3 |
| 3210 variant 1 | 7 | 8 | 9 | 10 | 11 | 12 |
| 3210 variant 2 | 7 | 8 | 9 | 10 | 11 | 12 |
| 3210 variant 3 | 7 | 8 | 9 | 10 | 11 | 36 |
| 3210 variant 4 | 43 | 44 | 45 | 46 | 47 | 48 |
| 3210 variant 5 | 43 | 44 | 45 | 10 | 11 | 12 |
| 3210 variant 6 | 7 | 8 | 9 | 46 | 47 | 48 |
| 2430 variant 1 | 24 | 25 | 26 | 10 | 27 | 28 |
| 2430 variant 2 | 24 | 25 | 26 | 10 | 27 | 28 |
| 2430 variant 3 | 55 | 44 | 56 | 57 | 47 | 58 |
| 2430 variant 4 | 55 | 44 | 56 | 10 | 27 | 28 |
| 2430 variant 5 | 24 | 25 | 26 | 57 | 47 | 58 |

In one embodiment, nucleic acid sequences according to the invention include nucleic acid sequences having at least 70%, at least 75%, at least 80%, at least 85%, at least 90%, at least 95%, at least 98%, or at least 99% identity to the nucleic acid encoding a heavy or light chain of an antibody of the invention. In another embodiment, a nucleic acid sequence of the invention has the sequence of a nucleic acid encoding a heavy or light chain CDR of an antibody of the invention. For example, a nucleic acid sequence according to the invention comprises a sequence that is at least 75%, at least 80%, at least 85%, at least 90%, at least 95%, at least 98%, or at least 99% identical to the nucleic acid sequences of SEQ ID NOs: 7-12, 15, 16, 18, 24-28, 31-32, 34, 36, 38, 43-48, 51-52, 55-58, or 61-62.

In yet another embodiment, nucleic acid sequences according to the invention include nucleic acid sequences having at least 70%, at least 75%, at least 80%, at least 85%, at least 90%, at least 95%, at least 98%, or at least 99% identity to the nucleic acid encoding a heavy or light chain of an antibody of the invention as provided in FIGS. 24 and 25.

Further included within the scope of the invention are vectors, for example, expression vectors, comprising a nucleic acid sequence according to the invention. Cells transformed with such vectors are also included within the scope of the invention. Examples of such cells include but are not limited to, eukaryotic cells, e.g., yeast cells, animal cells or plant cells. In one embodiment the cells are mammalian, e.g., human, CHO, HEK293T, PER.C6, NS0, myeloma or hybridoma cells.

The invention also relates to monoclonal antibodies that bind to an epitope capable of binding the antibodies or antigen binding fragments of the invention.

Monoclonal and recombinant antibodies are particularly useful in identification and purification of the individual polypeptides or other antigens against which they are directed. The antibodies of the invention have additional utility in that they may be employed as reagents in immunoassays, radioimmunoassays (RIA) or enzyme-linked immunosorbent assays (ELISA). In these applications, the antibodies can be labeled with an analytically-detectable reagent such as a radioisotope, a fluorescent molecule or an enzyme. The antibodies may also be used for the molecular identification and characterization (epitope mapping) of antigens.

Antibodies of the invention can be coupled to a drug for delivery to a treatment site or coupled to a detectable label to facilitate imaging of a site comprising cells of interest, such as cells infected with RSV or MPV or both RSV and MPV. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest (an epitope or RSV or MPV or both) can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include 125I, 131I, 35S, or 3H. Such labeled reagents may be used in a variety of well-known assays, such as radioimmunoassays, enzyme immunoassays, e.g., ELISA, fluorescent immunoassays, and the like. (See U.S. Pat. No. 3,766,162; U.S. Pat. No. 3,791, 932; U.S. Pat. No. 3,817,837; and U.S. Pat. No. 4,233,402 for example).

An antibody according to the invention may be conjugated to a therapeutic moiety such as a cytotoxin, a therapeutic agent, or a radioactive metal ion or radioisotope. Examples of radioisotopes include, but are not limited to, I-131, I-123, I-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurds, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158.

Alternatively, an antibody, or antibody fragment thereof, can be conjugated to a second antibody, or antibody fragment thereof, to form an antibody heteroconjugate as described in U.S. Pat. No. 4,676,980. In addition, linkers may be used between the labels and the antibodies of the invention (e.g., U.S. Pat. No. 4,831,175). Antibodies or, antigen-binding fragments thereof may be directly labeled with radioactive iodine, indium, yttrium, or other radioactive particle known in the art (e.g., U.S. Pat. No. 5,595,721). Treatment may consist of a combination of treatment with conjugated and non-conjugated antibodies administered simultaneously or subsequently (e.g., WO00/52031; WO00/52473).

Antibodies of the invention may also be attached to a solid support. Additionally, antibodies of the invention, or functional antibody fragments thereof, can be chemically modified by covalent conjugation to a polymer to, for example, increase their circulating half-life. Examples of polymers, and methods to attach them to peptides, are shown in U.S. Pat. No. 4,766,106; U.S. Pat. No. 4,179,337; U.S. Pat. No. 4,495,285 and U.S. Pat. No. 4,609,546. In some embodiments the polymers may be selected from polyoxyethylated polyols and polyethylene glycol (PEG). PEG is soluble in water at room temperature and has the general formula: R(O—CH2-CH2)n O—R where R can be hydrogen, or a protective group such as an alkyl or alkanol group. In one embodiment the protective group may have between 1 and 8 carbons. In a further embodiment the protective group is methyl. The symbol n is a positive integer. In one embodiment n is between 1 and 1,000. In another embodiment n is between 2 and 500. In one embodiment the PEG has an average molecular weight between 1,000 and 40,000. In a further embodiment the PEG has a molecular weight between 2,000 and 20,000. In yet a further embodiment the PEG has a molecular weight between 3,000 and 12,000. In one embodiment PEG has at least one hydroxy group. In another embodiment the PEG has a terminal hydroxy group.

In yet another embodiment it is the terminal hydroxy group which is activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. In one embodiment, POG is used. Without being bound by any theory, because the glycerol backbone of polyoxyethylated glycerol is the same backbone occurring naturally in, for example, animals and humans in mono-, di-, triglycerides, this branching would not necessarily be seen as a foreign agent in the body. In some embodiments POG has a molecular weight in the same range as PEG. Another drug delivery system that can be used for increasing circulatory half-life is the liposome. Methods of preparing liposome delivery systems are known to one of skill in the art. Other drug delivery systems are known in the art and are described in, for example, referenced in Poznansky et al. (1980) and Poznansky (1984).

Antibodies of the invention may be provided in purified form. Typically, the antibody will be present in a composition that is substantially free of other polypeptides e.g., where less than 90% (by weight), usually less than 60% and more usually less than 50% of the composition is made up of other polypeptides.

Antibodies of the invention may be immunogenic in non-human (or heterologous) hosts e.g., in mice. In particular, the antibodies may have an idiotope that is immunogenic in non-human hosts, but not in a human host. Antibodies of the invention for human use include those that cannot be easily isolated from hosts such as mice, goats, rabbits, rats, non-primate mammals, etc. and cannot generally be obtained by humanization or from xeno-mice.

Antibodies of the invention can be of any isotype (e.g., IgA, IgG, IgM i.e. an α, γ or μ heavy chain), but will generally be IgG. Within the IgG isotype, antibodies may be IgG1, IgG2, IgG3 or IgG4 subclass. Antibodies of the invention may have a κ or a λ light chain.

Production of Antibodies

Antibodies according to the invention can be made by any method known in the art. For example, the general methodology for making monoclonal antibodies using hybridoma technology is well known (Kohler, G. and Milstein, C., 1975; Kozbar et al. 1983). In one embodiment, the alternative EBV immortalization method described in WO2004/076677 is used.

Using the method described in WO 2004/076677, B cells producing the antibody of the invention can be transformed with EBV and a polyclonal B cell activator. Additional stimulants of cellular growth and differentiation may optionally be added during the transformation step to further enhance the efficiency. These stimulants may be cytokines such as IL-2 and IL-15. In one aspect, IL-2 is added during the immortalization step to further improve the efficiency of immortalization, but its use is not essential. The immortalized B cells produced using these methods can then be cultured using methods known in the art and antibodies isolated therefrom.

Using the method described in WO 2010/046775, plasma cells can be cultured in limited numbers, or as single plasma cells in microwell culture plates. Antibodies can be isolated from the plasma cell cultures. Further, from the plasma cell cultures, RNA can be extracted and PCR can be performed using methods known in the art. The VH and VL regions of the antibodies can be amplified by RT-PCR, sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

The antibodies may be further purified, if desired, using filtration, centrifugation and various chromatographic methods such as HPLC or affinity chromatography. Techniques for purification of antibodies, e.g., monoclonal antibodies, including techniques for producing pharmaceutical-grade antibodies, are well known in the art.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, *Nature Biotechnology* 9: 1126-1136).

Standard techniques of molecular biology may be used to prepare DNA sequences encoding the antibodies or antibody fragments of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example *E. coli*, and other microbial systems may be used, in part, for expression of antibody fragments such as Fab and F(ab')2 fragments, and especially Fv fragments and single chain antibody fragments, for example, single chain Fvs. Eukaryotic, e.g., mammalian, host cell expression systems may be used for production of larger antibody molecules, including complete antibody molecules. Suitable mammalian host cells include, but are not limited to, CHO, HEK293T, PER.C6, NS0, myeloma or hybridoma cells.

The present invention also provides a process for the production of an antibody molecule according to the present invention comprising culturing a host cell comprising a vector encoding a nucleic acid of the present invention under conditions suitable for expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Alternatively, antibodies according to the invention may be produced by (i) expressing a nucleic acid sequence according to the invention in a host cell, and (ii) isolating the expressed antibody product. Additionally, the method may include (iii) purifying the isolated antibody.

Transformed B cells and cultured plasma cells may be screened for those producing antibodies of the desired specificity or function.

The screening step may be carried out by any immunoassay, e.g., ELISA, by staining of tissues or cells (including transfected cells), by neutralization assay or by one of a number of other methods known in the art for identifying desired specificity or function. The assay may select on the basis of simple recognition of one or more antigens, or may select on the additional basis of a desired function e.g., to select neutralizing antibodies rather than just antigen-binding antibodies, to select antibodies that can change characteristics of targeted cells, such as their signaling cascades, their shape, their growth rate, their capability of influencing other cells, their response to the influence by other cells or by other reagents or by a change in conditions, their differentiation status, etc.

Individual transformed B cell clones may then be produced from the positive transformed B cell culture. The cloning step for separating individual clones from the mixture of positive cells may be carried out using limiting dilution, micromanipulation, single cell deposition by cell sorting or another method known in the art.

Nucleic acid from the cultured plasma cells can be isolated, cloned and expressed in HEK293T cells or other known host cells using methods known in the art.

The immortalized B cell clones or the transfected host-cells of the invention can be used in various ways e.g., as a source of monoclonal antibodies, as a source of nucleic acid (DNA or mRNA) encoding a monoclonal antibody of interest, for research, etc.

The invention provides a composition comprising immortalized B memory cells or transfected host cells that produce antibodies that neutralize infection of both that neutralizes infection of RSV, MPV and PVM.

The immortalized B cell clone or the cultured plasma cells of the invention may also be used as a source of nucleic acid for the cloning of antibody genes for subsequent recombinant expression. Expression from recombinant sources is more common for pharmaceutical purposes than expression from B cells or hybridomas e.g., for reasons of stability, reproducibility, culture ease, etc.

Thus the invention provides a method for preparing a recombinant cell, comprising the steps of: (i) obtaining one or more nucleic acids (e.g., heavy and/or light chain mRNAs) from the B cell clone or the cultured plasma cells that encodes the antibody of interest; (ii) inserting the nucleic acid into an expression vector and (iii) transfecting the vector into a host cell in order to permit expression of the antibody of interest in that host cell.

Similarly, the invention provides a method for preparing a recombinant cell, comprising the steps of: (i) sequencing nucleic acid(s) from the B cell clone or the cultured plasma cells that encodes the antibody of interest; and (ii) using the sequence information from step (i) to prepare nucleic acid(s) for insertion into a host cell in order to permit expression of the antibody of interest in that host cell. The nucleic acid may, but need not, be manipulated between steps (i) and (ii) to introduce restriction sites, to change codon usage, and/or to optimize transcription and/or translation regulatory sequences.

The invention also provides a method of preparing a transfected host cell, comprising the step of transfecting a host cell with one or more nucleic acids that encode an antibody of interest, wherein the nucleic acids are nucleic acids that were derived from an immortalized B cell clone or a cultured plasma cell of the invention. Thus the procedures for first preparing the nucleic acid(s) and then using it to transfect a host cell can be performed at different times by different people in different places (e.g., in different countries).

These recombinant cells of the invention can then be used for expression and culture purposes. They are particularly useful for expression of antibodies for large-scale pharmaceutical production. They can also be used as the active ingredient of a pharmaceutical composition. Any suitable culture technique can be used, including but not limited to static culture, roller bottle culture, ascites fluid, hollow-fiber type bioreactor cartridge, modular minifermenter, stirred tank, microcarrier culture, ceramic core perfusion, etc.

Methods for obtaining and sequencing immunoglobulin genes from B cells or plasma cells are well known in the art (e.g., see Chapter 4 of Kuby Immunology, 4th edition, 2000).

The transfected host cell may be a eukaryotic cell, including yeast and animal cells, particularly mammalian cells (e.g., CHO cells, NS0 cells, human cells such as PER.C6 or HKB-11 cells, myeloma cells), as well as plant cells. Preferred expression hosts can glycosylate the antibody of the invention, particularly with carbohydrate structures that are not themselves immunogenic in humans. In one embodiment the transfected host cell may be able to grow in serum-free media. In a further embodiment the transfected host cell may be able to grow in culture without the presence of animal-derived products. The transfected host cell may also be cultured to give a cell line.

The invention also provides a method for preparing one or more nucleic acid molecules (e.g., heavy and light chain genes) that encode an antibody of interest, comprising the steps of: (i) preparing an immortalized B cell clone or culturing plasma cells according to the invention; (ii) obtaining from the B cell clone or the cultured plasma cells nucleic acid that encodes the antibody of interest. Further, the invention provides a method for obtaining a nucleic acid sequence that encodes an antibody of interest, comprising the steps of: (i) preparing an immortalized B cell clone or culturing plasma cells according to the invention; (ii) sequencing nucleic acid from the B cell clone or the cultured plasma cells that encodes the antibody of interest.

The invention also provides a method of preparing nucleic acid molecule(s) that encode an antibody of interest, comprising the step of obtaining the nucleic acid that was obtained from a transformed B cell clone or cultured plasma cells of the invention. Thus the procedures for first obtaining the B cell clone or the cultured plasma cell, and then obtaining nucleic acid(s) from the B cell clone or the cultured plasma cells can be performed at different times by different people in different places (e.g., in different countries).

The invention provides a method for preparing an antibody (e.g., for pharmaceutical use), comprising the steps of: (i) obtaining and/or sequencing one or more nucleic acids (e.g., heavy and light chain genes) from the selected B cell clone or the cultured plasma cells expressing the antibody of interest; (ii) inserting the nucleic acid(s) into or using the nucleic acid(s) sequence(s) to prepare an expression vector; (iii) transfecting a host cell that can express the antibody of interest; (iv) culturing or sub-culturing the transfected host cells under conditions where the antibody of interest is expressed; and, optionally, (v) purifying the antibody of interest.

The invention also provides a method of preparing an antibody comprising the steps of: culturing or sub-culturing a transfected host cell population under conditions where the antibody of interest is expressed and, optionally, purifying the antibody of interest, wherein said transfected host cell population has been prepared by (i) providing nucleic acid(s) encoding a selected antibody of interest that is produced by a B cell clone or cultured plasma cells prepared as described above, (ii) inserting the nucleic acid(s) into an expression vector, (iii) transfecting the vector in a host cell that can express the antibody of interest, and (iv) culturing or sub-culturing the transfected host cell comprising the inserted nucleic acids to produce the antibody of interest. Thus the procedures for first preparing the recombinant host cell and then culturing it to express antibody can be performed at very different times by different people in different places (e.g., in different countries).

Epitopes

As mentioned above, the antibodies of the invention can be used to map the epitopes to which they bind. The inventors have discovered that the neutralizing antibodies of the invention are directed towards epitopes found on the pre-fusion, but not post-fusion, F protein. In one embodiment, the antibodies, or antigen binding fragments thereof, bind RSV pre-fusion F protein and not RSV post-fusion F protein. In another embodiment, the antibodies, or antigen binding fragments thereof, bind the pre-fusion F protein and not the post-fusion F protein of RSV and MPV. In yet another embodiment, the antibodies, or antigen binding fragments thereof, bind to the pre-fusion F protein but not to the post-fusion F protein of RSV, MPV and PVM.

The epitopes to which the antibodies of the invention bind may be linear (continuous) or conformational (discontinuous). In one embodiment, the antibodies and antibody fragments of the invention bind a conformational epitope. In another embodiment, the conformational epitope is present only under non-reducing conditions. Without being bound to any theory, the conformational epitope bound by the antibodies of the invention relies on the presence of disulphide bonds between amino acid residues on the F protein.

In another embodiment, the epitope to which the antibodies of the invention bind is distinct from antigenic site I, antigenic site II, antigenic site IV as defined on the RSV post-fusion F protein and corresponding sites on the MPV F protein. In yet another embodiment, the antibodies and antigen binding fragments of the invention do not cross-compete with Palivizumab, Motavizumab, mAb 101F, mAb 131-2A or mAb D25 for binding to the F protein of RSV; nor do they cross-compete with mAb 234 for binding to the F protein of MPV.

In another embodiment, the region to which the antibodies of the invention bind comprises a polypeptide located in the N-terminal portion of the RSV F protein, spanning residues SAVSKGYLSALRTGWYTSVIT (SEQ ID NO: 63). The core part in this polypeptide is formed by the residues Y(x1)S(x2)LRTGW, which are highly conserved between RSV, MPV and PVM, and wherein the amino acid at position (x1) can be, but is not limited to, L, F, or K, and wherein amino acid at position (x2) can be, but is not limited to, A or V. Examples of polypeptide variants to which the antibodies of the invention bind include, but are not limited to, YLSALRTGW (SEQ ID NO: 64), YLSVLRTGW (SEQ ID NO: 65), YFSALRTGW (SEQ ID NO: 66), YFSVLRTGW (SEQ ID NO: 67), YKSALRTGW (SEQ ID NO: 68), and YKSVLRTGW (SEQ ID NO: 69).

The polypeptides that bind to the antibodies of the present invention may have a number of uses. The polypeptides and polypeptide variants thereof in purified or synthetic form can be used to raise immune responses (i.e., as a vaccine, or for the production of antibodies for other uses) or for screening sera for antibodies that immunoreact with the epitope or mimotopes thereof. In one embodiment such polypeptides or polypeptide variants, or antigen comprising such an polypeptides or polypeptide variants may be used as a vaccine for raising an immune response that comprises antibodies of the same quality as those described in the present invention. The antibodies and antibody fragments of the invention can also be used in a method of monitoring the quality of vaccines. In particular the antibodies can be used to check that the antigen in a vaccine contains the correct immunogenic epitope in the correct conformation. The use of an antibody of the invention, or an antigen binding fragment thereof, for monitoring the quality of a vaccine against RSV or MPV or both RSV and MPV by, for example, checking that the antigen of said vaccine contains the specific epitope in the correct conformation is also contemplated to be within the scope of the invention.

The polypeptides that bind to the antibodies of the present invention may also be useful in screening for ligands that bind to said polypeptides. Such ligands, include but are not limited to antibodies; including those from camels, sharks and other species, fragments of antibodies, peptides, phage display technology products, aptamers, adnectins or fragments of other viral or cellular proteins, may block the epitope and so prevent infection. Such ligands are encompassed within the scope of the invention.

Pharmaceutical Compositions

The invention provides a pharmaceutical composition comprising one or more of: the antibodies or antibody fragments of the invention; nucleic acid encoding such antibodies or fragments; vectors encoding the nucleic acids; or polypeptides recognized by the antibodies or antigen binding fragment of the invention. The pharmaceutical composition may also contain a pharmaceutically acceptable carrier or excipient. Although the carrier or excipient may facilitate administration, it should not itself induce the production of antibodies harmful to the individual receiving the composition. Nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the subject.

Within the scope of the invention are compositions present in several forms of administration; the forms include, but are not limited to, those forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody molecule may be in dry form, for reconstitution before use with an appropriate sterile liquid.

Once formulated, the compositions of the invention can be administered directly to the subject. In one embodiment the compositions are adapted for administration to mammalian, e.g., human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. Known antibody-based pharmaceuticals provide guidance relating to frequency of administration e.g., whether a pharmaceutical should be delivered daily, weekly, monthly, etc. Frequency and dosage may also depend on the severity of symptoms.

Compositions of the invention may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition, like Synagis™ and Herceptin™, for reconstitution with sterile water containing a preservative). The composition may be prepared for topical administration e.g., as an ointment, cream or powder. The composition may be prepared for oral administration e.g., as a tablet or capsule, as a spray, or as a syrup (optionally flavored). The composition may be prepared for pulmonary administration e.g., as an inhaler, using a fine powder or a spray. The composition may be prepared as a suppository or pessary. The composition may be prepared for nasal, aural or ocular administration e.g., as drops. The composition may be in kit form, designed such that a combined composition is reconstituted just prior to administration to a subject. For example, a lyophilized antibody can be provided in kit form with sterile water or a sterile buffer.

It will be appreciated that the active ingredient in the composition will be an antibody molecule, an antibody fragment or variants and derivatives thereof. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Gennaro (2000) Remington: The Science and Practice of Pharmacy, 20th edition, ISBN: 0683306472.

Pharmaceutical compositions of the invention generally have a pH between 5.5 and 8.5, in some embodiments this may be between 6 and 8, and in other embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

Pharmaceutical compositions will include an effective amount of one or more antibodies of the invention and/or a polypeptide comprising an epitope that binds an antibody of the invention i.e., an amount that is sufficient to treat, ameliorate, attenuate or prevent a desired disease or condition, or to exhibit a detectable therapeutic effect. Therapeutic effects also include reduction or attenuation in pathogenic potency or physical symptoms. The precise effective amount for any particular subject will depend upon their size, weight, and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.01 mg/kg to about 50 mg/kg, or about 0.05 mg/kg to about 10 mg/kg of the compositions of the present invention in the individual to which it is administered. Known antibody-based pharmaceuticals provide guidance in this respect e.g., Herceptin™ is administered by intravenous infusion of a 21 mg/ml solution, with an initial loading dose of 4 mg/kg body weight and a weekly maintenance dose of 2 mg/kg body weight; Rituxan™ is administered weekly at 375 mg/m$^2$; etc.

In one embodiment compositions can include more than one (e.g., 2, 3, etc.) antibodies of the invention to provide an additive or synergistic therapeutic effect. In another embodiment, the composition may comprise one or more (e.g., 2, 3, etc.) antibodies of the invention and one or more (e.g., 2, 3, etc.) additional antibodies against RSV, MPV or both RSV and MPV. Further, the administration of antibodies of the invention together with antibodies specific to other pathogens, for example, influenza A or influenza B virus, are within the scope of the invention. The antibodies of the invention can be administered either combined/simultaneously or at separate times from antibodies of specific to pathogens other than RSV or MPV.

In another embodiment, the invention provides a pharmaceutical composition comprising two or more antibodies, wherein the first antibody is an antibody of the invention as described herein and the second antibody is specific for RSV, MPV or both RSV and MPV or a different pathogen that may have co-infected the subject to whom the pharmaceutical composition is being administered.

Examples of antibodies of the invention specific for, and that neutralize RSV, MPV and PVM include, but are not limited to, HMB3210 variant 3, HMB3210 variant 1, HMB3210 variant 2, HMB3210 variant 4, HMB3210 variant 5, HMB3210 variant 6, HMB2430 variant 1, HMB2430 variant 2, HMB2430 variant 3, HMB2430 variant 4 or HMB2430 variant 5.

In one embodiment, the invention provides a pharmaceutical composition comprising the antibody HMB3210 variant 1 or an antigen binding fragment thereof, and a pharmaceutically acceptable carrier. In another embodiment, the invention provides a pharmaceutical composition comprising the antibody HMB3210 variant 2 or an antigen binding fragment thereof, and a pharmaceutically acceptable carrier. In another embodiment, the invention provides a pharmaceutical composition comprising the antibody HMB3210 variant 3 or an antigen binding fragment thereof, and a pharmaceutically acceptable carrier. In another embodiment, the invention provides a pharmaceutical composition comprising the antibody HMB3210 variant 4 or an antigen binding fragment thereof, and a pharmaceutically acceptable carrier. In another embodiment, the invention provides a pharmaceutical composition comprising the antibody HMB3210 variant 5 or an antigen binding fragment thereof, and a pharmaceutically acceptable carrier. In another embodiment, the invention provides a pharmaceutical composition comprising the antibody HMB3210 variant 6 or an antigen binding fragment thereof, and a pharmaceutically acceptable carrier.

In yet another embodiment, the invention provides a pharmaceutical composition comprising the antibody HMB2430 variant 1 or an antigen binding fragment thereof, and a pharmaceutically acceptable carrier. In another embodiment, the invention provides a pharmaceutical composition comprising the antibody HMB2430 variant 2 or an antigen binding fragment thereof, and a pharmaceutically acceptable carrier. In another embodiment, the invention provides a pharmaceutical composition comprising the antibody HMB2430 variant 3 or an antigen binding fragment thereof, and a pharmaceutically acceptable carrier. In another embodiment, the invention provides a pharmaceutical composition comprising the antibody HMB2430 variant 4 or an antigen binding fragment thereof, and a pharmaceutically acceptable carrier. In another embodiment, the invention provides a pharmaceutical composition comprising the antibody HMB2430 variant 5 or an antigen binding fragment thereof, and a pharmaceutically acceptable carrier.

Antibodies of the invention may be administered (either combined or separately) with other therapeutics e.g., with chemotherapeutic compounds, with radiotherapy, etc. In one embodiment, the therapeutic compounds include anti-viral compounds such as Tamiflu™. Such combination therapy provides an additive or synergistic improvement in therapeutic efficacy relative to the individual therapeutic agents when administered alone. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

Antibodies may be administered to those subjects who have previously shown no response, i.e., have been shown to be refractive to treatment for RSV or MPV infection. Such treatment may include previous treatment with an anti-viral agent. This may be due to, for example, infection with an anti-viral resistant strain of RSV, MPV or both RSV and MPV.

In one embodiment, a composition of the invention may include antibodies of the invention, wherein the antibodies may make up at least 50% by weight (e.g., 60%, 70%, 75%, 80%, 85%, 90%, 95%, 97%, 98%, 99% or more) of the total protein in the composition. In such a composition, the antibodies are in purified form.

The invention provides a method of preparing a pharmaceutical composition comprising the steps of: (i) preparing an antibody of the invention; and (ii) admixing the purified antibody with one or more pharmaceutically-acceptable carriers.

In another embodiment, a method of preparing a pharmaceutical composition comprises the step of: admixing an antibody with one or more pharmaceutically-acceptable carriers, wherein the antibody is a monoclonal antibody that was obtained from a transformed B cell or a cultured plasma cell of the invention. Thus the procedures for first obtaining the monoclonal antibody and then preparing the pharmaceutical can be performed at very different times by different people in different places (e.g., in different countries).

As an alternative to delivering antibodies or B cells for therapeutic purposes, it is possible to deliver nucleic acid (typically DNA) that encodes the monoclonal antibody (or active fragment thereof) of interest derived from the B cell or the cultured plasma cells to a subject, such that the nucleic acid can be expressed in the subject in situ to provide a desired therapeutic effect. Suitable gene therapy and nucleic acid delivery vectors are known in the art.

Compositions of the invention may be immunogenic compositions, and in some embodiments may be vaccine compositions comprising an antigen comprising an epitope recognized by an antibody of the invention or an antigen binding fragment thereof. Vaccines according to the invention may either be prophylactic (i.e., prevent infection) or therapeutic (i.e., treat or ameliorate infection).

Compositions may include an antimicrobial, particularly if packaged in a multiple dose format. They may comprise detergent e.g., a Tween (polysorbate), such as Tween 80. Detergents are generally present at low levels e.g., less than 0.01%. Compositions may also include sodium salts (e.g., sodium chloride) to give tonicity. A concentration of 10±2 mg/ml NaCl is typical.

Further, compositions may comprise a sugar alcohol (e.g., mannitol) or a disaccharide (e.g., sucrose or trehalose) e.g., at around 15-30 mg/ml (e.g., 25 mg/ml), particularly if they are to be lyophilized or if they include material which has been reconstituted from lyophilized material. The pH of a composition for lyophilisation may be adjusted to between 5 and 8, or between 5.5 and 7, or around 6.1 prior to lyophilisation.

The compositions of the invention may also comprise one or more immunoregulatory agents. In one embodiment, one or more of the immunoregulatory agents include(s) an adjuvant.

The epitope compositions of the invention may elicit both a cell mediated immune response as well as a humoral immune response in order to effectively address RSV and MPV infection. This immune response may induce long lasting (e.g., neutralizing) antibodies and a cell mediated immunity that can quickly respond upon exposure to RSV or MPV or both RSV and MPV.

Medical Treatments and Uses

The antibodies and antibody fragments of the invention or derivatives and variants thereof may be used for the treatment of RSV or MPV infection or co-infection with both RSV and MPV; for the prevention of infection of RSV or MPV or both RSV and MPV; or for the diagnosis of RSV or MPV infection.

Methods of diagnosis may include contacting an antibody or an antibody fragment with a sample. Such samples may be tissue samples taken from, for example, nasal passages, sinus cavities, salivary glands, lung, liver, pancreas, kidney, ear, eye, placenta, alimentary tract, heart, ovaries, pituitary, adrenals, thyroid, brain or skin. The methods of diagnosis may also include the detection of an antigen/antibody complex.

The invention therefore provides (i) an antibody, an antibody fragment, or variants and derivatives thereof according to the invention, (ii) an immortalized B cell clone according to the invention, (iii) an epitope capable of binding an antibody of the invention or (iv) a ligand, preferably an antibody, capable of binding an epitope that binds an antibody of the invention for use in therapy.

The invention also provides a method of treating a subject comprising administering to the subject an antibody, an antibody fragment, or variants and derivatives thereof according to the invention, or, a ligand, preferably an antibody, capable of binding an epitope that binds an antibody of the invention. In one embodiment, the method results in reduced RSV or MPV infection in the subject. In another embodiment, the method prevents, reduces the risk or delays of RSV or MPV infection in the subject.

The invention also provides the use of (i) an antibody, an antibody fragment, or variants and derivatives thereof according to the invention, (ii) an immortalized B cell clone according to the invention, (iii) an epitope capable of binding an antibody of the invention, (iv) a ligand, preferably an antibody, that binds to an epitope capable of binding an antibody of the invention, or (v) a pharmaceutical composition of the invention in (i) the manufacture of a medicament for the treatment or attenuation of infection by RSV or MPV or both RSV and MPV, (ii) a vaccine, or (iii) diagnosis of RSV and MPV infection.

The invention provides a composition of the invention for use as a medicament for the prevention or treatment of RSV or MPV infection. It also provides the use of an antibody of the invention and/or a protein comprising an epitope to which such an antibody binds in the manufacture of a medicament for treatment of a subject and/or diagnosis in a subject. It also provides a method for treating a subject, comprising the step of administering to the subject a composition of the invention. In some embodiments the subject may be a human. One way of checking efficacy of therapeutic treatment involves monitoring disease symptoms after administration of the composition of the invention. Treatment can be a single dose schedule or a multiple dose schedule.

In one embodiment, an antibody, antibody fragment, immortalized B cell clone, epitope or composition according to the invention is administered to a subject in need of such treatment. Such a subject includes, but is not limited to, one who is particularly at risk of or susceptible to RSV or MPV infection, including, for example, an immunocompromised subject. The antibody or antibody fragment of the invention can also be used in passive immunization or active vaccination.

Antibodies and fragments thereof as described in the present invention may also be used in a kit for the diagnosis of RSV or MPV infection. Further, epitopes capable of binding an antibody of the invention may be used in a kit for monitoring the efficacy of vaccination procedures by detecting the presence of protective anti-RSV or anti-MPV antibodies. Antibodies, antibody fragment, or variants and derivatives thereof, as described in the present invention may also be used in a kit for monitoring vaccine manufacture with the desired immunogenicity.

The invention also provides an epitope that specifically binds to an antibody of the invention or an antigen binding fragment thereof, for use (i) in therapy, (ii) in the manufacture of a medicament for the treatment or attenuation of RSV or MPV or both RSV and MPV infection, (iii) as a vaccine, or (iv) in screening for ligands able to neutralize RSV or MPV or both RSV and MPV infection.

The invention also provides a method of preparing a pharmaceutical, comprising the step of admixing a monoclonal antibody with one or more pharmaceutically-acceptable carriers, wherein the monoclonal antibody is a monoclonal antibody that was obtained from a transfected host cell of the invention. Thus the procedures for first obtaining the monoclonal antibody (e.g., expressing it and/or purifying it) and then admixing it with the pharmaceutical carrier(s) can be performed at very different times by different people in different places (e.g., in different countries).

Starting with a transformed B cell or a cultured plasma cell of the invention, various steps of culturing, sub-culturing, cloning, sub-cloning, sequencing, nucleic acid preparation etc. can be performed in order to perpetuate the antibody expressed by the transformed B cell or the cultured plasma cell, with optional optimization at each step. In one embodiment, the above methods further comprise techniques of optimization (e.g., affinity maturation or optimization) applied to the nucleic acids encoding the antibody. The invention encompasses all cells, nucleic acids, vectors, sequences, antibodies etc. used and prepared during such steps.

In all these methods, the nucleic acid used in the expression host may be manipulated to insert, delete or alter certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g., 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g., labels) or can introduce tags (e.g., for purification purposes). Mutations can be introduced in specific sites or can be introduced at random, followed by selection (e.g., molecular evolution). For instance, one or more nucleic acids encoding any of the CDR regions, heavy chain variable regions or light chain variable regions of antibodies of the invention can be randomly or directionally mutated to introduce different properties in the encoded amino acids. Such changes can be the result of an iterative process wherein initial changes are retained and new changes at other nucleotide positions are introduced. Further, changes achieved in independent steps may be combined. Different properties introduced into the encoded amino acids may include, but are not limited to, enhanced affinity.

General

As used herein, the terms "antigen binding fragment," "fragment," and "antibody fragment" are used interchangeably to refer to any fragment of an antibody of the invention that retains the antigen-binding activity of the antibody. Examples of antibody fragments include, but are not limited to, a single chain antibody, Fab, Fab', F(ab')$_2$, Fv or scFv. Further, the term "antibody" as used herein includes both antibodies and antigen binding fragments thereof.

As used herein, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used alone, or in combination, as prophylactic or therapeutic agents upon appropriate formulation, in association with active vaccination, as a diagnostic tool, or as a production tool as described herein.

The term "comprising" encompasses "including" as well as "consisting" e.g., a composition "comprising" X may consist exclusively of X or may include something additional e.g., X+Y.

The word "substantially" does not exclude "completely" e.g., a composition which is "substantially free" from Y may be completely free from Y. Where necessary, the word "substantially" may be omitted from the definition of the invention.

The term "about" in relation to a numerical value x means, for example, x±5%, or x±7%, or x±10%, or x±12%, or x±15%, or x±20%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a subject or patient is intended to include prevention, prophylaxis, attenuation, amelioration and therapy. The terms "subject" or "patient" are used interchangeably herein to mean all mammals including humans. Examples of subjects include humans, cows, dogs, cats, horses, goats, sheep, pigs, and rabbits. In one embodiment, the patient is a human.

EXAMPLES

Exemplary embodiments of the present invention are provided in the following examples. The following examples are presented only by way of illustration and to assist one of ordinary skill in using the invention. The examples are not intended in any way to otherwise limit the scope of the invention.

Example 1

Isolation and Characterization of Monoclonal Antibodies from Human Memory B Cells Able to Cross-Neutralize Both RSV and MPV From a cohort of 125 blood donors we selected 7 donors showing high serum antibody titers against RSV and MPV. CD22+ IgG+ B cells were sorted from cryopreserved peripheral blood mononuclear cells (PBMCs) and immortalized at 3 to 5 cells/well using Epstein Barr Virus (EBV) and CpG oligodeoxynucleotide 2006 and irradiated allogeneic PBMCs as feeder cells. Culture supernatants were harvested after 14 days and analyzed for the presence of neutralizing antibodies using a microneutralization assay based on infection of Hep-2 cells by RSV strain A2 or of LLC-MK2 cells by MPV A1 I-PV-03/01-6621 strain. Neat supernatants were incubated with 50-100 TCID$_{50}$ of viruses for 1 hour at room temperature prior to addition of Hep-2 or LLC-MK2 target cells which were incubated for 6 or 8 days, respectively. Viable cells were then detected with a spectrophotometer by adding to the cultures the WST-1 reagent (Roche) for 3 to 4 hours.

From three independent experiments, 36 monoclonal antibodies (mAbs) that neutralized MPV (FIG. 1, left panel) were isolated; and from five independent experiments, 136 mAbs that neutralized RSV (FIG. 1, right panel) were isolated. A secondary screening was then performed to test whether the isolated mAbs were able to neutralize both MPV and RSV. Using this strategy two mAbs isolated from the same donor (Don. 5) were found to cross-neutralize RSV and MPV: (i) HMB2430, which was initially selected based on neutralization of RSV, and (ii) HMB3210, which was initially selected based on neutralization of MPV.

The VH and VL genes of HMB2430 and HMB3210 were cloned into IgG1 expression vectors and recombinant mAbs were produced by transient transfection of 293 Freestyle cells (293F). Supernatants from transfected cells were collected after 10 days of culture and IgG were affinity purified by Protein A chromatography. The two mAbs shared most V and J gene fragments (IGHV3-21*01, IGHJ4*02, IGLV1-40*01 and IGLJ1*01), according to the homology analysis performed using the IMGT database, but differed in the N regions in the IGHD usage (D3-10*01 and D5-24*01 for HMB2430 and HMB3210, respectively) and in the pattern of somatic mutations, and were therefore considered not clonally related.

Figure 2:
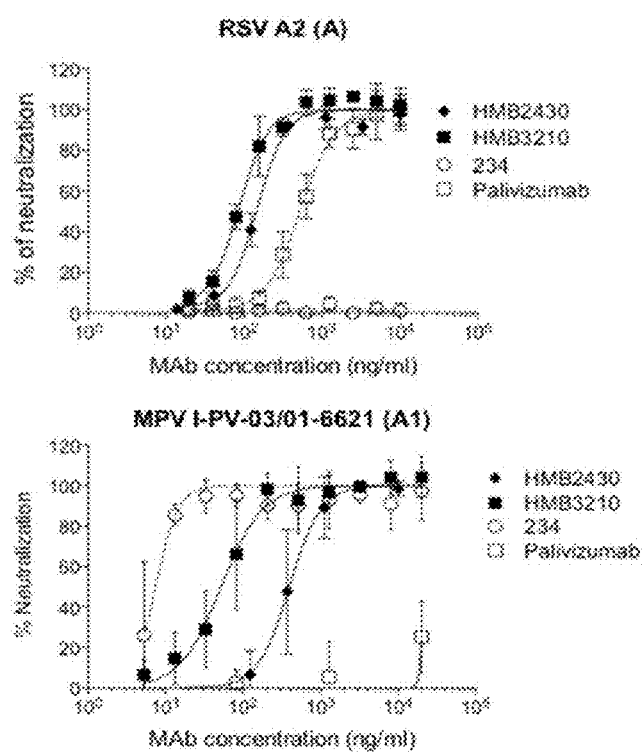
FIG. 2 shows the results of neutralization of RSV and MPV by monoclonal antibodies HMB2430, HMB3210, 234 mAb and Palivizumab.

The half maximal inhibitory concentration (IC50) of HMB2430 and HMB3210 was determined using the microneutralization assay described above with 100 tissue culture infective dose 50 (TCID50) of virus. IC50 values were calculated by interpolation of neutralization curves fitted with a 4-parameter nonlinear regression with a variable slope. The results of the analysis are shown in FIG. 2 and Table 4.

TABLE 4

| Viruses (group) | mAbs IC50 (ng/ml) | | | |
|---|---|---|---|---|
| | HMB2430 | HMB3210 | Palivizumab | 234 |
| RSV A2 (A) | 146 | 86 | 524 | >20000 |
| MPV I-PV 03/01-6621 (A1) | 393 | 52 | >20000 | 7 |

Example 2

Breadth of Reactivity to all RSV and MPV Groups and Sub-Groups

In order to evaluate the breath of reactivity of HMB2430 and HMB3210, purified mAbs were tested by FACS for binding to Hep-2 RSV-infected cells or to LLC-MK2MPV-infected cells using the following RSV and MPV strains: RSV A2 (A, 1961 Australia; A/A2/61), RSV Long (A, Maryland US, 1956; A/Long/56), RSV Randall (A, Chicago US, 1958; A/Randall/58), RSV 9320 (B, Massachusetts US, 1977; B/9320/77), WV/14617/85 (B, Huntington West Va., 1985; B/14617/85), 18537 (B, Washington District of Columbia US, 1962; B/18537/62), MPV I-PV-03/01-6621 (A1, Pavia IT, 2001; A1/6621/01), MPV I-PV-02/06-8938 (A2, Pavia IT, 2006; A2/8938/06), I-PV-03/04-4702 (B1, Pavia IT, 2004; B1/4702/04) and I-PV-02/04-3817 (B2, Pavia IT, 2004; B2/3817/04). In parallel, three previously described mAbs were tested: (i) Motavizumab, RSV-specific; (ii) mAb 234, MPV-specific; and (iii) FO32, Influenza A-specific (used as negative control). All mAbs were tested for binding to infected or uninfected cells at 10 µg/ml. HMB2430 and HMB3210 reacted with all 6 RSV and all 4 MPV strains tested, representative of the known RSV and MPV groups and sub-groups (Table 5). In contrast, Motavizumab reacted with all the 6 RSV strains tested, but did not react with any of the 4 MPV strains tested. Conversely, 234 mAb reacted will all 4 MPV strains tested but did not react with any of the 6 RSV strains tested.

TABLE 5

Staining of Hep-2 or LLC-MK2 cells infected by different strains of RSV or MPV, respectively, by FO32 (negative control), Motavizumab, 234, HMB2430 and HMB3210, as measured by flow cytometry.

| Virus | Monoclonal Antibody (10 µg/ml) | | | | |
|---|---|---|---|---|---|
|  | FO32 | Motavizumab | mAb 234 | HMB2430 | HMB3210 |
| RSV A/A2/61 | − | + | − | + | + |
| RSV A/Long/56 | − | + | − | + | + |
| RSV A/Randall/58 | − | + | − | + | + |
| RSV B/18537/62 | − | + | − | + | + |
| RSV B/14617/85 | − | + | − | + | + |
| RSV B/9320/77 | − | + | − | + | + |
| MPV A1/6621/01 | − | − | + | + | + |
| MPV A2/8938/06 | − | − | + | + | + |
| MPV B1/4702/04 | − | − | + | + | + |
| MPV B2/3817/04 | − | − | + | + | + |
| Mock LLC-MK2 | − | − | − | − | − |
| Mock Hep-2 | − | − | − | − | − |

(−) <5% stained cells
(+) >50% stained cells

Example 3

Figure 3:
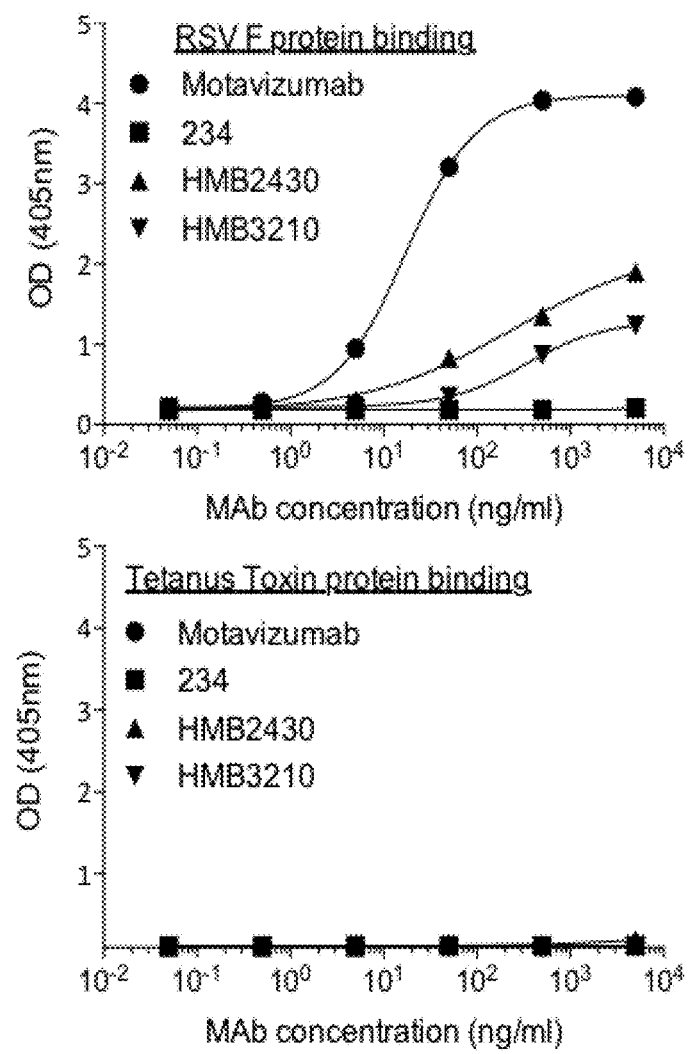
FIG. 3 shows the binding to RSV F or Tetanus Toxin protein by monoclonal antibodies Motavizumab, 234 mAb, HMB2430 and HMB3210 as measured by ELISA.

Binding to Recombinant F Protein of RSV and MPV by ELISA and by Staining of Transfected Cells In order to identify the target antigen recognized by HMB2430 and HMB3210 on RSV and MPV viruses, we analyzed the two mAbs; in parallel with Motavizumab and mAb 234, for their ability to bind to a homotrimeric soluble F protein of RSV (A2 strain) that was produced from transiently transfected 293F cells. As shown in FIG. 3, both HMB2430 and HMB3210 reacted specifically with RSV F protein by ELISA and showed a distinct binding profile as compared to Motavizumab. In addition, HM2430 and HMB3210 stained intracellularly 293F cells transiently transfected with mammalian expression vectors encoding for the full length F protein from either RSV (A2 strain) or MPV (NL/1/99 B1 strain) (Table 6), indicating that HMB2430 and HMB3210 recognize a shared epitope present on both RSV and MPV F proteins. This finding is particularly striking considering that RSV and MPV F proteins have only 33-35% amino acid sequence identity. As expected Palivizumab and Motavizumab bound to cells expressing the RSV F protein but not to those expressing the MPV F protein (Table 6). Conversely, 234 mAb bound to cells expressing the MPV F protein but not to cells expressing the RSV F protein (Table 6).

TABLE 6

Staining of untransfected 293F cells or 293F cells transfected with RSV or MPV F protein, as measured by flow cytometry

| Antibody (10 µg/ml) | 293F + RSV F (A/A2/61;A) | 293F + MPV F (NL/1/99;B1) | 293F untransfected |
|---|---|---|---|
| HMB3210 | + | + | − |
| HMB2410 | + | + | − |
| Palivizumab | + | − | − |
| Motavizumab | + | − | − |
| 234 | − | + | − |

(−) <5% stained cells
(+) >50% stained cells

Example 4

Epitope Mapping by Using an Inhibition Binding Assay on RSV Infected Cells

Figure 4:
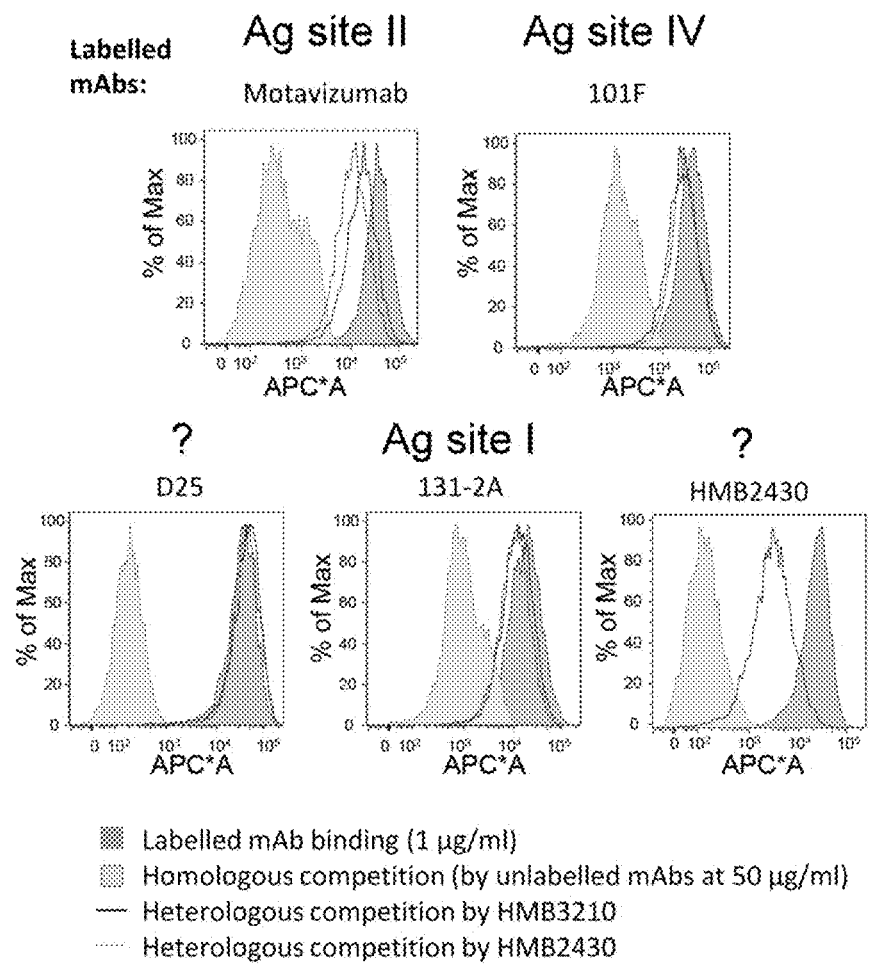
FIG. 4 shows the binding of labeled monoclonal antibodies to RSV-infected Hep-2 cells in the presence of large excess of the indicated unlabeled antibodies.

In order to gain insight into the F protein epitope recognized by HMB2430 and HMB3210, we set up an inhibition of binding assay using Hep-2 cells infected with RSV A2 strain. The following panel of RSV F protein-specific mAbs were purchased or produced by gene synthesis: (i) Motavizumab, specific for the antigenic site II; (ii) 101F, specific for the antigenic site IV; (iii) D25 of undefined specificity; (iv) 131-2a, specific for the antigenic site I. The mAbs were labeled with biotin and tested for binding to Hep-2 infected cells to determine the optimal concentration of mAb required to achieve 70-80% maximal binding. The biotin-labeled mAbs were then used as probes to assess whether their binding (measured using fluorophore-conjugated streptavidin) was inhibited by pre-incubation of RSV A2-infected cells with a 50 fold excess of homologous or heterologous unlabeled mAbs. As expected, binding of biotin-labeled HMB2430 was blocked by preincubating the cells with unlabeled HMB2430, but it was also partially blocked by unlabeled HMB3210 (FIG. 4). In contrast, binding of all the other biotin-labeled mAbs tested was not prevented by pre-incubation with either HMB2430 or HMB3210 (FIG. 4). Taken together these results indicate that HMB2430 and HMB3210 recognize partially overlapping epitopes on the F protein that are shared in RSV and MPV and that these epitopes are distinct from the epitopes in the F protein antigenic site II (recognized by Motavizumab and Palivizumab), antigenic site IV (recognized by mAb 101F), and antigenic site I (recognized by mAb 131-2A). In addition, the epitopes recognized by mAbs HMB2430 and HMB3210 on the RSV F protein are distinct from the unknown epitope recognized by the mAb D25.

Example 5

Monoclonal Antibody Reactivity with the RSV and MPV F Proteins Under Reducing and Non-Reducing Conditions To further confirm the finding that HMB2430 and HMB3210 recognize the F protein of both RSV and MPV, we tested the two mAbs for their ability to stain RSV and MPV F proteins in Western blot. Hep-2 cells were infected with RSV and LLC-MK2 cells with MPV, lysed with a mild detergent and run on SDS-PAGE gel under reducing or non-reducing conditions. Proteins were then transferred on a PVDF membrane which was then incubated with either HMB2430, HMB3210, Motavizumab or 234 mAb. MAb binding was detected with an anti-human HRP-conjugated antibody in combination with the ECL Western Blotting Detection reagent. HMB2430 and HMB3210 bound to F protein derived from RSV-infected cells (FIG. 5) and MPV-infected cells (FIG. 6) under non-reducing conditions. The MPV-specific mAb 234 (that recognizes an epitope on the MPV F protein which correspond to the antigenic site II on RSV F protein) bound to MPV F protein under non-reducing conditions, but did not bind to RSV F protein. In contrast, the RSV-specific mAb Motavizumab bound to the RSV F protein both under reducing and non-reducing conditions, confirming the recognition of a largely linear epitope. These results suggest that, differently from Motavizumab and Palivizumab, HMB2430 and HMB3210 recognize conformational epitopes which also relies on the presence of disulphide bonds between amino acid residues on the RSV and MPV F proteins.

Example 6

Neutralization of all RSV and MPV Groups and Sub-Groups by HMB2430 and HMB3210

Purified HMB2430 and HMB3210 mAbs were tested for their ability to neutralize RSV or MPV infection of Hep-2 or LLC-MK2 cells, respectively. The following RSV and MPV strains were tested: RSV A2 (A, 1961 Australia; A/A2/61), RSV Long (A, Maryland US, 1956; A/Long/56), RSV Randall (A, Chicago US, 1958; A/Randall/58), RSV 9320 (B, Massachusetts US, 1977; B/9320/77), WV/14617/85 (B, Huntington W. Va., 1985; B/14617/85), 18537 (B, Washington District of Columbia US, 1962; B/18537/62), RSV 9727/2009 (B, Pavia IT, 2009; B/9727/09), RSV 9736/2009 (B, Pavia IT, 2009; B/9736/09), RSV 9847/2009 (B, Pavia IT, 2009; B/9847/09), MPV I-PV-03/01-6621 (A1, Pavia IT, 2001; A1/6621/01), MPV I-PV-02/06-8938 (A2, Pavia IT, 2006; A2/8938/06), I-PV-02/06-8908 (A2, Pavia IT, 2006; A2/8908/06), I-PV-02/06-8909 (A2, Pavia IT, 2006; A2/8909/06), I-PV-03/04-4702 (B1, Pavia IT, 2004; B1/4702/04) and I-PV-02/04-3817 (B2, Pavia IT, 2004; B2/3817/04).

In the same experiment HMB2430 and HMB3210 were compared to Palivizumab (RSV-specific) and 234 mAb (MPV-specific). HMB3210 neutralized all 11 RSV and all 6 MPV strains tested, representative of the known RSV and MPV groups and sub-groups (Table 7). HMB2430 neutralized all 11 RSV strains tested and all the A1 and A2 MPV strains tested but not the B1 or B2 MPV strains tested. As expected, Palivizumab neutralized all the 11 RSV strains tested, but none of the 6 MPV strains tested while 234 mAb neutralized all 6 MPV strains tested but none of the 11 RSV strains tested.

HMB3210 and HMB2430 potently neutralized all 11 RSV strains tested (mean IC50 values, 0.070 and 0.133 μg/ml, respectively. This values were on average 5.4 and 2.6 fold higher than the IC50 value of Palivizumab (0.284 μg/ml). HMB3210 potently neutralized all 6 MPV strains tested (IC50 mean value 0.113 μg/ml) that is on average 1.7 fold lower than the IC50 value of 234 (0.046 μg/ml).

TABLE 7

Neutralization of RSV and MPV strains

| | Neutralization IC50 (μg/ml) | | | |
|---|---|---|---|---|
| Virus | Palivizumab | mAb 234 | HMB2430 | HMB3210 |
| RSV A/A2/61 | 0.617 | — | 0.350 | 0.184 |
| RSV A/Long/56 | 0.599 | — | 0.361 | 0.187 |
| RSV A/Randall/58 | 0.440 | — | 0.179 | 0.116 |
| RSV A/9846/09 | 0.283 | — | 0.123 | 0.06 |
| RSV A/9835/09 | 0.284 | — | 0.076 | 0.063 |
| RSV B/18537/62 | 0.143 | — | 0.094 | 0.034 |
| RSV B/14617/85 | 0.129 | — | 0.096 | 0.038 |
| RSV B/9727/09 | 0.275 | — | 0.084 | 0.051 |
| RSV B/9320/77 | 0.069 | — | 0.021 | 0.012 |
| RSV B/9736/09 | 0.092 | — | 0.027 | 0.007 |
| RSV B/9847/09 | 0.209 | — | 0.053 | 0.026 |
| MPV A1/6621/01 | — | 0.040 | 0.744 | 0.071 |
| MPV A2/8938/06 | — | 0.044 | 1.049 | 0.045 |
| MPV A2/8908/06 | — | 0.057 | 2.795 | 0.066 |
| MPV A2/8909/06 | — | 0.012 | 0.161 | 0.007 |
| MPV B1/4702/04 | — | 0.019 | — | 0.029 |
| MPV B2/3817/04 | — | 0.106 | — | 0.465 |

Example 7

Lack of Selection of RSV and MPV Viral Escape Mutants

HMB3210, Palivizumab and 234 mAb were tested for their ability to select RSV or MPV Monoclonal Antibody Resistant Mutants (MARMs) in vitro. In spite of several attempts, HMB3210 failed to select any RSV or MPV MARMs when tested against 32×10e6 RSV A/Long/58 TCID50 and against 16×10e6 MPV A1/6621/01 TCID50. In contrast, Palivizumab selected MARMs with high frequency (a total of 85 independent Palivizumab MARMs were isolated from an input of 16×–10e6 RSV A/Long/58 TCID50 that corresponded to a frequency of 1 in 185,000 TCID50). MAb 234 under the same experimental conditions did not select any MPV MARMs. The difficulty to isolate 234 mAb MARMs is consistent with the report by Ulbrandt et al. (J General Virol 2008) that showed that a high level of virus was required to isolate a small number of MARMs. Escaped viruses were mapped to a mutation K242N using the NL/1/99 MPV B1 isolate. Independent Palivizumab MARMs (PZ-MARMs) were collected and the F protein of 10 of them was fully sequenced (Table 8). PZ-MARM2, PZ-MARM3, PZ-MARM4, PZ-MARM5, PZ-MARM6, PZ-MARM8 and PZ-MARM10 shared the same two amino acid mutations (P101S/K272T); PZ-MARM1 had also two amino acid mutations in the same position but with a different amino acid change (P101S/K272Q); PZ-MARM7 had a single amino acid mutation (K272N) again at position 272; finally, PZ-MARM9 had a mutation in common with other PZ-MARMs and a unique mutation at position 262 (P101S/N262Y). Point mutations in this region (nucleotide position 827 and 828) were already described (Zhao et al. Virology 2004) and resulted in two different amino acid changes at position 272 (K272Q and K272M). The first mutation (i.e.

K272Q) was also present in the PZ-MARM1 here described. Viruses carrying these point mutations were completely resistant to the prophylactic effects of Palivizumab in cotton rats (Zhao et al. Virology 2004) and the same mutations along with others were described in RSV-infected immunosuppressed cotton rats treated prophylactically with Palivizumab.

Figure 7:
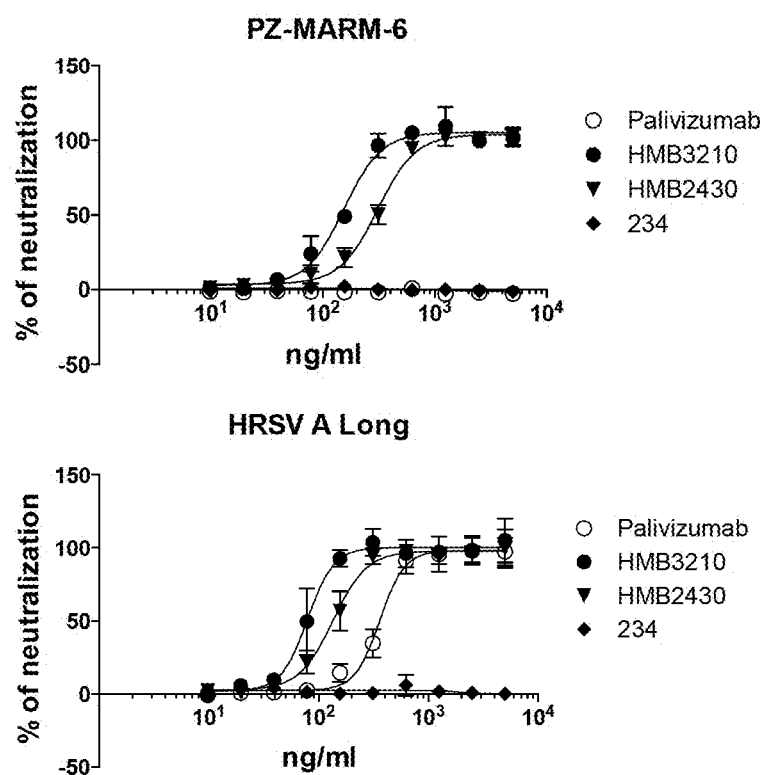
FIG. 7 shows the results of neutralization of RSV Long strain and the PZ-MARM6 isolate by monoclonal antibodies HMB2430, HMB3210, 234 mAb and Palivizumab.

HMB3210, HMB2430 and Palivizumab were then tested for their capacity to neutralize the PZ-MARM6 infection of Hep-2 cells. While Palivizumab did not neutralize the PZ-MARM6, HMB3210 and HMB2430 potently neutralized this virus to levels comparable with those observed with the corresponding wild type virus (FIG. 7).

Taken together, these results demonstrate that HMB3210 and HMB2430 did not select RSV or MPV MARMs in vitro. These results are consistent with the notion that the target epitopes recognized by HMB3210 and HMB2430 are extremely conserved and that mutations that abrogate antibody binding are either extremely rare or may be associated with loss of viral fitness.

TABLE 8

Amino acid variations in RSV MARMs selected with Palivizumab

| | aa position (nucleotide position) | | | | |
|---|---|---|---|---|---|
| | 101 (314) | 262 (797) | 272 (827) | 272 (828) | 272 (829) |
| RSV A/Long/56 | P | N | K | K | K |
| PZ-MARM1 | S (C to T) | | Q (A to C) | | |
| PZ-MARM2 | S (C to T) | | | T (A to C) | |
| PZ-MARM3 | S (C to T) | | | T (A to C) | |
| PZ-MARM4 | S (C to T) | | | T (A to C) | |
| PZ-MARM5 | S (C to T) | | | T (A to C) | |
| PZ-MARM6 | S (C to T) | | | T (A to C) | |
| PZ-MARM7 | P | | | | N (G to T) |
| PZ-MARM8 | S (C to T) | | | T (A to C) | |
| PZ-MARM9 | S (C to T) | Y (A to T) | | | |
| PZ-MARM10 | S (C to T) | | | T (A to C) | |

Example 8

Removal of a Glycosylation Site in LCDR3 does not Affect HMB3210 Activity

Figure 8:
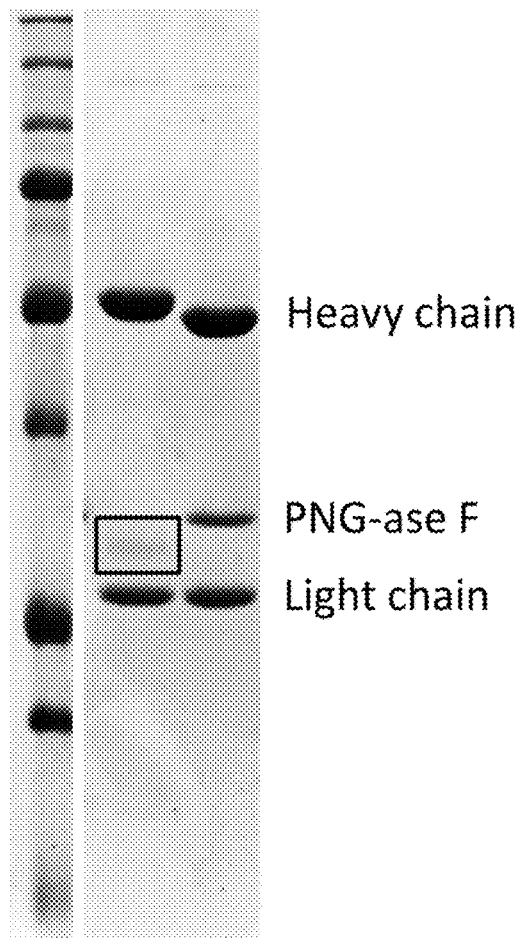
FIG. 8 shows the results of the analysis of HMB3210v2 on a reducing SDS-PAGE gel following incubation in the presence (+) or absence (−) of the N-glycosidase PNG-ase F. Highlighted with the black box is the minor fraction of the HMB3210 light chain which is glycosylated.
Figure 9:
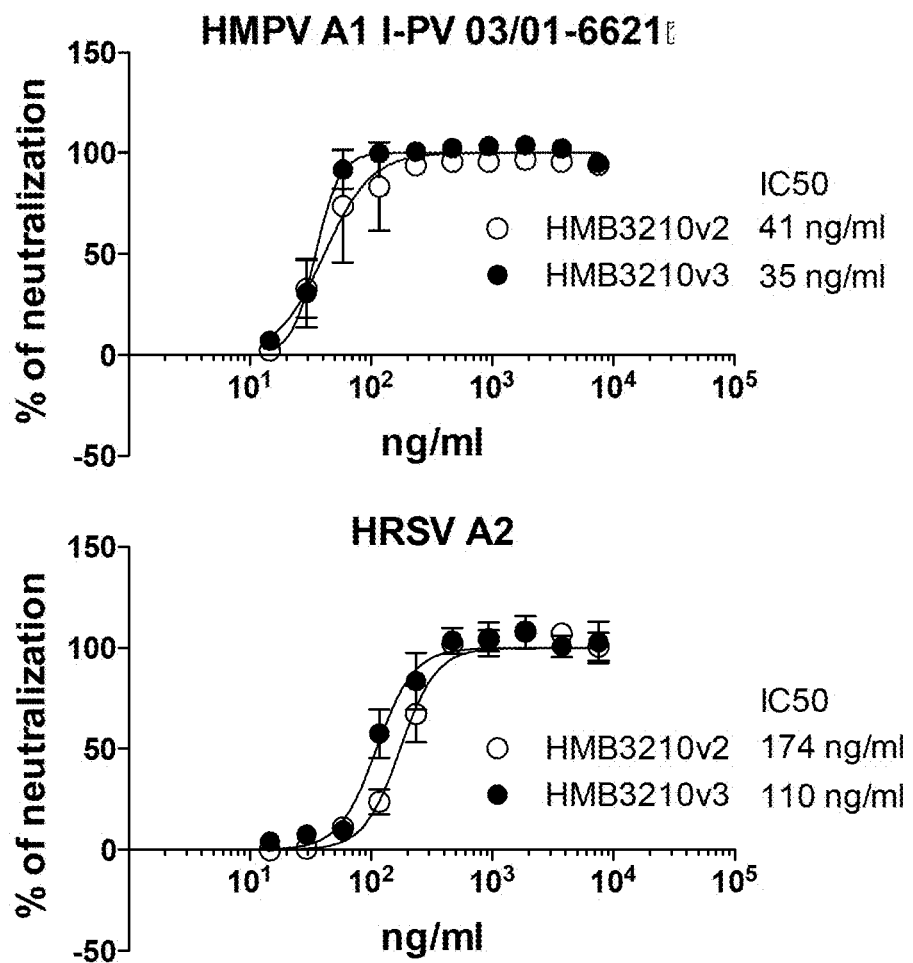
FIG. 9 shows the results of neutralization of MPV I-PV 03/01-6621 and RSV A2 by monoclonal antibodies HMB3210v2 and HMB3210v3.
Figure 10:
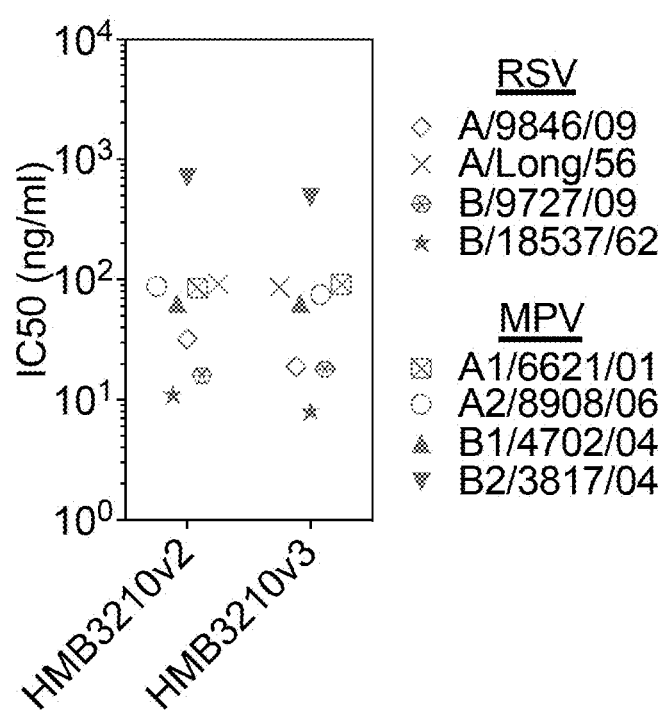
FIG. 10 shows the results of neutralization of a panel of MPV and RSV strains by monoclonal antibodies HMB3210v2 and HMB3210v3.

HMB3210 variable light chain has a N-glycosylation motif (NxS/T, where x can be any amino acid but proline) in the LCDR3 at position 113 (IMGT numbering). The asparagine at position 113 (N113) replaces a serine present in the germline sequence. The presence of glycosylation motifs in the variable region might have a positive or negative impact on the antibody activity and is recognized to be a cause of antibody heterogeneity. The presence of a glycan on the light chain of HMB3210 was assessed on a reducing SDS-PAGE gel following incubation in the presence or absence of the N-glycosidase PNG-ase F (FIG. 8). This analysis indicated that a minority of the light chain is indeed glycosylated. The N113 residue was then removed and the corresponding germline-encoded serine residue was restored. In parallel, another somatic mutation in framework −1 region of the light chain (P7T) was also removed to restore the germline-encoded proline residue at position 7 (IMGT numbering in the corresponding IGLV1—40*02 gene). A new HMB3210 variant (named HMB3210v3) made by HMB3210 heavy chain VH.2 (SEQ ID 17) and HMB3210 light chain VL.3 was then produced and tested for its neutralizing activity against RSV A2 and MPV I-PV 03/01-6621 strains in parallel with the HMB3210v2 (made by HMB3210 heavy chain VH.2 (SEQ ID NO: 17) and light chain VL SEQ ID NO: 14). This variant (HMB3210v3) showed a slightly improved neutralization against both RSV and MPV strains tested (FIG. 9), thus showing that the removal of the light chain glycosylation site does not affect binding to RSV and MPV target epitopes. The two antibody variants were then tested in parallel against a panel of RVS and MPV viruses and shown to have comparable activities against all viruses tested (FIG. 10). In conclusion, HMB3210v3 is not glycosylated in the variable light chain and is overall poorly mutated as compared to the germline heavy and light chain genes having only 8 amino acid somatic mutations in the heavy chain and 4 in the light chain: S58A (HCDR2), I65S (HCDR2), Y66D (HFR3), V71A (HFR3), N85T (HFR3), Y88F (HFR3), V101I (HFR3), Y103F (HFR3), G56D (LCDR2), S65N (LCDR2), G78A (LFR3) and S109R (LCDR3) (all positions were indicated according to the IMGT numbering).

Example 9

HMB3210 and HMB2430 Cross-Reactivity with MPV Relies on Somatic Mutations

Figure 11:
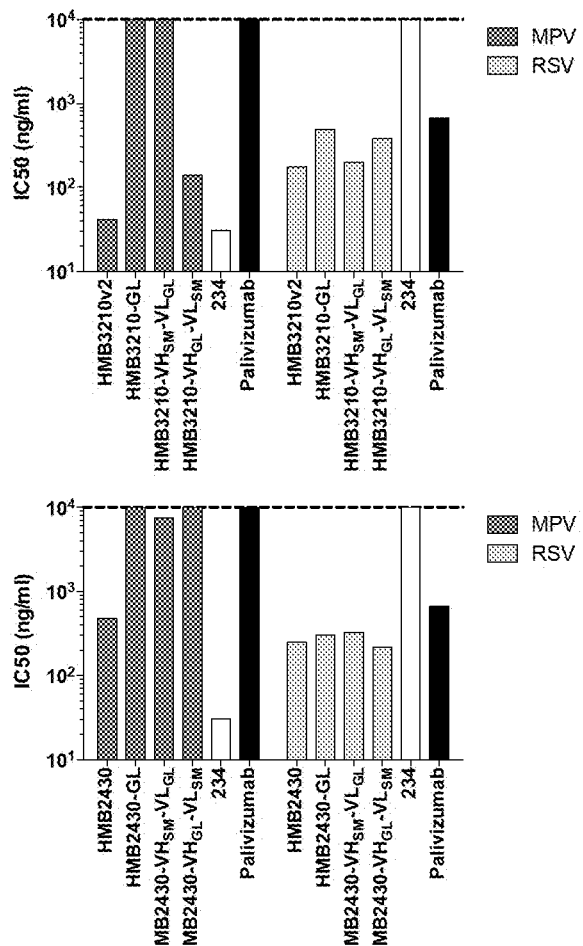
FIG. 11 shows the results of neutralization of MPV I-PV 03/01-6621 and RSV A2 by HMB3210 and HMB2430 monoclonal antibody germlined variants.

In order to gain insights into the role of somatic mutations in the cross-reactivity of HMB2430 and HMB3210 against RSV and MPV, the germlined versions of both mAbs were synthesized and tested for their capacity to neutralize RSV A2 and MPV I-PV 03/01-6621 strains. Both HMB2430 and HMB3210 germlined mAbs (HMB2430-GL and HMB3210-GL, respectively) were made of VH.3 and VL.2 in case of HMB2430-GL and of VH.3 and VL.4 in case of HMB3210-GL. Both germlined forms of the mAbs efficiently neutralized RSV to levels comparable to those observed with the original somatically mutated HMB3210 and HMB2430 (FIG. 11). However, HMB3210-GL and HMB2430-GL failed to neutralize MPV, thus indicating that somatic mutations are indispensable for MPV neutralization. To further understand whether somatic mutations of heavy or light chain are both responsible for neutralization of MPV, we produced antibodies carrying either the heavy or the light chain in the germline configuration: HMB2430-VHGL-VLSM made by VH.3 and VL; HMB2430-VHSM-VLGL made by VH.2 and VL.2; HMB3210-VHGL-VLSM made by VH.3 and VL; HMB3210-VHSM-VLGL made by VH.2 and VL.4. Removal of somatic mutations in the heavy chain of HMB3210 did not affect neutralization of RSV or MPV viruses, while removal of somatic mutations in the heavy chain of HMB2430 affected neutralization of MPV, albeit maintaining neutralization of RSV. Removal of somatic mutations in the light chain of both HMB2430 and HMB3210 abolished MPV neutralization, while not affecting RSV neutralization (FIG. 11). Taken together, these findings indicate that HMB3210 and HMB2430 were initially selected by RSV and subsequently developed, through the accumulation of somatic mutations, cross-reactivity against MPV. Overall only 3 somatic mutations in the light chain CDRs account for the acquisition of MPV cross-reactivity in a RSV-specific germlined antibody. Of note, HMB2430 and HMB3210 (not clonally related) share the same somatic mutation in LCDR3S to R at position 109.

Example 10

HMB3210 Recognition of Pre- and Post-Fusion F Protein Conformations

Figure 12:
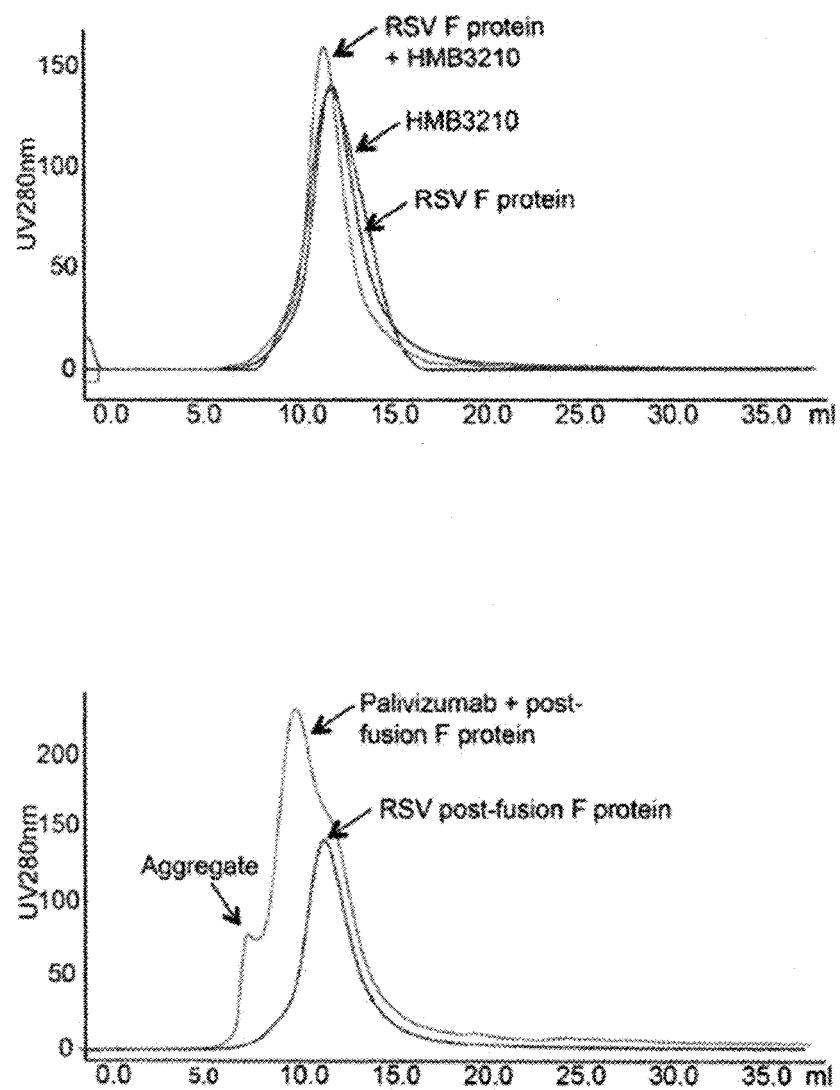
FIG. 12 shows the results of size exclusion chromatography analysis of the RSV F post-fusion recombinant protein co-incubated or not with HMB3210 or Palivizumab.

A DNA construct encoding RSV F residues 26-136 and 147-512 (corresponding to the F ectodomain without the fusion peptide of the RSV strain A2) with a C-terminal histidine tag was codon optimized and synthesized. Recombinant F was expressed using a baculovirus expression vector in Sf21 cells and purified from the supernatant by nickel affinity and size exclusion chromatography (SEC). A similar construct was already used by others (Swanson et al. PNAS 2011 and McLellan et al. J Virol 2011) to solve the crystal structure of the post-fusion F protein. The protein was analyzed under non-reducing conditions on an SDS-PAGE gel and gave a band at ≈65-70 kDa and when analyzed by SEC on a S200 column the "post-fusion" RSV F protein eluted as a symmetric peak with an apparent molecular weight of ≈150 kDa that corresponds to the MW of the trimeric F protein and overlaps with the elution volume of human IgG1 antibodies. The "post-fusion" F protein was incubated with either HMB3210 or Palivizumab and the two mixtures were run on a S200 column. The incubation of the "post-fusion" F protein with Palivizumab shifted the elution peak to a lower elution volume (corresponding to an apparent MW of ≈300 kDa) as compared to the F protein alone indicating that Palivizumab bound to the "post-fusion" F protein, as already reported. Of note, the incubation of HMB3210 with "post-fusion" F protein did not result in a shifting of the elution volume (FIG. 12). The fact that HMB3210 and the "post-fusion" F protein elute as independent molecules indicates that HMB3210, unlike Palivizumab, does not bind the "post-fusion" F protein.

Figure 13:
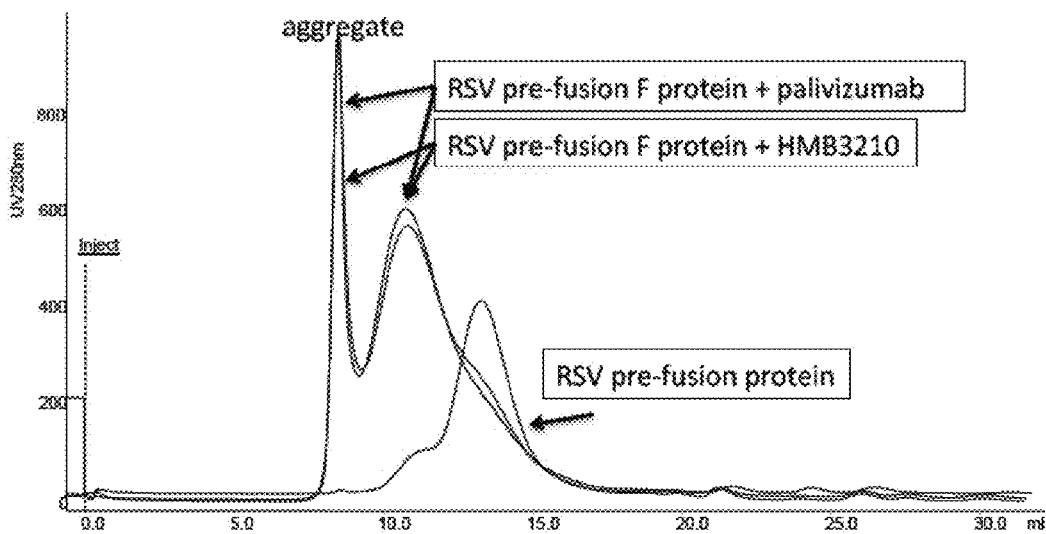
FIG. 13 shows the results of size exclusion chromatography analysis of the RSV F pre-fusion recombinant protein co-incubated or not with HMB3210 or Palivizumab.
Figure 14:
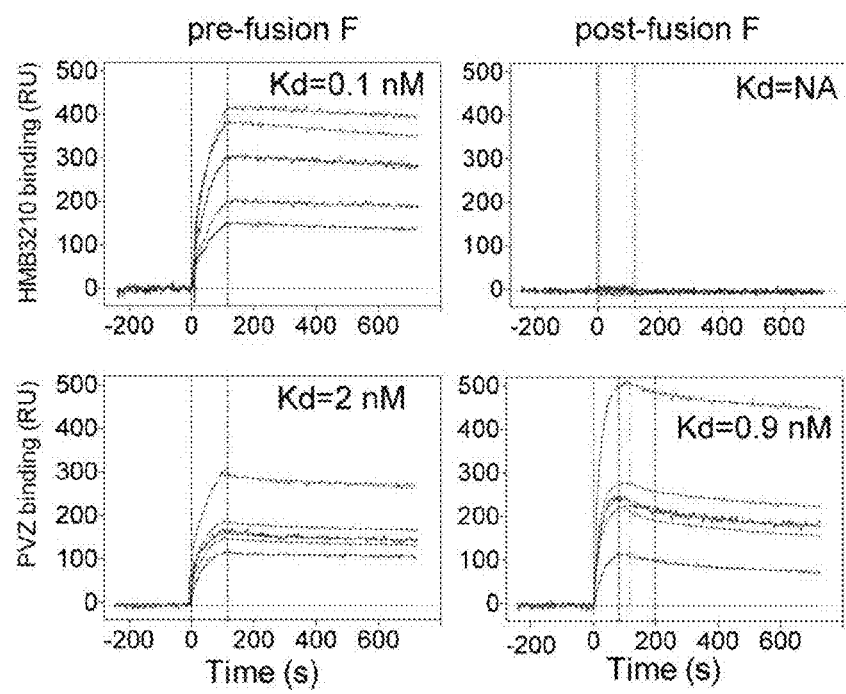
FIG. 14 shows the binding of HMB3210v3 or Palivizumab (PVZ) to the pre-fusion and post-fusion RSV F proteins as measured by surface plasmon resonance (SPR).

A stabilized form of the full-length pre-fusion RSV F protein was then synthesized following the strategy adopted by Magro et al. PNAS 2012 by substituting the 4 amino acid residues (L481, D489, S509 and D510) with cysteines and by substituting the 9 basic amino acid residues (R106, R108, R109, K131, K132, R133, R134, R135 and R136) at the two F protein cleavage sites with N residues to ablate the furine cleavage sites. The F protein sequence was additionally modified by the insertion of a TEV cleavage site after the transmembrane region, followed by GFP and a 6-His tag at the C-terminus to facilitate purification. The 4 introduced cysteines were positioned, according to the PIV-5 pre-fusion F structure, in a way that the formation of inter-monomeric disulphide bonds was possible only when the F protein was in the pre-fusion conformation, but not when refolded into the post-fusion structure, thus enabling the stabilization of the pre-fusion F protein. The stabilized pre-fusion F protein was described by Magro et al. to be heterogenous, since it also contains a proportion of molecules in which the additional cysteine residues were not disulphide bonded. The F protein construct here described was produced using a baculovirus expression vector in Sf21 cells, solubilized from cell membranes with a mild detergent and purified by nickel affinity and size exclusion chromatography. The purified pre-fusion F protein was analyzed by SEC on a S200 column and eluted as a symmetric peak with an apparent molecular weight of ≈150 kDa that correspond to the MW of the trimeric F protein and that overlaps with the elution volume of human IgG1. The incubation of the pre-fusion F protein with Palivizumab shifted the elution peak to a lower elution volume (corresponding to an apparent MW of ≈300 kDa) as compared to the F protein alone and also induced the formation of a high molecular weight complex that eluted in the void volume of the column that might be related to the formation of larger aggregates. A similar shift in the elution volume was also observed when HMB3210v2 was incubated with the pre-fusion protein (FIG. 13). These results indicate that Palivizumab bind to both the pre-fusion and post-fusion forms of the F protein, while HMB3210 selectively recognizes the pre-fusion form of the F protein. The two F proteins (pre- and post-fusion forms) were also tested by surface plasmon resonance (SPR). Palivizumab bound to both pre- and post-fusion proteins with similar affinities, while HMB3210v3 selectively bound to the pre-fusion F protein with high affinity (Kd constant of 0.1 nM as compared to the Palivizumab Kd of 2 nM) (FIG. 14).

Example 11

HMB3210v3 Cross-Neutralizes the Two Animal Paramyxoviruses Bovine Respiratory Syncytial Virus (BRSV) and Pneumonia Virus of Mice (PVM)

The breadth of reactivity of HMB3210 was also assessed on two other animal paramyxoviruses: BRSV and PVM, two viruses that share with RSV 81% and 40% amino acid identity in the F protein, respectively. HMB3210 was tested for its ability to neutralize PVM strain 15 and BRSV strain RB94 and shown to be effective against these viruses with IC50 values of 100 ng/ml and 10 ng/ml, respectively. These results indicate that in addition to the human paramyxoviruses RSV and MPV, HMB3210 is also effective against other two viruses of the paramyxoviridae family.

Example 12

Inhibition of Virus Spreading by HMB3210

Figure 15:
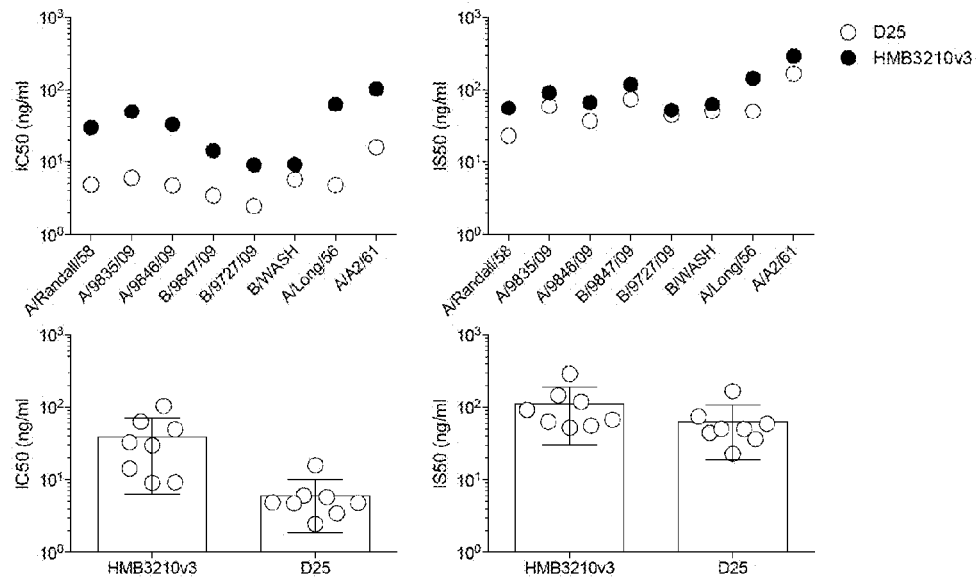
FIG. 15 shows the virus neutralization and inhibition of viral spreading by human monoclonal antibodies HMB3210v3 and D25.

We also measured the ability of HMB3210 and the D25 RSV-specific antibody to prevent cell-to-cell viral spread, which has been reported to be a distinct property of anti-RSV antibodies independent of the neutralizing activity. We infected Hep-2 cells with RSV A or B strains, added after 20 hours different concentrations of antibodies and examined the formation of syncytia on day 3 to determine the 50% antibody concentration inhibiting viral spread, here defined as IS50. Both antibodies were capable of inhibiting viral spread, but at higher concentrations. Interestingly, in this assay HMB3210 showed IS50 comparable to those of the more potent neutralizing antibody D25 (FIG. 15).

Example 13

Prophylactic and Therapeutic Efficacy of HMB3210 Against RSV, MPV and PVM

Figure 16:
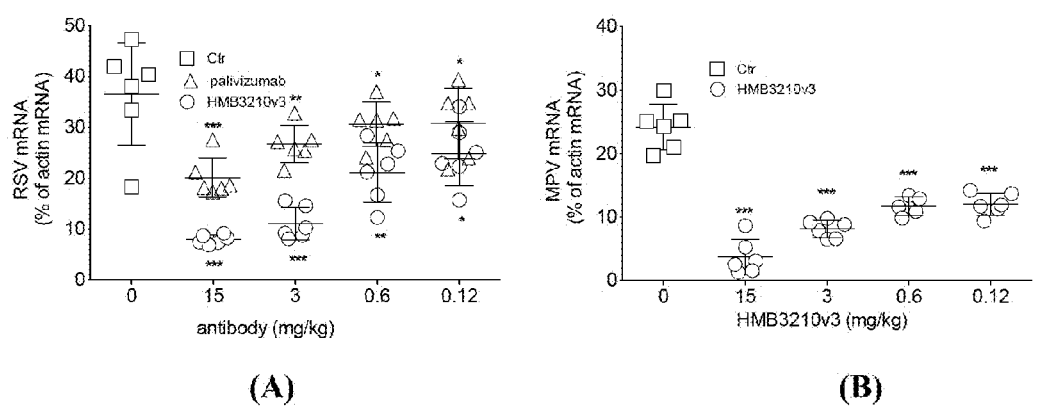
FIG. 16 shows the prophylactic efficacy of HMB3210v3 and Palivizumab in RSV or MPV infection.
Figure 17:
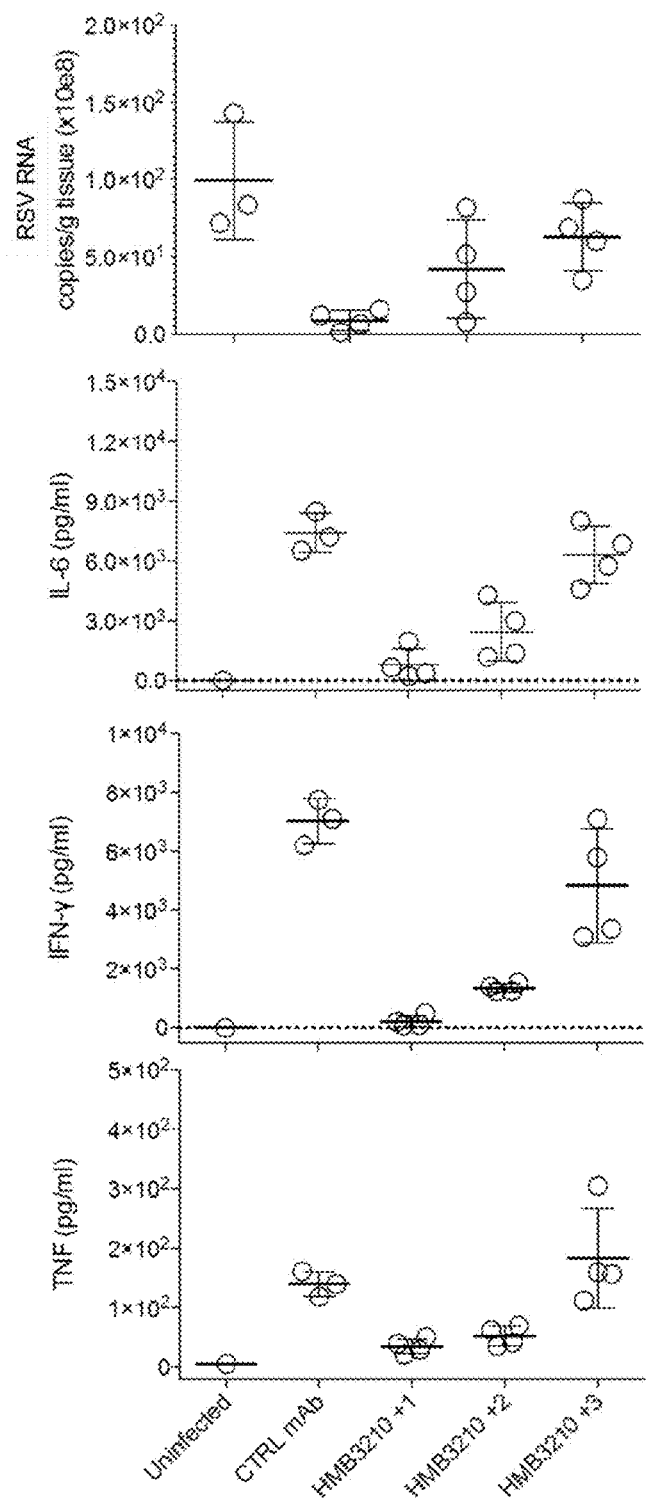
FIG. 17 shows the therapeutic efficacy of HMB3210 in STAT1 deficient mice infected with RSV.

In the RSV mouse models HMB3210 was on average five to ten fold more potent than Palivizumab in reducing RSV lung titers and was effective at concentrations as low as 0.12 mg/kg (FIG. 16a). In the MPV mouse model HMB3210 was comparably effective (FIG. 16b). To test the therapeutic potential of HMB3210 we infected STAT1-deficient mice with RSV and administered HMB3210 on day 1, 2 or 3 post-infection. In spite of the limitation of this model, due to the poor replication of the virus, HMB3210 showed therapeutic efficacy at all time points and reduced viral titers and inflammatory cytokines in the lungs, (FIG. 17).

Figure 18:
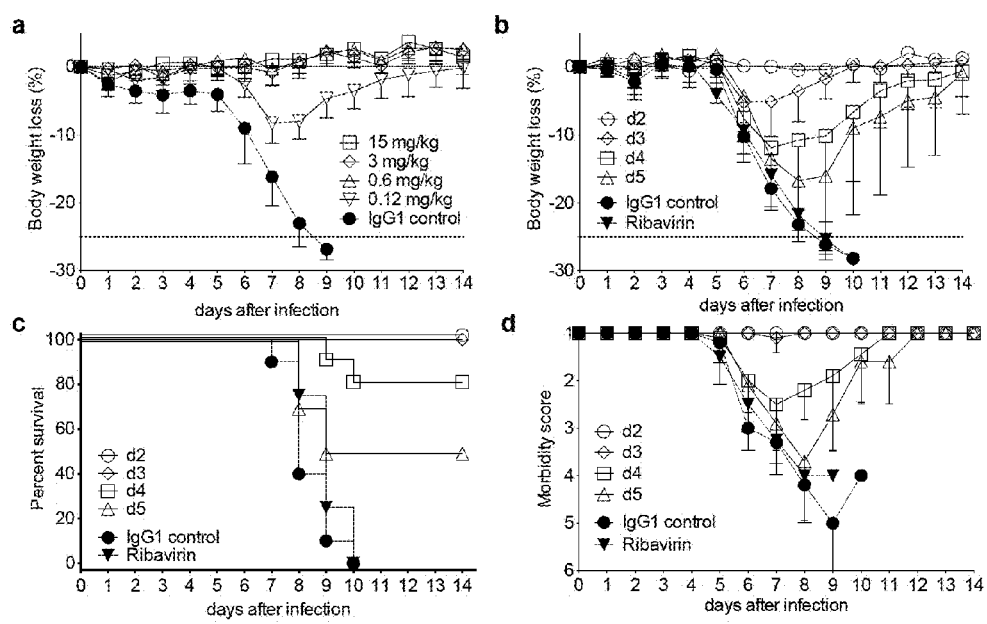
FIG. 18 shows the prophylactic and therapeutic efficacy of HMB3210 in mice infected with a lethal dose of PVM.

To test HMB3210 in a more relevant animal model of acute lower respiratory tract infection, we exploited its cross-reactivity with PVM, a virus that causes a lethal disease in mice following a very low inoculum and recapitulates the features of severe RSV and MPV infection in humans. In a prophylactic setting, HMB3210 fully protected mice from lethality at 0.12 mg/kg and from body weight loss at 0.6 mg/kg (FIG. 18a). Furthermore, in a therapeutic setting HMB3210 completely protected from lethality when administered up to 3 days after infection both at 30 and 5 mg/kg and conferred significant protection when given on day 4 or 5 at 30 mg/kg (FIG. 18b-d). In this system Ribavirin, which is the only approved standard of care for therapy in humans, as previously described (Bonville et al., 2004, Journal of Virology 78:7984-7989) was ineffective.

Figure 19:
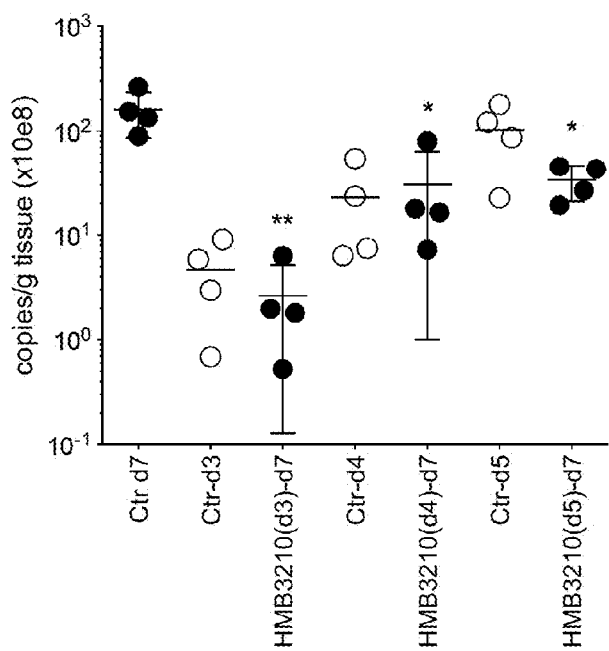
FIG. 19 shows the blocking in the increase of lung viral titers in mice treated with HMB3210v3 on day 3, 4 or 5 after lethal infection with PVM.
Figure 20:
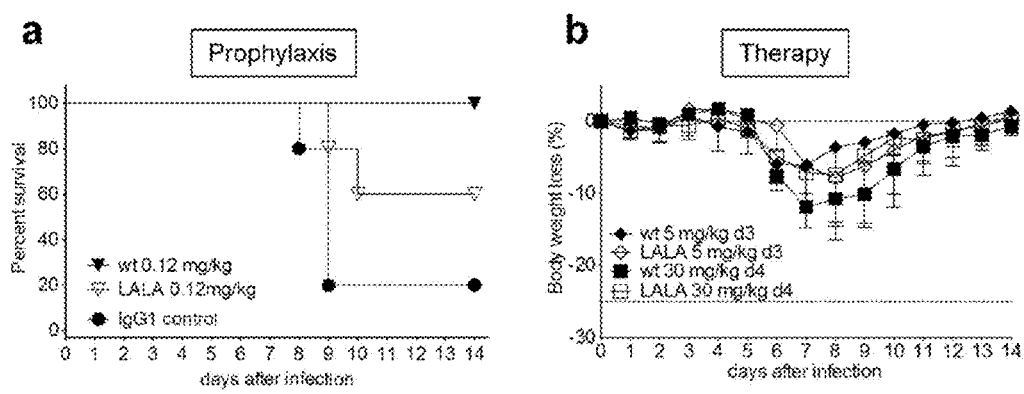
FIG. 20 shows the prophylactic and therapeutic efficacy of HMB3210v3 variants bearing the wild type Fc or the LALA mutation in mice infected with a lethal dose of PVM.

Importantly, therapeutic delivery of HMB3210 efficiently blocked further increase in lung viral RNA (FIG. 19). To address the role of effector mechanisms in vivo we compared the IgG1 HMB3210 with a mutant that lacks complement and Fc receptor binding (HMB3210-LALA). The two antibodies were compared for in vitro neutralizing activity and shown to be equivalent. When administered in limiting amounts in a prophylactic setting (0.12 mg/kg) HMB3210-LALA showed a severely reduced efficacy (FIG. 20a). In contrast, when used in a therapeutic setting HMB3210-LALA was as effective as HMB3210 at all doses tested (FIG. 20b). The therapeutic efficacy of HMB3210 in the PVM infection model, where Ribavirin is not effective, may be due to a combination of factors, such as the potent neutralizing and spreading inhibition activity, the selective recognition of the pre-fusion protein which avoids the consumption of the antibody by the abundant post-fusion proteins acting as decoys, and the failure to select escape mutants. Surprisingly, the therapeutic efficacy of HMB3210 in the PVM mouse model does not require effector functions, suggesting that the antibody activity in vivo relies primarily on viral neutralization and inhibition of viral spread.

Example 14

Figure 5:
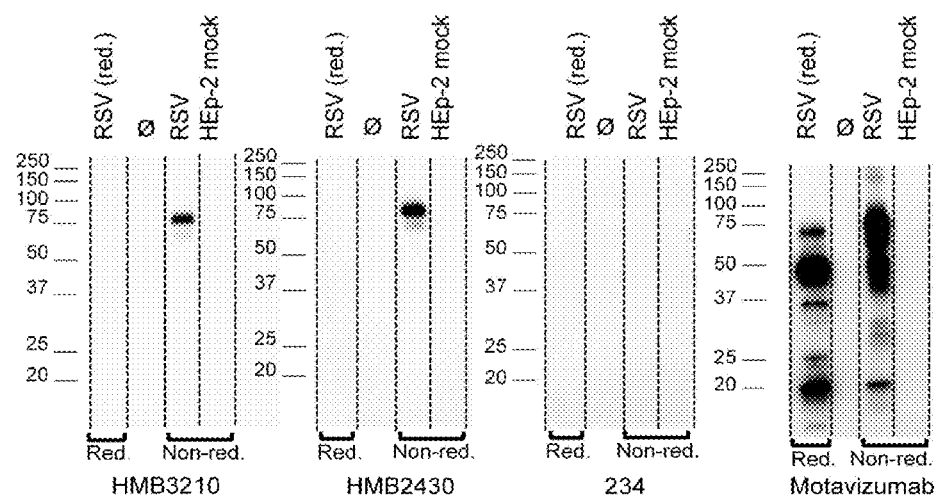
FIG. 5 shows the binding of monoclonal antibodies HMB2430, HMB3210, 234 mAb, and Motavizumab to RSV F protein from lysates of RSV-Hep-2-infected cells under reducing or non-reducing conditions as measured by Western blot analysis.
Figure 6:
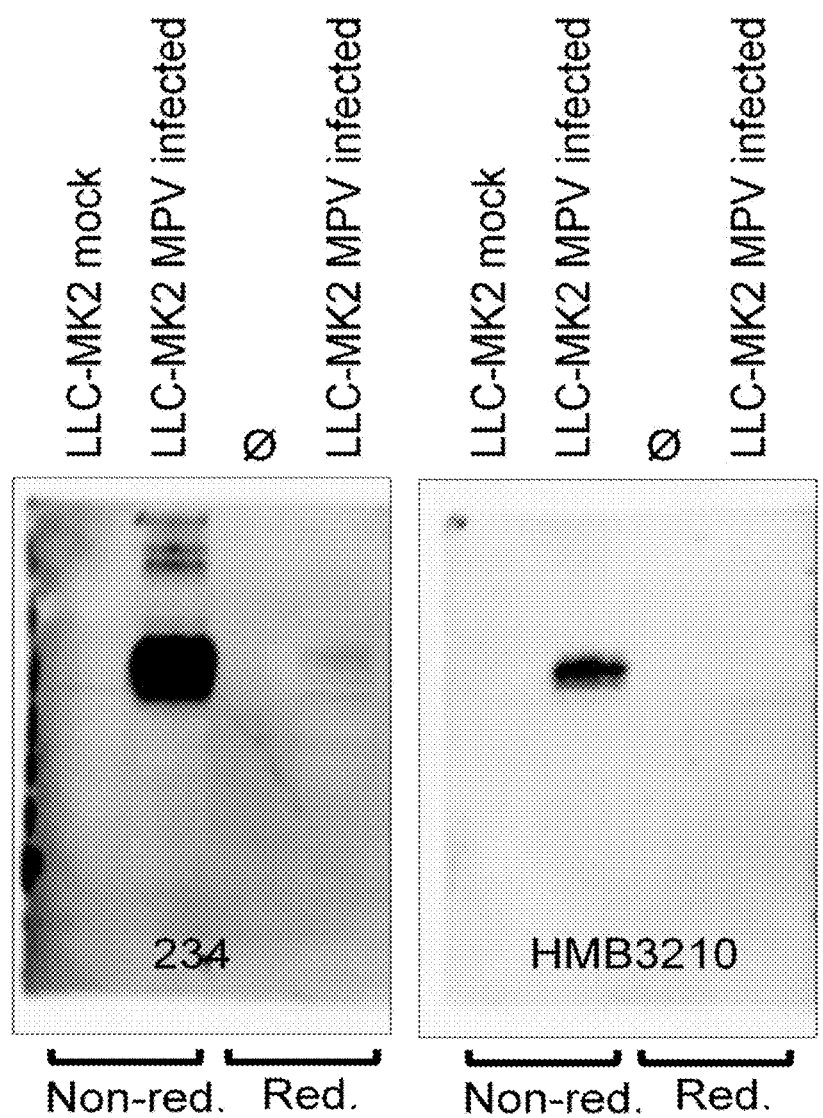
FIG. 6 shows the binding of monoclonal antibodies HMB3210 and 234 mAb to MPV F protein from lysates of MPV-LLC-MK2-infected cells under reducing or non-reducing conditions as measured by Western blot analysis.
Figure 23:
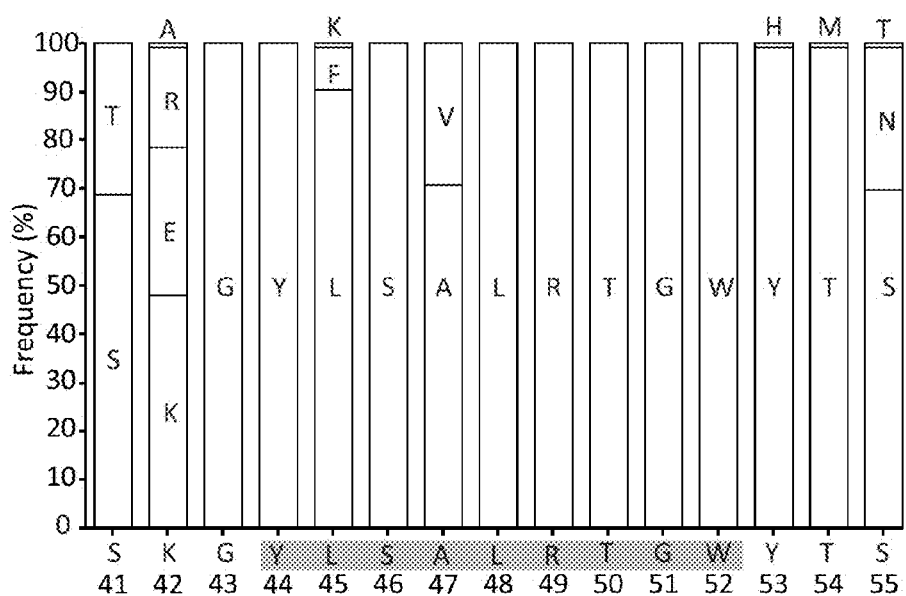
FIG. 23 shows the high degree of conservation of the HMB3210 core epitope in 364 RSV, 162 MPV, 8 BRSV and 5 PVM strains.

HMB3210 Binds to a Highly Conserved Beta Strand on the Pre-Fusion F Protein, Which is not Accessible on the Post-Fusion F Protein To identify the epitope recognized by HMB3210 we screened a library of 7,095 structured peptides covering the full sequence of human RSV F protein. Experiments shown in example 5 showed that HMB3210 reacted in Western blots with RSV and MPV F proteins under non-reducing conditions, suggesting that HMB3210 target an epitope whose conformation is stable in the presence of the anionic detergent SDS (FIGS. 5 and 6). The library screening approach led to the identification of a putative HMB3210 epitope in the N-terminal region of F2, spanning residues SAVSKGYLSALRTGWYTSVIT (SEQ ID NO: 63). The core sequence in this region, YLSALRTGW (SEQ ID NO: 64), is highly conserved between RSV, MPV, BRSV and PVM (FIG. 21) where the variants YLSVLRTGW (SEQ ID NO: 65), YFSALRTGW (SEQ ID NO: 66), YFSVLRTGW (SEQ ID NO: 67), YKSALRTGW (SEQ ID NO: 68) and YKSVLRTGW (SEQ ID NO: 69) are also recognized by HMB3210. This sequence is not exposed on the surface of the post-fusion RSV F protein, but, in a model of the RSV pre-fusion F protein built around the PIV5 F protein structure (Yin, et al., 2006, Nature 439:38-44), is expected to locate in an exposed beta-strand in proximity to the loop region targeted by Palivizumab (FIG. 22). This mapping is consistent with the specificity of HMB3210 for the pre-fusion F protein shown in example 10. This epitope is close, but distinct from that recognized by Palivizumab and is centered around the YLSVLRTGW sequence which is highly conserved amongst 551 virus strains comprising 364 HRSV, 162 HMPV, 8 BRSV and 5 PVM strains (FIG. 23).

The invention claimed is:

1. An isolated, purified or recombinant antibody, or an antigen binding fragment thereof comprising the heavy chain CDR1, CDR2, and CDR3 sequences as set forth in SEQ ID NO: 1, SEQ ID NO: 2, and SEQ ID NO: 3, respectively, and the light chain CDR1, CDR2, and CDR3 sequences as set forth in SEQ ID NO: 4, SEQ ID NO: 5, and SEQ ID NO: 35, respectively, wherein the antibody or antigen binding fragment neutralize infection of RSV, MPV and PVM.

2. The antibody of claim 1, or an antigen binding fragment thereof, that specifically binds a conserved region on the amino terminal portion of the F protein of RSV, MPV, or PVM comprising the amino acid sequence as set forth in any one of SEQ ID NOs: 64-69.

3. The antibody of claim 1, or an antigen binding fragment thereof, wherein the antibody or antigen binding fragment neutralize infection of both group A and group B RSV as well as both group A and group B MPV.

4. The antibody of claim 1, or an antigen binding fragment thereof, wherein the antibody or antigen binding fragment neutralize infection of MPV subgroups A1, A2, B1 and B2.

5. The antibody of claim 1, or an antigen binding fragment thereof, wherein the antibody or antigen binding fragment do not bind to the F protein of RSV at a site that overlaps antigenic site I, antigenic site II, or antigenic site IV.

6. The antibody of claim 1, or an antigen binding fragment thereof, wherein the concentration of antibody or fragment required for 50% neutralization of RSV, MPV or PVM is 500 ng/ml or less.

7. The antibody of claim 1, or an antigen binding fragment thereof, wherein the antibody comprises: a heavy chain variable region having at least 80% sequence identity to the amino acid sequence of SEQ ID NO: 17 and a light chain variable region having at least 80% sequence identity to the amino acid sequence of SEQ ID NO: 37.

8. An isolated, purified or recombinant antibody, or an antigen binding fragment thereof, wherein the antibody comprises a heavy chain variable region comprising the amino acid sequence of SEQ ID NO: 17 and a light chain variable region comprising the amino acid sequence of SEQ ID NO: 37, wherein the antibody or antigen binding fragment neutralize infection of RSV, MPV and PVM.

9. The antibody of claim 1, or an antigen binding fragment thereof, wherein the antibody is HMB3210 variant 3.

10. The antibody of claim 1, or an antigen binding fragment thereof, wherein the antibody is a human antibody, a monoclonal antibody, a human monoclonal antibody, a purified antibody, a single chain antibody, Fab, Fab', F(ab')2, Fv or scFv.

11. A method of treating or attenuating infection by RSV or MPV or both RSV and MPV, comprising: administering to a subject in need thereof, a therapeutically effective amount of the antibody of claim 1, or an antigen binding fragment thereof.

12. A nucleic acid molecule comprising a polynucleotide encoding the antibody, or an antigen binding fragment thereof, of the antibody of claim 1.

13. The nucleic acid molecule of claim 12, wherein the polynucleotide sequence is at least 75% identical to the nucleic acid sequence of any one of SEQ ID NOs: 7-11, 16, 36 or 38.

14. A vector comprising the nucleic acid molecule of claim 12.

15. A cell expressing the antibody of claim 1, or an antigen binding fragment thereof.

16. A pharmaceutical composition comprising the antibody of claim 1, or an antigen binding fragment thereof; a nucleic acid molecule comprising a polynucleotide encoding said antibody, or an antigen binding fragment thereof; a vector comprising said polynucleotide; a cell expressing said vector and a pharmaceutically acceptable diluent or carrier.

17. A pharmaceutical composition comprising a first antibody or an antigen binding fragment thereof, and a second antibody, or an antigen binding fragment thereof, wherein the first antibody is the antibody of claim 1, and the second antibody neutralizes infection of RSV or MPV or both RSV and MPV.

18. A method of reducing RSV or MPV infection, or lowering the risk of RSV or MPV infection, comprising: administering to a subject in need thereof, a therapeutically effective amount of the antibody of claim 1, or an antigen binding fragment thereof.

19. A method of treating or attenuating infection by RSV or MPV or both RSV and MPV, comprising: administering to a subject in need thereof, a therapeutically effective amount of the antibody of claim 2, or an antigen binding fragment thereof.

20. A nucleic acid molecule comprising a polynucleotide encoding the antibody, or an antigen binding fragment thereof, of the antibody of claim 2.

21. A pharmaceutical composition comprising the antibody of claim 2, or an antigen binding fragment thereof, and a pharmaceutically acceptable diluent or carrier.

22. A method of treating or attenuating infection by RSV or MPV or both RSV and MPV, comprising: administering to a subject in need thereof, a therapeutically effective amount of an antibody, or an antigen binding fragment thereof comprising the heavy chain CDR1, CDR2, and CDR3 sequences as set forth in SEQ ID NO: 1, SEQ ID NO: 2, and SEQ ID NO: 3, respectively, and the light chain CDR1, CDR2, and CDR3 sequences as set forth in SEQ ID NO: 4, SEQ ID NO: 5, and SEQ ID NO: 35, respectively, wherein the antibody or antigen binding fragment neutralize infection of RSV, MPV and PVM.

23. A pharmaceutical composition comprising an antibody, or an antigen binding fragment thereof comprising (i) the heavy chain CDR1, CDR2, and CDR3 sequences as set forth in SEQ ID NO: 1, SEQ ID NO: 2, and SEQ ID NO: 3, respectively, and the light chain CDR1, CDR2, and CDR3 sequences as set forth in SEQ ID NO: 4, SEQ ID NO: 5, and SEQ ID NO: 35, respectively, wherein the antibody or antigen binding fragment neutralize infection of RSV, MPV and PVM, and a pharmaceutically acceptable diluent or carrier.

24. A method of treating or attenuating infection by RSV or MPV or both RSV and MPV, comprising: administering to a subject in need thereof, a therapeutically effective amount of an antibody, or an antigen binding fragment thereof, wherein the antibody comprises a heavy chain variable region comprising the amino acid sequence of SEQ ID NO: 17 and a light chain variable region comprising the amino acid sequence of SEQ ID NO: 37, wherein the antibody or antigen binding fragment neutralize infection of RSV, MPV and PVM.

25. A nucleic acid molecule comprising a polynucleotide encoding the antibody, or an antigen binding fragment thereof, of the antibody of claim 8.

26. A pharmaceutical composition comprising an antibody, or an antigen binding fragment thereof, wherein the antibody comprises a heavy chain variable region comprising the amino acid sequence of SEQ ID NO: 17 and a light chain variable region comprising the amino acid sequence of SEQ ID NO: 37, wherein the antibody or antigen binding fragment neutralize infection of RSV, MPV and PVM, and a pharmaceutically acceptable diluent or carrier.

\* \* \* \* \*